United States Patent
Ogiwara et al.

(10) Patent No.: US 10,249,826 B2
(45) Date of Patent: Apr. 2, 2019

(54) COMPOUND, ORGANIC ELECTROLUMINESCENT ELEMENT AND ELECTRONIC DEVICE

(71) Applicant: IDEMITSU KOSAN CO., LTD., Chiyoda-ku (JP)

(72) Inventors: Toshinari Ogiwara, Sodegaura (JP); Kei Yoshida, Sodegaura (JP); Satomi Tasaki, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 137 days.

(21) Appl. No.: 14/908,082

(22) PCT Filed: Mar. 31, 2015

(86) PCT No.: PCT/JP2015/060223
§ 371 (c)(1),
(2) Date: Jan. 27, 2016

(87) PCT Pub. No.: WO2015/159706
PCT Pub. Date: Oct. 22, 2015

(65) Prior Publication Data
US 2016/0172599 A1    Jun. 16, 2016

(30) Foreign Application Priority Data

Apr. 16, 2014    (JP) .................................. 2014-085041
Feb. 6, 2015    (JP) .................................. 2015-022733

(51) Int. Cl.
*H01L 51/52*    (2006.01)
*H01L 51/54*    (2006.01)
(Continued)

(52) U.S. Cl.
CPC ...... *H01L 51/0067* (2013.01); *C07D 491/147* (2013.01); *C09K 11/06* (2013.01);
(Continued)

(58) Field of Classification Search
None
See application file for complete search history.

(56) References Cited

U.S. PATENT DOCUMENTS

2006/0267001 A1* 11/2006 Hung .................. H01L 51/5012
257/40
2012/0168734 A1    7/2012 Park et al.
(Continued)

FOREIGN PATENT DOCUMENTS

JP    2013245179 A  * 12/2013
JP    6220341 B2    10/2017
(Continued)

OTHER PUBLICATIONS

Machine translation of JP 2013245179 A.*
(Continued)

*Primary Examiner* — Magali P Slawski
*Assistant Examiner* — William E McClain
(74) *Attorney, Agent, or Firm* — Oblon, McClelland, Maier & Neustadt, L.L.P.

(57) ABSTRACT

An organic electroluminescence device includes an anode, an emitting layer and a cathode, in which the emitting layer includes a first compound and a second compound. The first compound is a delayed-fluorescent compound represented by a formula (1) below. The second compound includes at least one of a partial structure represented by a formula (21)
(Continued)

below and a partial structure represented by a formula (22) below in one molecule.

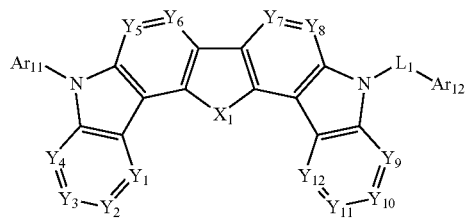

(1)

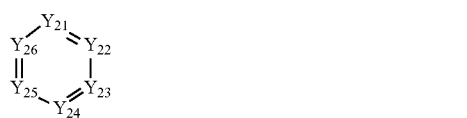

(21)

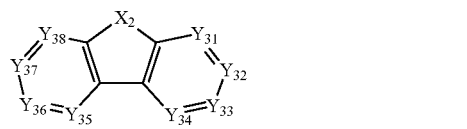

(22)

37 Claims, 3 Drawing Sheets

(51) Int. Cl.
*H01L 51/00* (2006.01)
*C09K 11/06* (2006.01)
*C07D 491/147* (2006.01)
*H01L 51/50* (2006.01)

(52) U.S. Cl.
CPC ...... *H01L 51/0071* (2013.01); *H01L 51/0072* (2013.01); *H01L 51/0073* (2013.01); *C09K 2211/1007* (2013.01); *C09K 2211/1029* (2013.01); *C09K 2211/1033* (2013.01); *C09K 2211/1048* (2013.01); *C09K 2211/1051* (2013.01); *C09K 2211/1059* (2013.01); *C09K 2211/1088* (2013.01); *H01L 51/5012* (2013.01)

(56) References Cited

U.S. PATENT DOCUMENTS

2012/0241732 A1 9/2012 Endo et al.
2014/0158992 A1* 6/2014 Xia ............... H01L 51/0067 257/40
2014/0336379 A1* 11/2014 Adachi ............ C07D 403/14 544/209
2015/0228909 A1* 8/2015 Kim ............... H01L 51/0067 257/40

FOREIGN PATENT DOCUMENTS

| WO | 03/080760 A1 | 10/2003 | |
|---|---|---|---|
| WO | 2011/070963 A1 | 6/2011 | |
| WO | 2011/132683 A1 | 10/2011 | |
| WO | 2012/153780 A1 | 11/2012 | |
| WO | 2013/038650 A1 | 3/2013 | |
| WO | 2014/057684 A1 | 4/2014 | |
| WO | WO-2014057685 A1 * | 4/2014 | ........... C07D 487/14 |
| WO | 2014/112359 A1 | 7/2014 | |
| WO | WO-2014148047 A1 * | 9/2014 | ............. H05B 33/14 |
| WO | WO-2014208698 A1 * | 12/2014 | ......... C07D 491/048 |

OTHER PUBLICATIONS

Lee, et al. "High-efficiency organic light-emitting diodes utilizing thermally activated delayed fluorescence from triazine-based donor-acceptor hybrid molecules." Applied Physics Letters 101.9 (2012): 093306.*
Li, et al. "Dicarbazolyldicyanobenzenes as thermally activated delayed fluorescence emitters: effect of substitution position on photoluminescent and electroluminescent properties." Chemistry Letters 43.3 (2013): 319-321.*
Zhang, et al. "Towards ideal electrophosphorescent devices with low dopant concentrations: the key role of triplet up-conversion." Journal of Materials Chemistry C 2.42 (2014): 8983-8989.*
Uoyama, et al. "Highly efficient organic light-emitting diodes from delayed fluorescence." Nature 492.7428 (2012): 234.*
Hiroyuki Tanaka, et al., "Efficient green thermally activated delayed fluorescence (TADF) from a phenoxazine-triphenyltriazine (PXZ-TRZ) derivative", Chemical Communications, vol. 48, pp. 11392-11394, (2012).
Chihaya Adachi et al., "Device Physics of Organic Semiconductors", Total 19 Pages, (2012) (with English Translation).
Keigo Satoh, et al., "Expression of Highly-Efficient Thermally-Activated Delayed-Fluorescence and Application Thereof to OLED", Organic El Symposium, Total 6 Pages, (2010) (with English Translation).
Katumi Tokumaru, "Organic Photochemical Reaction Theory", Total 9 Pages, (1973) (with English Translation).
International Search Report dated Jun. 9, 2015 in PCT/JP15/060223 Filed Mar. 31, 2015.
Japanese Office Action dated Mar. 13, 2018 in Patent Application No. 2015-022733 (with English translation), 5 pages.

* cited by examiner

COMPOUND, ORGANIC ELECTROLUMINESCENT ELEMENT AND ELECTRONIC DEVICE

TECHNICAL FIELD

The present invention relates to a compound, an organic electroluminescence device and an electronic device.

BACKGROUND ART

When a voltage is applied to an organic electroluminescence device (hereinafter, occasionally referred to as an organic EL device), holes are injected from an anode into an emitting layer and electrons are injected from a cathode into the emitting layer. The injected electrons and holes are recombined in an emitting layer to form excitons. According to the electron spin statistics theory, singlet excitons and triplet excitons are generated at a ratio of 25%:75%.

A fluorescent organic EL device, which uses emission caused by singlet excitons, is inferred to exhibit an internal quantum efficiency of 25% at a maximum. Although having been used in full-color displays of a mobile phone, TV and the like, the fluorescent EL device is required to use triplet excitons in addition to singlet excitons to further enhance efficiency.

In view of the above, a highly efficient fluorescent organic EL device using delayed fluorescence has been studied.

For instance, a thermally activated delayed fluorescence (TADF) mechanism has been studied. The TADF mechanism utilizes a phenomenon in which inverse intersystem crossing from triplet excitons to singlet excitons is thermally generated by using a material having a small energy gap ($\Delta$ST) between the singlet level and the triplet level. Thermally activated delayed fluorescence is described, for instance, in "Yuki Hando-tai no Debaisu Bussei (Device Physics of Organic Semiconductors)" edited by Chihaya Adachi, published Mar. 22, 2012 by Kodansha Company Ltd, pages 261 to 262." For instance, Patent Literature 1 and non-Patent Literature 1 disclose organic EL devices using the TADF mechanism.

However, further improvement in luminous efficiency of the organic EL device in a high current density region is still desired.

CITATION LIST

Patent Literature(s)

Patent Literature 1: International Publication No. WO2011/070963

Non-Patent Literature

Non-Patent Literature 1: Chihaya Adachi et al. "Efficient green thermally activated delayed fluorescence (TADF) from a phenoxazine-triphenyltriazine (PXZ-TRZ) derivative", Chemical Communications, in 2012, DOI:10.1039/c2cc36237f

SUMMARY OF THE INVENTION

Problems to be Solved by the Invention

An object of the invention is to provide an organic electroluminescence device having an improved luminous efficiency in a high current density region, a compound used for the organic electroluminescence device, and an electronic device including the organic electroluminescence device.

Means for Solving the Problems

According to an aspect of the invention, an organic electroluminescence device includes an anode, an emitting layer and a cathode, in which the emitting layer includes a first compound and a second compound, the first compound is a delayed-fluorescent compound represented by a formula (1) below, and the second compound has at least one of a partial structure represented by a formula (21) below and a partial structure represented by a formula (22) below in one molecule.

[Formula 1]

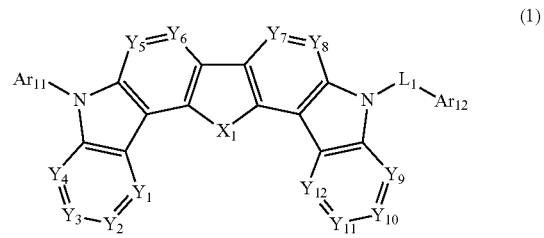

(1)

In the formula (1), $Ar_{11}$ and $Ar_{12}$ are each independently a substituted or unsubstituted aromatic hydrocarbon group having 6 to 30 ring carbon atoms, or a substituted or unsubstituted heterocyclic group having 5 to 30 ring atoms; $L_1$ is a single bond or a linking group, the linking group in $L_1$ being a substituted or unsubstituted aromatic hydrocarbon group having 6 to 30 ring carbon atoms or a substituted or unsubstituted heterocyclic group having 5 to 30 ring atoms; $Y_1$ to $Y_{12}$ are each independently a nitrogen atom or $CR_1$; $X_1$ is an oxygen atom, a sulfur atom, N—$R_{10}$, $CR_{11}R_{12}$, $SiR_{13}R_{14}$ or $GeR_{15}R_{16}$; $R_1$ and $R_{10}$ to $R_{16}$ are each independently a hydrogen atom or a substituent; when $R_1$ and $R_{10}$ to $R_{16}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group; a plurality of $R_1$ are optionally mutually the same or different; and when at least two of the plurality of $R_1$ are substituents, the substituents $R_1$ are optionally mutually bonded to form a cyclic structure.

[Formula 2]

(21)

-continued

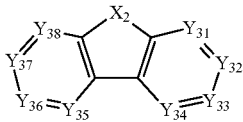
(22)

In the formula (21): $Y_{21}$ to $Y_{26}$ are each independently a nitrogen atom or a carbon atom bonded to another atom in the molecule of the second compound; and at least one of $Y_{21}$ to $Y_{26}$ is a carbon atom bonded to another atom in the molecule of the second compound. In the formula (22): $Y_{31}$ to $Y_{38}$ are each independently a nitrogen atom or a carbon atom bonded to another atom in the molecule of the second compound; at least one of $Y_{31}$ to $Y_{38}$ is a carbon atom bonded to another atom in the molecule of the second compound; and $X_2$ is a nitrogen atom, an oxygen atom or a sulfur atom.

According to another aspect of the invention, the delayed-fluorescent compound represented by the formula (1) is provided.

According to still another aspect of the invention, an electronic device including the organic electroluminescence device according to the above aspect is provided.

According to the above aspects of the invention, an organic electroluminescence device having an improved luminous efficiency in a high current density region, a compound used for the organic electroluminescence device, and an electronic device including the organic electroluminescence device are provided.

DESCRIPTION OF EMBODIMENT(S)

First Exemplary Embodiment
Arrangement(s) of Organic EL Device

The organic EL device in the first exemplary embodiment includes a pair of electrodes and an organic layer between the pair of electrodes. The organic layer includes a plurality of layers formed of an organic compound. The organic layer may further include an inorganic compound. In the organic EL device in the exemplary embodiment, at least one layer of the organic layer(s) is the emitting layer. Specifically, for instance, the organic layer may consist of a single emitting layer, or may include layers usable in a typical organic EL device, such as a hole injecting layer, a hole transporting layer, an electron injecting layer, an electron transporting layer and a blocking layer.

Typical device arrangements of an organic EL device include the following arrangements (a) to (e) and the like:
(a) anode/emitting layer/cathode;
(b) anode/hole injecting•transporting layer/emitting layer/cathode;
(c) anode/emitting layer/electron injecting•transporting layer/cathode;
(d) anode/hole injecting-transporting layer/emitting layer/electron injecting•transporting layer/cathode; and
(e) anode/hole injecting•transporting layer/emitting layer/blocking layer/electron injecting•transporting layer/cathode.

The arrangement (d) is preferably used among the above arrangements. However, the arrangement of the invention is not limited to the above arrangements. The "emitting layer" refers to an organic layer having an emitting function. The term "hole injecting/transporting layer" means at least one of a hole injecting layer and a hole transporting layer. The term "electron injecting/transporting layer" means at least one of an electron injecting layer and an electron transporting layer. Herein, when the hole injecting layer and the hole transporting layer are provided, the hole injecting layer is preferably provided between the hole transporting layer and the anode. When the electron injecting layer and the electron transporting layer are provided, the electron injecting layer is preferably provided between the electron transporting layer and the cathode. Moreover, each of the hole injecting layer, hole transporting layer, electron transporting layer and electron injecting layer may be provided by a single layer or a plurality of layers.

Figure 1:
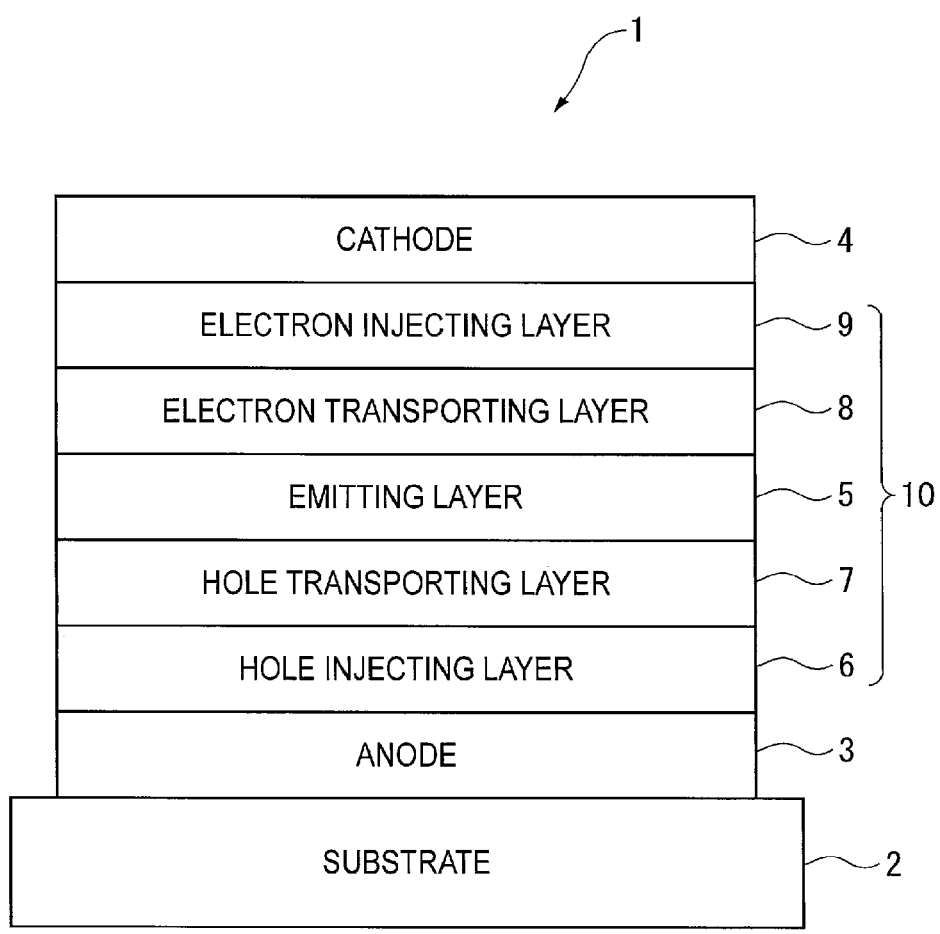
FIG. 1 shows a schematic structure of an organic electroluminescence device according to an exemplary embodiment of the invention.

FIG. 1 schematically shows an arrangement of an organic EL device according to the exemplary embodiment.

An organic EL device 1 includes a light-transmissive substrate 2, an anode 3, a cathode 4 and an organic layer 10 disposed between the anode 3 and the cathode 4. The organic layer 10 includes a hole injecting layer 6, a hole transporting layer 7, an emitting layer 5, an electron transporting layer 8, and an electron injecting layer 9, which are sequentially laminated from the anode 3.

Emitting Layer

The emitting layer 5 of the organic EL device 1 contains a first compound and a second compound. The emitting layer 5 may contain a metal complex. However, in the exemplary embodiment, the emitting layer 5 preferably contains no phosphorescent metal complex, more preferably contains no other metal complex in addition to the phosphorescent metal complex.

First Compound

A first compound of the exemplary embodiment is represented by a formula (1) below. The first compound in the exemplary embodiment is a delayed fluorescent compound. The first compound of the exemplary embodiment is not a metal complex.

[Formula 3]

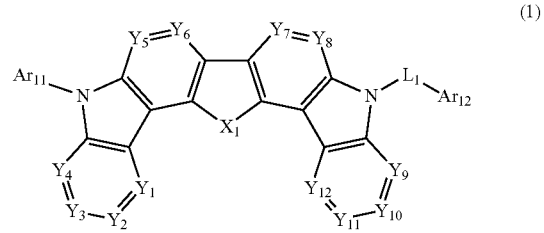
(1)

In the formula (1): $Ar_{11}$ and $Ar_{12}$ are each independently a substituted or unsubstituted aromatic hydrocarbon group having 6 to 30 ring carbon atoms, or a substituted or unsubstituted heterocyclic group having 5 to 30 ring atoms.

$L_1$ is a single bond or a linking group. The linking group in $L_1$ is a substituted or unsubstituted aromatic hydrocarbon group having 6 to 30 ring carbon atoms or a substituted or unsubstituted heterocyclic group having 5 to 30 ring atoms.

$Y_1$ to $Y_{12}$ are each independently a nitrogen atom or $CR_1$.

$X_1$ is an oxygen atom, a sulfur atom, N—$R_{10}$, $CR_{11}R_{12}$, $SiR_{13}R_{14}$ or $GeR_{15}R_{16}$.

$R_1$ and $R_{10}$ to $R_{16}$ are each independently a hydrogen atom or a substituent. When $R_1$ and $R_{10}$ to $R_{16}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group.

A plurality of $R_1$ are optionally mutually the same or different. When at least two of the plurality of $R_1$ are substituents, the substituents $R_1$ are optionally mutually bonded to form a cyclic structure.

In the exemplary embodiment, —$Ar_{11}$ is preferably different from —$L_1$-$Ar_{12}$. In other words, in the structure represented by the formula (1), $Ar_{11}$ bonded to a nitrogen atom is preferably different from $L_1$-$Ar_{12}$ bonded to another nitrogen atom.

In the exemplary embodiment, it is preferable that $Ar_{11}$ is an unsubstituted aromatic hydrocarbon group having 6 to 30 ring carbon atoms or an unsubstituted heterocyclic group having 5 to 30 ring atoms and $L^1$ is a linking group. Also in this arrangement, in the structure represented by the formula (1), $Ar_{11}$ bonded to a nitrogen atom is different from $L_1$-$Ar_{12}$ bonded to another nitrogen atom. In addition, the substituent(s) for $Ar_{11}$ is preferably a cyano group.

In the exemplary embodiment, the first compound is preferably represented by a formula (10) below.

[Formula 4]

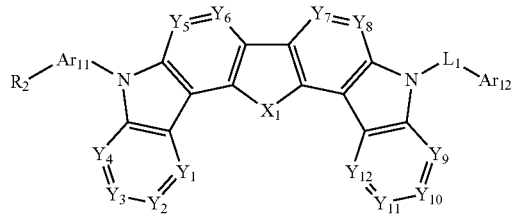

(10)

In the formula (10), $X_1$, $Y_1$ to $Y_{12}$, $L_1$, $Ar_{11}$ and $Ar_{12}$ respectively represent the same as $X_1$, $Y_1$ to $Y_{12}$, $L_1$, $Ar_{11}$ and $Ar_{12}$ in the formula (1). $R_2$ is a substituent and is a substituted or unsubstituted aromatic hydrocarbon group having 6 to 30 ring carbon atoms or a substituted or unsubstituted heterocyclic group having 5 to 30 ring atoms.

In the formula (10), —$Ar_{11}$—$R_2$ is preferably different from —$L_1$-$Ar_{12}$. In other words, in the structure represented by the formula (10), $Ar_{11}$—$R_2$ bonded to a nitrogen atom is preferably different from $L_1$-$Ar_{12}$ bonded to another nitrogen atom.

In the exemplary embodiment, $Y_1$ to $Y_{12}$ are preferably $CR_1$, in which $R_1$ is more preferably a hydrogen atom. In this arrangement, the formula (1) is represented by a formula (1C) below.

[Formula 5]

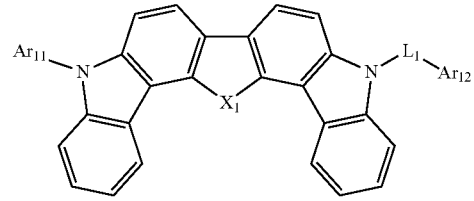

(1C)

In the formula (1C), $X_1$, $L_1$, $Ar_{11}$ and $Ar_{12}$ respectively represent the same as $X_1$, $L_1$, $Ar_{11}$ and $Ar_{12}$ in the formula (1).

In the exemplary embodiment, $Ar_{12}$ is preferably a group represented by a formula (11) below.

[Formula 6]

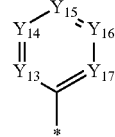

(11)

In the formula (11): $Y_{13}$ to $Y_{17}$ are each independently a nitrogen atom or $CR_3$.

$R_3$ is a hydrogen atom or a substituent. When $R_3$ is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group.

A plurality of $R_3$ are optionally mutually the same or different. When at least two of the plurality of $R_3$ are substituents, the substituents R3 are optionally mutually bonded to form a cyclic structure. In the formula (11), a wavy line shows a bonding position to $L_1$.

In the exemplary embodiment, when $Ar_{12}$ is a group represented by the formula (11), the formula (1) is represented by a formula (1B) below.

[Formula 7]

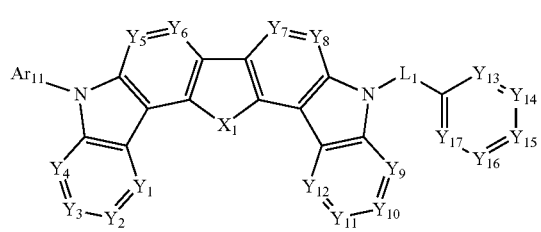

(1B)

In the formula (1B), $X_1$, $Y_1$ to $Y_{12}$, $L_1$ and $Ar_{11}$ respectively represent the same as $X_1$, $Y_1$ to $Y_{12}$, $L_1$ and $Ar_{11}$ of the formula (1), and $Y_{13}$ to $Y_{17}$ respectively represent the same as $Y_{13}$ to $Y_{17}$ of the formula (11).

In the exemplary embodiment, at least one of $Y_{13}$ to $Y_{17}$ is preferably a nitrogen atom, more preferably one to three of $Y_{13}$ to $Y_{17}$ are nitrogen atoms.

In the exemplary embodiment, $Y_{13}$ to $Y_{17}$ are preferably each independently $CR_3$. In this arrangement, a plurality of $R_3$ are optionally mutually the same or different.

In the exemplary embodiment, at least one of $Y_{13}$ to $Y_{17}$ is preferably $CR_3$, in which at least one of $R_3$ is preferably a cyano group.

In the exemplary embodiment, $Ar_{12}$ is preferably a group represented by a formula (11a) below, a group represented by a formula (11b) below, a group represented by a formula (11c) below, a group represented by a formula (11d) below, or a group represented by a formula (11e) below.

[Formula 8]

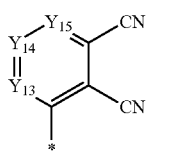
(11a)

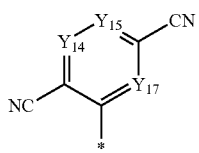
(11b)

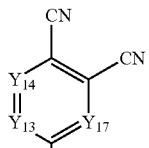
(11c)

[Formula 9]

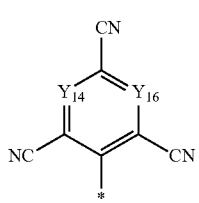
(11d)

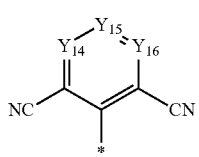
(11e)

In the formulae (11a) to (11e), $Y_{13}$ to $Y_{17}$ respectively represent the same as $Y_{13}$ to $Y_{17}$ in the formula (11) In the formulae (11a) to (11e), a wavy line shows a bonding position to $L_1$.

In the exemplary embodiment, $Ar_{12}$ is preferably a group represented by a formula (11f) below or a group represented by a formula (11h) below.

[Formula 10]

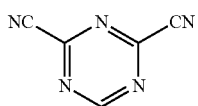
(11f)

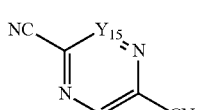
(11g)

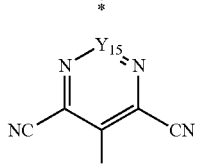
(11h)

In the formulae (11g) to (11h), $Y_{15}$ represents the same as $Y_{15}$ in the formula (11). In the formulae (11f) to (11h), a wavy line shows a bonding position to $L_1$.

In the formulae (11a) to (11h), $Y_{13}$ to $Y_{17}$ are also preferably $CR_3$. In this arrangement, $R_3$ is preferably a hydrogen atom. Moreover, $R_3$ may be a substituent. The substituent $R_3$ is preferably not a cyano group. When a plurality of substituents $R_3$ are present, the plurality of $R_3$ are optionally mutually the same or different.

In the exemplary embodiment, $Ar_{12}$ is preferably substituted by at least one electron attracting group. Examples of the electron attracting group include a cyano group, fluoro group, alkyl halide group, alkyl-substituted alkyl halide group, nitro group and carbonyl group. Among the examples of the electron attracting group, a cyano group, fluoro group, alkyl halide group or alkyl-substituted alkyl halide group is preferable and a cyano group is more preferable. When a plurality of electron attracting groups substituting $Ar_{12}$ are present, the plurality of electron attracting groups are optionally mutually the same or different.

When $Ar_{12}$ is substituted by a cyano group, $Ar_{12}$ is preferably substituted by a cyano group or by two cyano groups. However, when $Ar_{12}$ is substituted by a cyano group, $Ar_{12}$ is also preferably substituted by three or more cyano groups.

In the exemplary embodiment, $Ar_{12}$ is also preferably a substituted or unsubstituted pyridinyl group, substituted or unsubstituted pyrimidinyl group, or substituted or unsubstituted triazinyl. For instance, $Ar_{12}$ is preferably a group represented by any one of formulae (iii), (11j), (11k), (11m), (11n), (11p), (11q), (11r) and (11s) below.

[Formula 11]

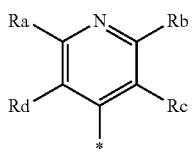
(11i)

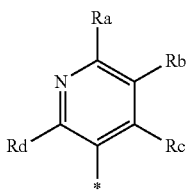

(11j)

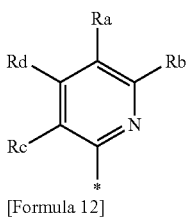

[Formula 12]

(11k)

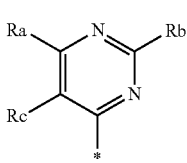

(11m)

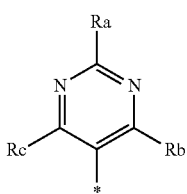

(11n)

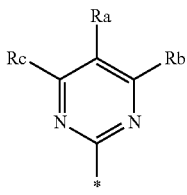

[Formula 13]

(11p)

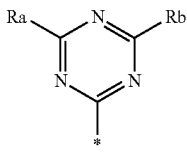

(11q)

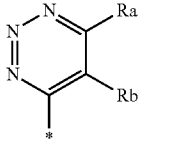

(11r)

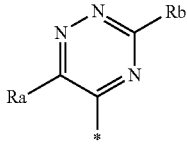

(11s)

In the formulae (11i), (11j), (11k), (11m), (11n), (11p), (11q), (11r) and (11s), Ra, Rb, Rc and Rd are each independently a hydrogen atom or a substituent. When Ra, Rb, Rc and Rd are substituents, each of the substituents is selected from the group consisting of the examples of the substituent listed when $R_3$ is the substituent. When Ra, Rb, Rc and Rd are substituents, each of the substituents is preferably not a cyano group.

Among the groups represented by the formulae (11i), (11j), (11k), (11m), (11n), (11p), (11q), (11r) and (11s), the group represented by the formula (11q) is preferable. Ra and Rb are each independently preferably selected from the group consisting of a substituted or unsubstituted aromatic hydrocarbon group having 6 to 30 ring carbon atoms and a substituted or unsubstituted heterocyclic group having 5 to 30 ring atom, more preferably selected from the group consisting of a substituted or unsubstituted aromatic hydrocarbon group having 6 to 20 ring carbon atoms and a substituted or unsubstituted heterocyclic group having 5 to 20 ring atoms. In the formulae (11i), (11j), (11k), (11m), (11n), (11p), (11q), (11r), and (11s), a wavy line shows a bonding position to $L_1$.

In the exemplary embodiment, $L_1$ is preferably a substituted or unsubstituted aromatic hydrocarbon group having 6 to 30 ring carbon atoms or a substituted or unsubstituted heterocyclic group having 5 to 30 ring atoms, more preferably a substituted or unsubstituted aromatic hydrocarbon group having 6 to 20 ring carbon atoms or a substituted or unsubstituted heterocyclic group having 5 to 20 ring atoms. $L_1$ is preferably a phenylene group, a biphenyldiyl group or a naphthylene group, more preferably a phenylene group or a biphenyldiyl group, further preferably a p-phenylene group. Substituent(s) for $L^1$ is preferably at least one of a phenyl group, an alkyl group and a cyano group.

In the exemplary embodiment, $X_1$ is preferably an oxygen atom or a sulfur atom, preferably an oxygen atom.

In the exemplary embodiment, $Ar_{11}$ is preferably a substituted or unsubstituted aromatic hydrocarbon group having 6 to 30 ring carbon atoms, more preferably a substituted or unsubstituted aromatic hydrocarbon group having 6 to 20 ring carbon atoms, further preferably an aromatic hydrocarbon group selected from the group consisting of a phenyl group, biphenyl group, terphenyl group, naphthyl group, phenanthryl group and triphenylenyl group.

In the exemplary embodiment, the substituted silyl group is preferably represented by —Si($R_{100}$)$_3$. $R_{100}$ is each independently a substituent. The substituent $R_{100}$ is preferably a substituted or unsubstituted alkyl group having 1 to 30 carbon atoms or a substituted or unsubstituted aromatic hydrocarbon group having 6 to 30 ring carbon atoms. A plurality of $R_{100}$ are optionally mutually the same or different.

In the exemplary embodiment, the substituted germanium group is preferably represented by —Ge($R_{101}$)$_3$. $R_{101}$ is each independently a substituent. The substituent $R_{101}$ is preferably a substituted or unsubstituted alkyl group having 1 to 30 carbon atoms or a substituted or unsubstituted aromatic hydrocarbon group having 6 to 30 ring carbon atoms. A plurality of $R_{101}$ are optionally mutually the same or different.

In the exemplary embodiment, a substituted phosphine oxide is preferably represented by a formula (100) below.

[Formula 14]

(100)

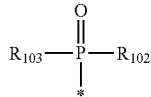

In the formula (100), $R_{102}$ and $R_{103}$ are each independently substituents. The substituents $R_{102}$ and $R_{103}$ are preferably a substituted or unsubstituted alkyl group having 1 to 30 carbon atoms or a substituted or unsubstituted aromatic hydrocarbon group having 6 to 30 ring carbon atoms.

Delayed Fluorescence

Thermally activated delayed fluorescence is described in "Device Physics of Organic Semiconductor" edited by Chihaya Adachi, pages 261 to 268, published by Kodansha Company Ltd. This document describes that, when an energy gap $\Delta E_{13}$ between a singlet state and a triplet state of a fluorescent material can be decreased, in spite of a typical low transition probability, inverse energy transfer from the triplet state to the singlet state occurs at a high efficiency to express thermally stimulated delayed fluorescence (TADF). Further, a generating mechanism of delayed fluorescence is described in FIG. 10.38 in this document. The first compound in the exemplary embodiment is a compound emitting delayed fluorescence to be generated by such a mechanism.

Delayed fluorescence can be observed by measuring transient PL (Photo Luminescence).

Behavior of delayed fluorescence can also be analyzed based on the decay curve obtained by measuring the transient PL. The transitional PL measurement is a method for measuring reduction behavior (transitional property) of PL emission obtained after irradiating pulse laser on a sample to excite the sample and stopping irradiating the pulse laser. PL emission using a TADF material is divided into an emission component from singlet excitons generated by the first PL excitation and an emission component from singlet excitons generated via triplet excitons. Lifetime of the singlet excitons initially generated in the PL excitation is very short at a nano-second order. Accordingly, the emission from the singlet excitons is rapidly reduced after pulse laser radiation.

On the other hand, since delayed fluorescence provides emission from singlet excitons generated through long-life triplet excitons, emission is gradually reduced. Thus, there is a large difference in time between the emission from the singlet excitons initially generated in the PL excitation and the emission from the singlet excitons derived from the triplet excitons. Accordingly, a luminous intensity derived from delayed fluorescence is obtainable.

Figure 2:
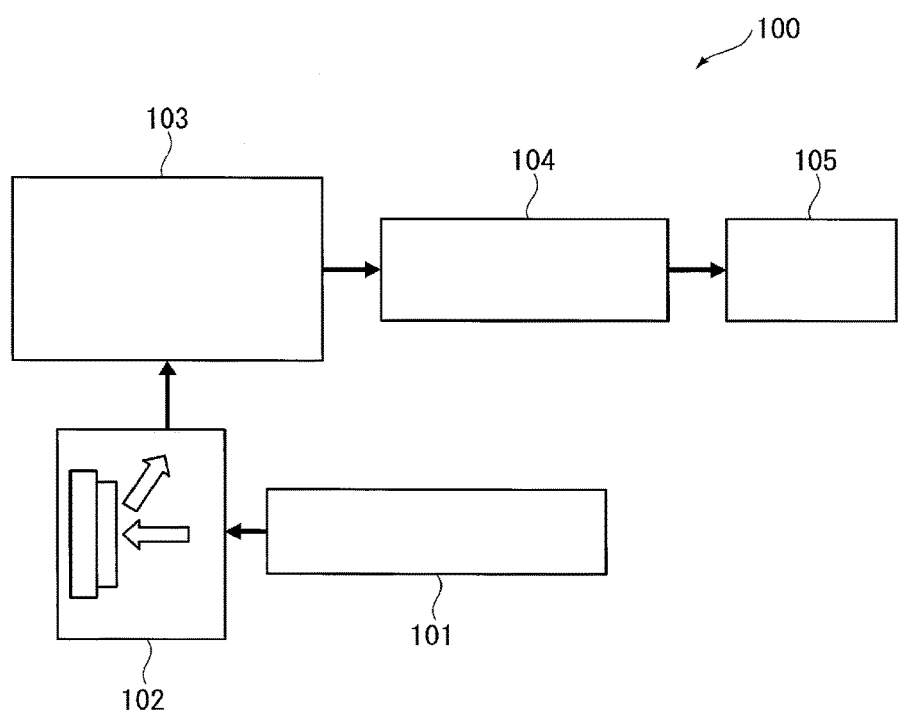
FIG. 2 is a schematic illustration of a measuring device of transient PL.

FIG. 2 is a schematic illustration of an exemplary device for measuring the transient PL.

In the exemplary embodiment, a transient PL measuring device 100 includes a pulse laser 101 configured to irradiate light having a predetermined wavelength, a sample chamber 102 configured to house a measurement sample, a spectrometer 103 configured to disperse the light irradiated from the measurement sample, a streak camera 104 configured to produce a two-dimensional image, and a personal computer 105 configured to import and analyze the two-dimensional image. A device usable for the measurement of the transient PL is not limited to the device described in the first exemplary embodiment.

The sample housed in the sample chamber 102 is obtained by forming a thin film, in which a doping material is doped to a matrix material at a concentration of 12 mass %, on the quartz substrate.

The thin film sample housed in the sample chamber 102 is irradiated with pulse laser from the pulse laser 101 to be excited. Emission is extracted at 90 degrees angle relative to the excited light. The extracted emission is dispersed with the spectrometer 103 to form a two-dimensional image in the streak camera 104. As a result, the two-dimensional image expressed in coordinates of which ordinate axis indicates time and of which abscissa axis indicates a wavelength, in which a luminous point indicates a luminous intensity, can be obtained. If the two-dimensional image is cut out along a predetermined time axis, emission spectrum expressed in coordinates of which ordinate axis indicates a luminous intensity and of which abscissa axis indicates the wavelength can be obtained. If the two-dimensional image is cut out along a wavelength axis, a decay curve (transient PL) expressed in coordinates of which ordinate axis indicates a logarithm of the luminous intensity and of which abscissa axis indicates time can be obtained.

An emission decay curve expressed in coordinates of which ordinate axis indicates a luminous intensity and of which abscissa axis indicates time can be obtained by measuring the transient PL as described above. Based on the emission decay curve, a fluorescence intensity ratio between fluorescence in the single state generated by light excitation and the delayed fluorescence in the singlet state generated by the inverse energy transfer through the triplet state can be estimated. In the delayed fluorescence material, a ratio of the delayed fluorescence intensity to be gradually reduced is larger to some extent than a ratio of the fluorescence intensity to be rapidly reduced.

In the first exemplary embodiment, an amount of the delayed fluorescence can be calculated using the device of FIG. 2. In the first compound after excited with pulse light (light irradiated from the pulse laser) having a wavelength to be absorbed in the first compound, Prompt Emission that is immediately observed in the excited state and Delay Emission that is not observed immediately after the excitation but is later observed are present. In the first exemplary embodiment, an amount of Delay Emission is preferably 5% or more based on an amount of Prompt Emission.

The amount of Prompt Emission and the amount of Delay Emission can be obtained according to the method as a method described in "Nature 492, 234-238, 2012." The amount of Prompt emission and the amount of Delay emission may be calculated using a device different from one described in the above Reference Literature.

A sample usable for measuring delayed fluorescence is obtained, for instance, by co-depositing the first compound and a compound TH-2 described later on a quartz substrate so that a ratio of the first compound is 12 mass %, thereby forming a 100-nm-thick thin film.

The first compound in the exemplary embodiment is a delayed fluorescent compound and an emission color thereof is not particularly limited. For instance, the first compound preferably emits light having a main peak wavelength from 500 nm or less, more preferably 480 nm or less. On the other hand, the first compound also preferably emits light having a main peak wavelength exceeding 550 nm. The main peak wavelength means a peak wavelength of luminescence spectrum exhibiting a maximum luminous intensity among luminous spectra measured in a toluene solution in which a measurement target compound is dissolved at a concentration from $10^{-5}$ mol/l to $10^{-6}$ mol/l.

ΔST

In the exemplary embodiment, a difference ΔST(M1) between the singlet energy S(M1) of the first compound and the energy gap $T_{77K}$(M1) at 77 [K] of the first compound preferably satisfies a relationship of a numerical formula (Numerical Formula 1) below. In the exemplary embodiment, a difference between the singlet energy S and the energy gap $T_{77K}$ is defined as ΔST.

$$\Delta ST(M1)=S(M1)-T_{77K}(M1)<0.3[eV] \quad \text{(Numerical Formula 1)}$$

ΔST(M1) is preferably less than 0.2 [eV].

From quantum chemical viewpoint, a decrease in the energy difference (ΔST) between the singlet energy S and the triplet energy T can be achieved by a small exchange interaction therebetween. Physical details of the relationship between ΔST and the exchange interaction are exemplarily described in Reference Documents 1 and 2 below:

Reference Document 1: Organic EL Symposium, proceeding for the tenth meeting edited by Chihaya Adachi et al., S2-5, p11-12; and Reference Document 2: Organic Photochemical Reaction Theory edited by Katsumi Tokumaru, Tokyo Kagaku Dojin Co., Ltd. (1973).

Such a material can be synthesized according to molecular design based on quantum calculation. Specifically, the material is a compound in which a LUMO electron orbit and a HOMO electron orbit are localized to avoid overlapping.

Examples of the compound having a small ΔST used as the first compound of the exemplary embodiment include compounds in which a donor element is bonded to an acceptor element in a molecule and ΔST is in a range of 0 eV or more and less than 0.3 eV in view of electrochemical stability (oxidation-reduction stability).

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that ΔST can be further reduced by the interaction of the molecules. In such a case, ΔST can be extremely small in a range from 0 eV to 0.2 eV.

Relationship Between Triplet Energy and Energy Gap at 77K

Description will be made on a relationship between a triplet energy and an energy gap at 77K. In the exemplary embodiment, the energy gap at 77 [K] is different from a typical triplet energy in some aspects.

For the first compound (measurement target), the triplet energy is measured as follows. A measurement target compound (the first compound) and a compound TH-2 are co-deposited on a quartz substrate to prepare a sample sealed in an NMR tube. The samples were prepared under the following conditions.

quartz substrate/TH-2: first compound (film thickness: 100 nm, concentration of first compound: 12 mass %).

[Formula 15]

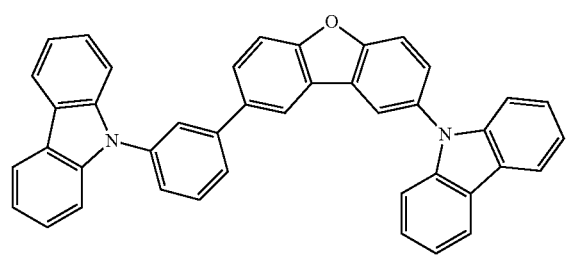

TH-2

A phosphorescent spectrum (ordinate axis: phosphorescent luminous intensity, abscissa axis: wavelength) of each of the samples was measured at a low temperature (77K). A tangent was drawn to the rise of the phosphorescent spectrum on the short-wavelength side. An energy amount was calculated as the energy gap $T_{77K}$ at 77K according to a conversion equation 1 below based on a wavelength value $\lambda_{edge}$ (nm) at an intersection of the tangent and the abscissa axis.

$T_{77K}$ [eV]=1239.85/$\lambda_{edge}$    Conversion Equation 1:

For phosphorescence measurement, a spectrophotofluorometer body F-4500 (manufactured by Hitachi High-Technologies Corporation) was used. It should be noted that the phosphorescence measuring device may be different from the above device.

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent was increased as the curve rose (i.e., a value of the ordinate axis was increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being the closest to the short-wavelength side and having the maximum inclination is defined as a tangent to the rise of the phosphorescence spectrum on the short-wavelength side.

The first compound used in the exemplary embodiment is preferably a compound having a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state, and it is difficult to distinguish the emission derived from the singlet state from the emission derived from the triplet state. However, the value of the triplet energy is basically considered dominant Accordingly, in the exemplary embodiment, the triplet energy is measured by the same method as a typical triplet energy T, but a value measured in the above manner is referred to as an energy gap $T_{77K}$ in order to differentiate the measured energy from the typical triplet energy in a strict meaning.

Singlet Energy S

Singlet energy S is measured as follows.

A 10-μmol/L toluene solution of a compound (measurement target) was prepared and put in a quartz cell. An absorption spectrum (ordinate axis: luminous intensity, abscissa axis: wavelength) of the sample was measured at a normal temperature (300K). A tangent was drawn to the fall of the absorption spectrum on the long-wavelength side, and a wavelength value $\lambda_{edge}$ (nm) at an intersection of the tangent and the abscissa axis was obtained.

$S$ [eV]=1239.85/$\lambda_{edge}$    Conversion Equation 2:

In Example, the absorption spectrum was measured using a spectrophotometer manufactured by Hitachi, Ltd. (device name: U3310). It should be noted that the absorption spectrum measuring device may be different from the above device.

The tangent to the fall of the absorption spectrum on the long-wavelength side is drawn as follows. While moving on a curve of the absorption spectrum from the maximum spectral value closest to the long-wavelength side in a long-wavelength direction, a tangent at each point on the curve was checked. An inclination of the tangent was decreased and increased in a repeated manner as the curve fell (i.e., a value of the ordinate axis was decreased). A tangent drawn at a point of the minimum inclination closest to the long-wavelength side (except when absorbance was 0.1 or less) was defined as the tangent to the fall of the absorption spectrum on the long-wavelength side.

The maximum absorbance of 0.2 or less is not included in the above-mentioned maximum absorbance on the long-wavelength side.

Method of Preparing First Compound

The first compound can be manufactured, for instance, by a method described in Example below.

Examples of the first compound according to the exemplary embodiment are shown below. It should be noted that the first compound according to the invention is not limited to these specific examples.

[Formula 16]

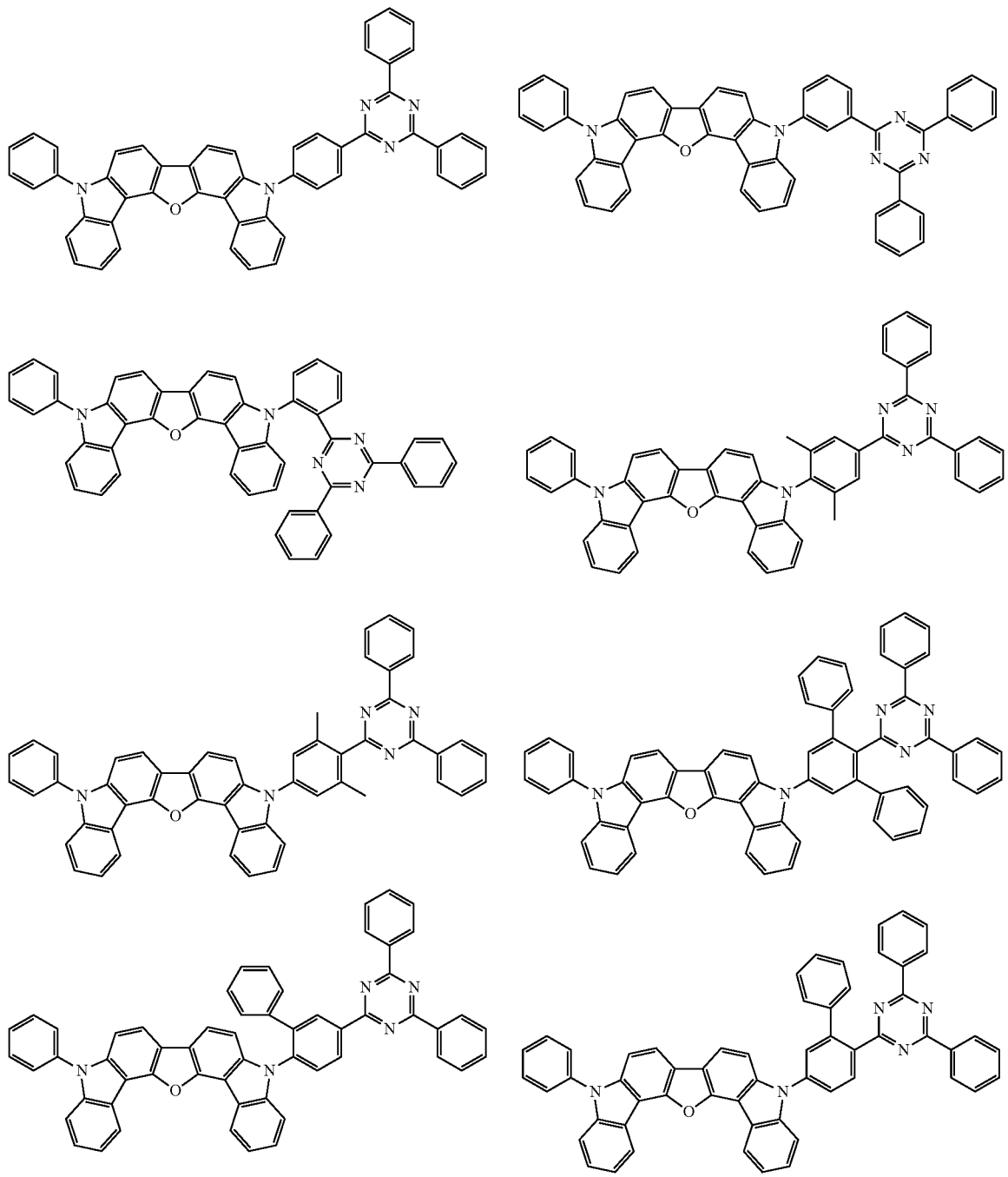

[Formula 17]
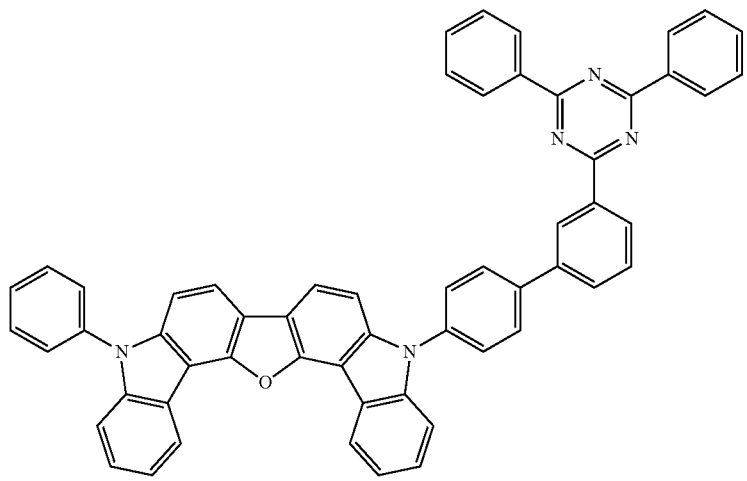
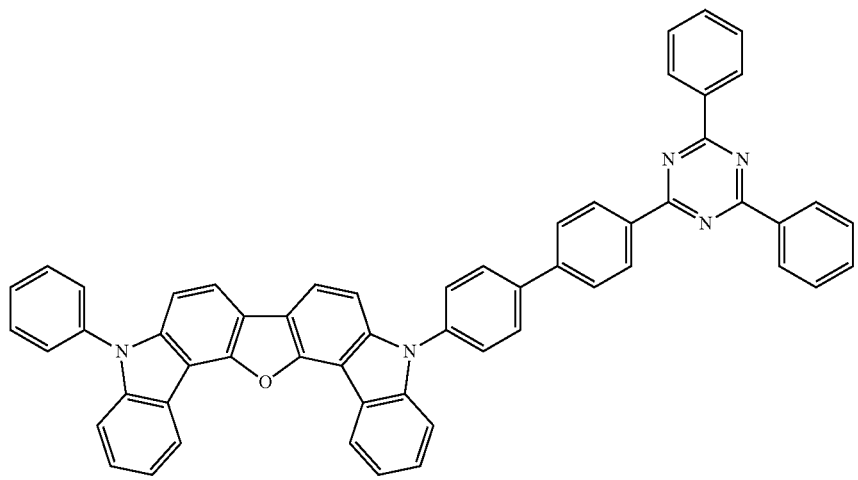
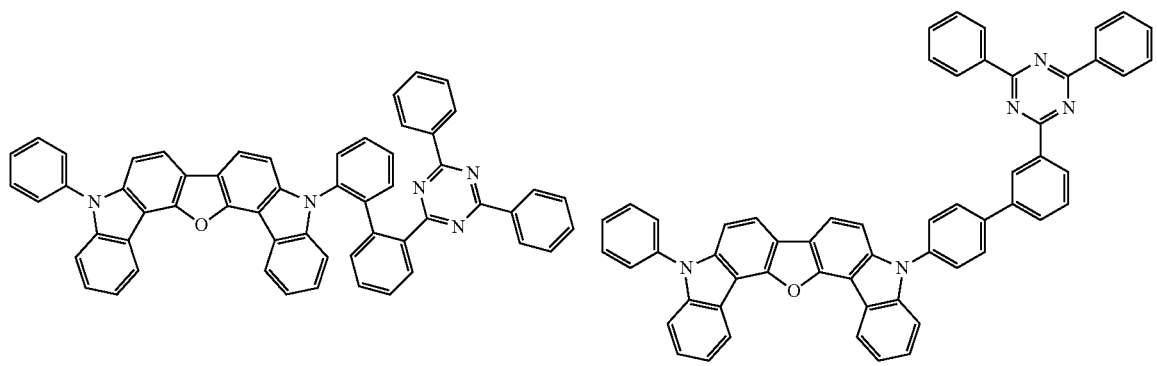

-continued
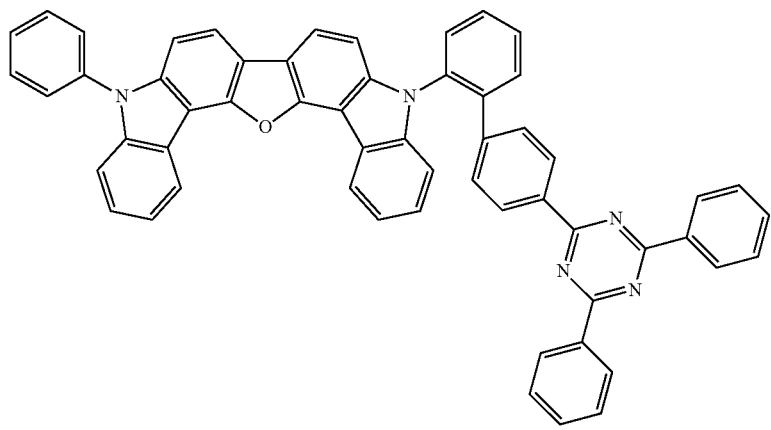
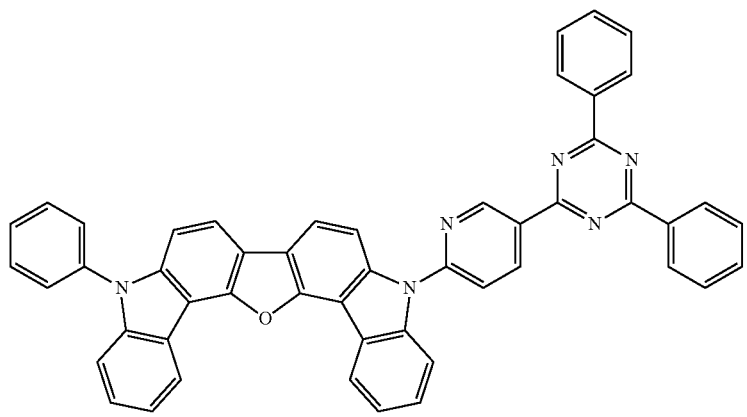
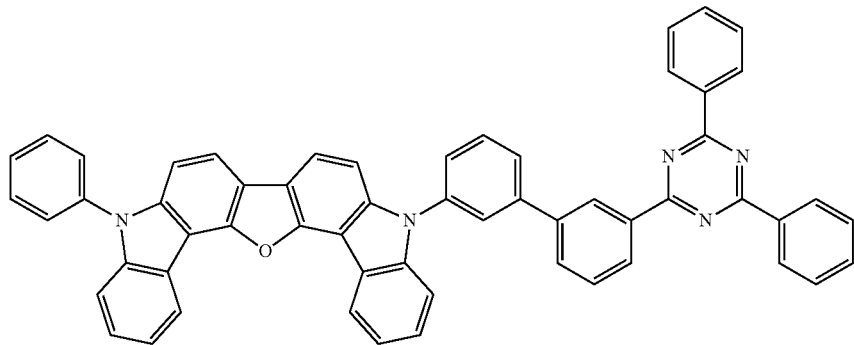
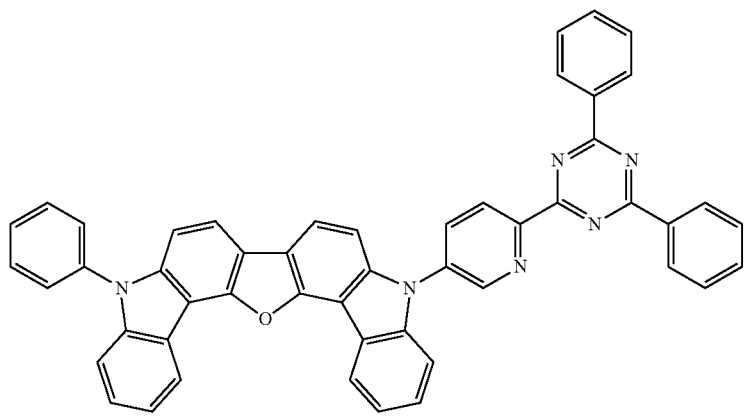

[Formula 18]
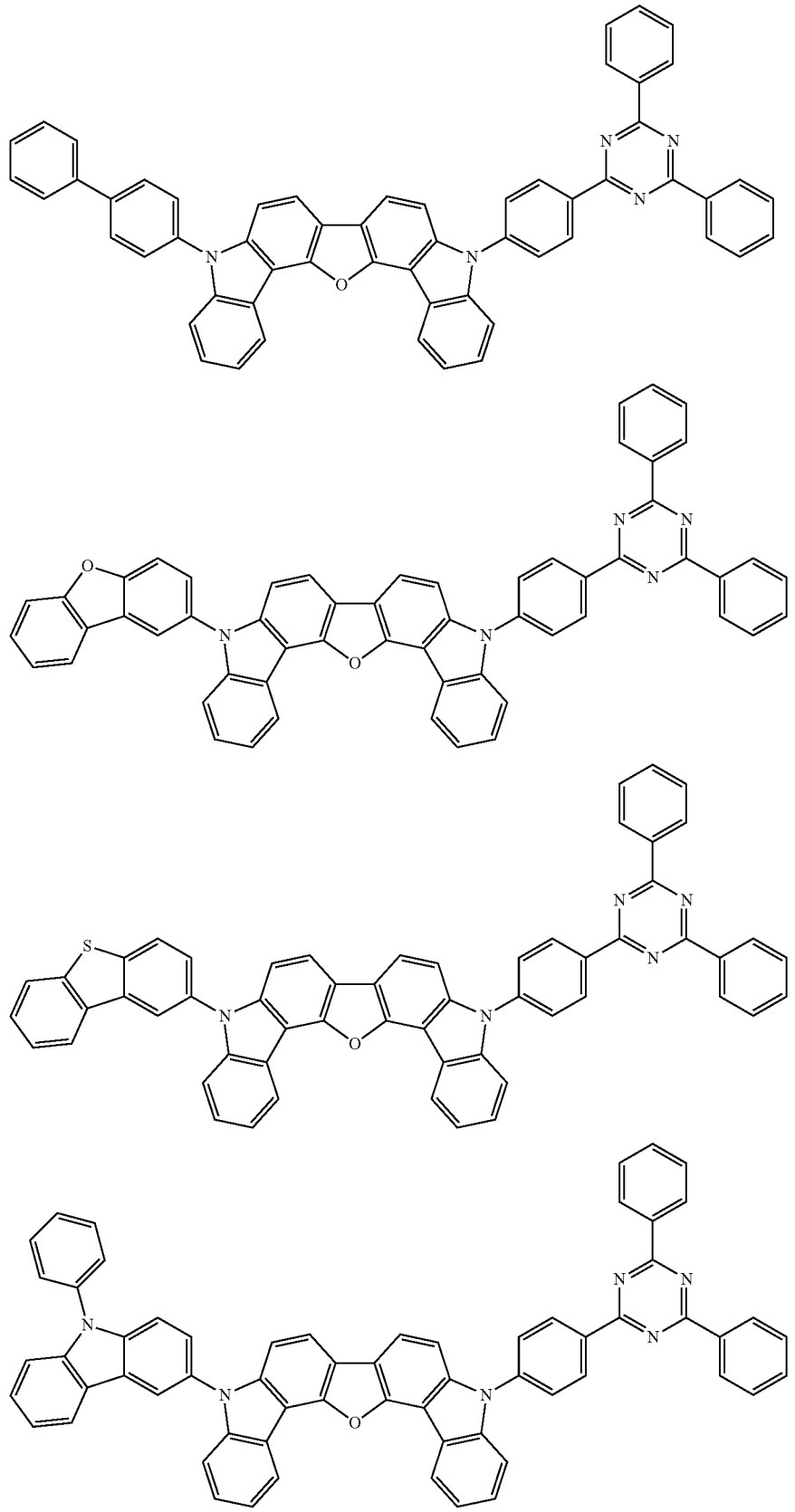

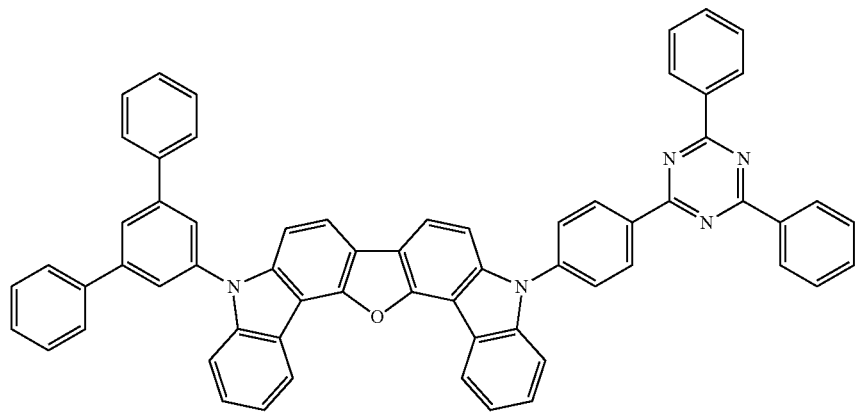
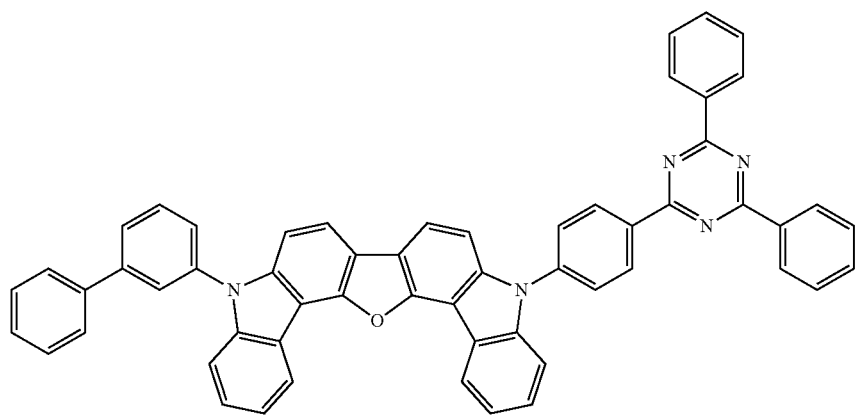
[Formula 19]
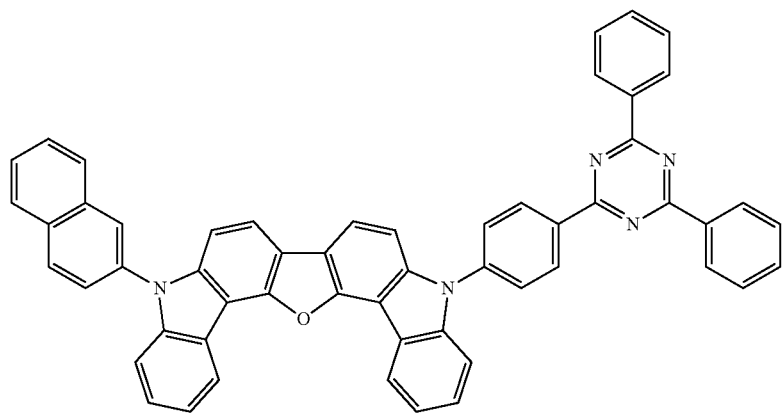
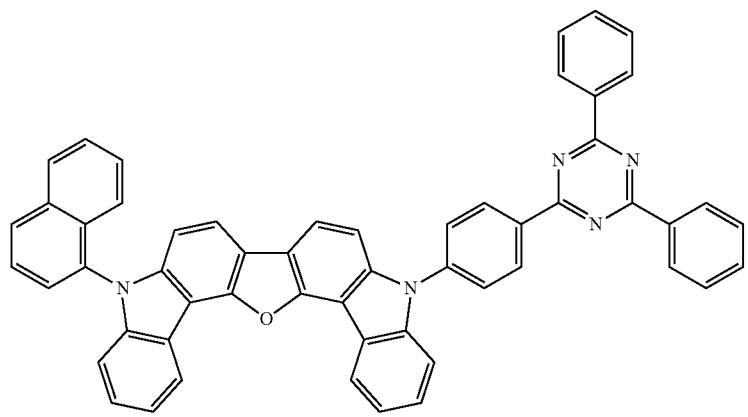

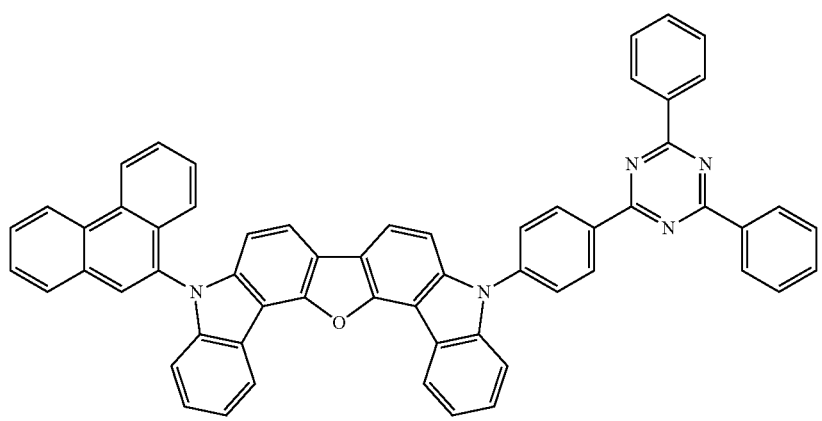
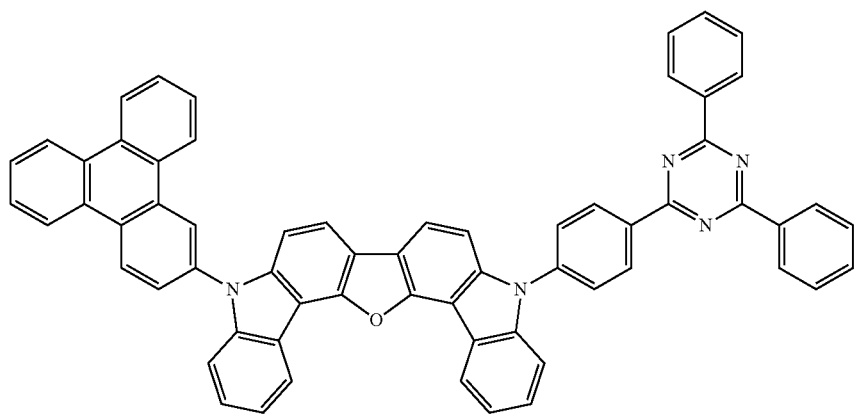
[Formula 20]
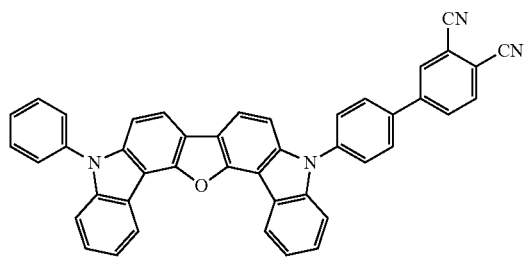
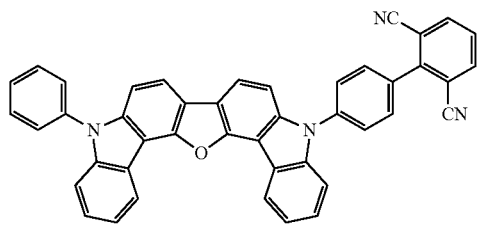
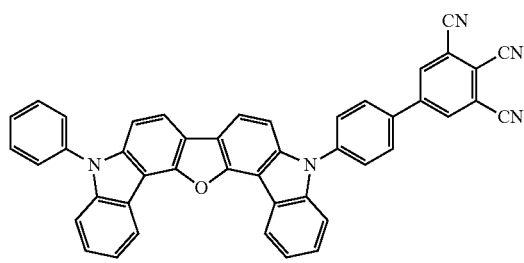
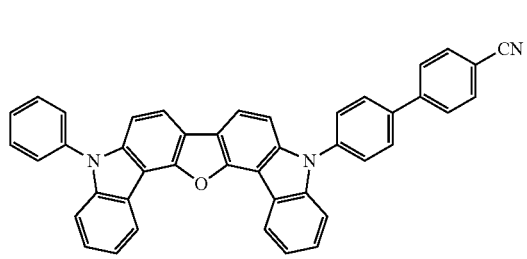
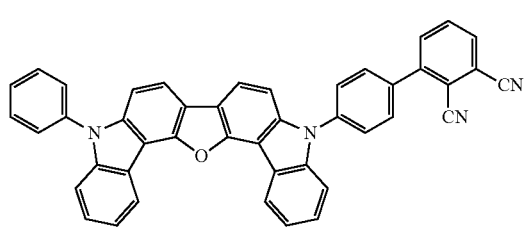
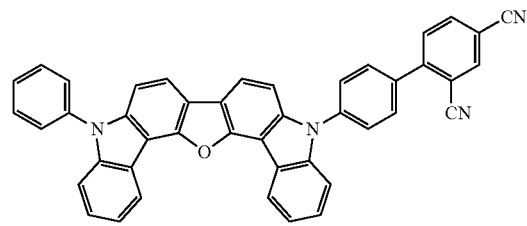

[Formula 21]
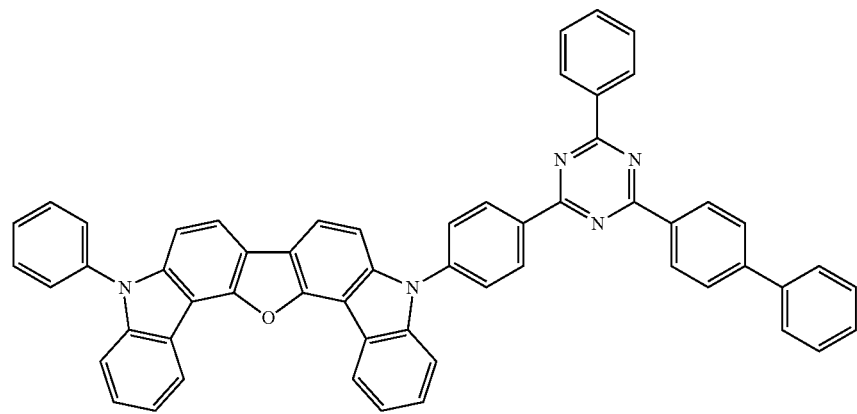
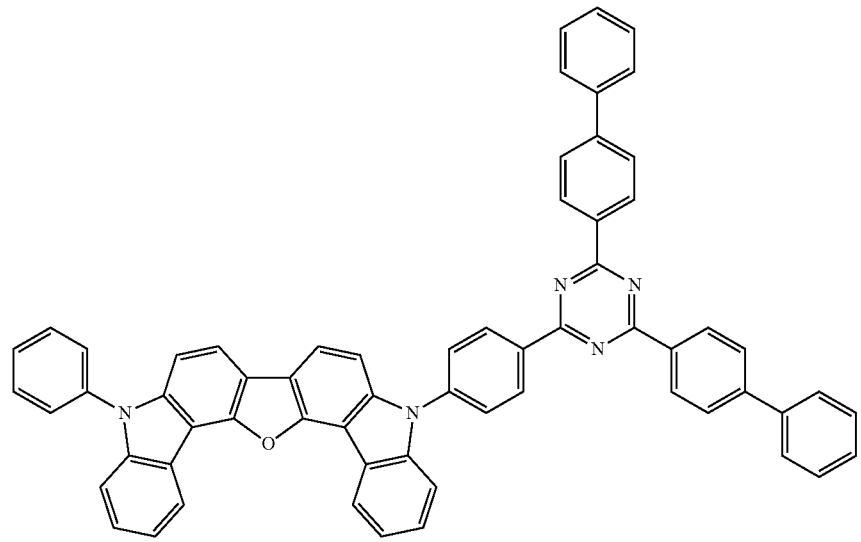
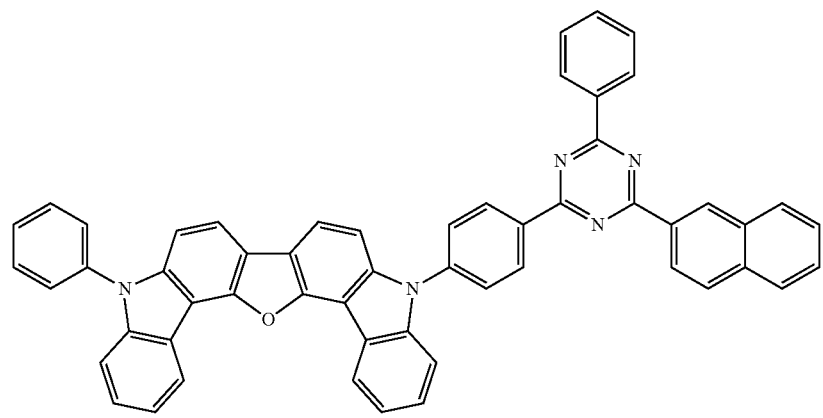

-continued
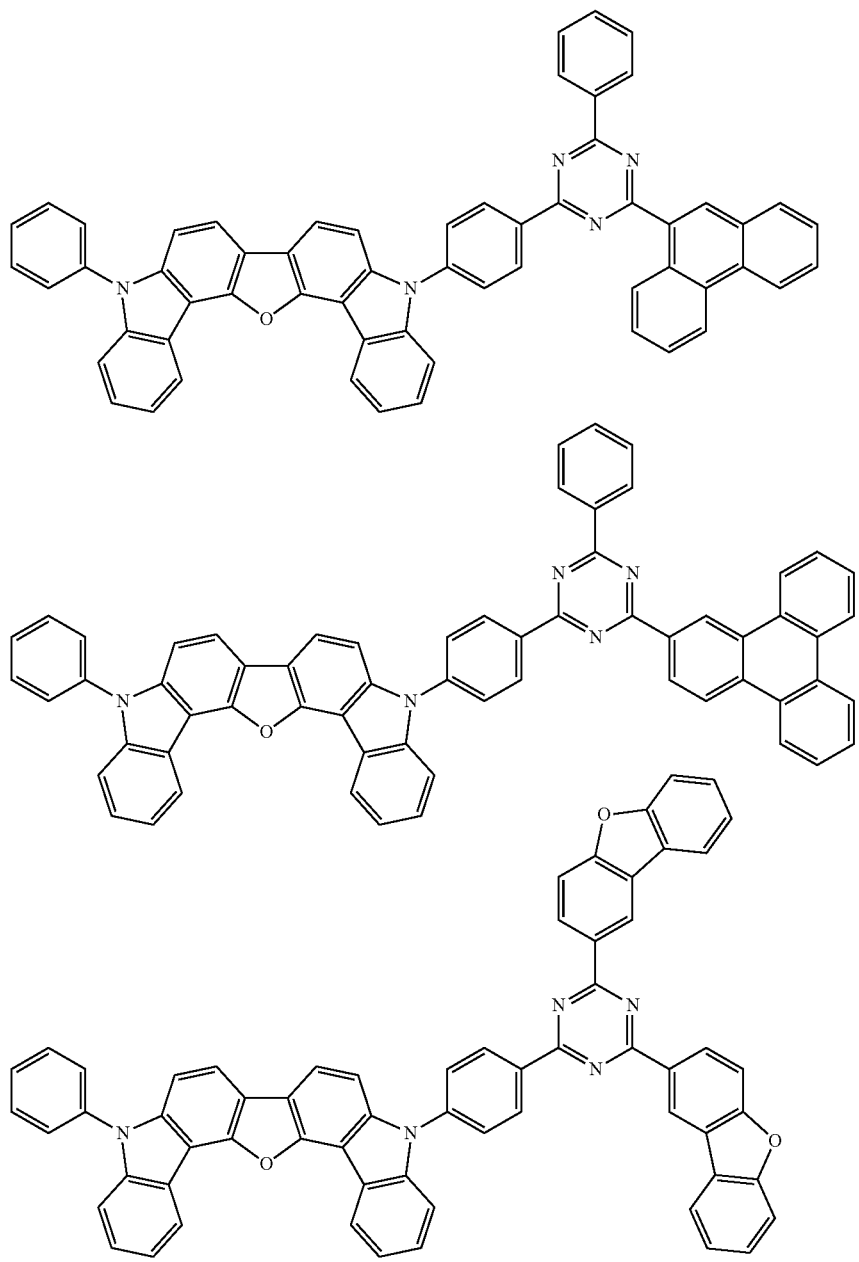
[Formula 22]
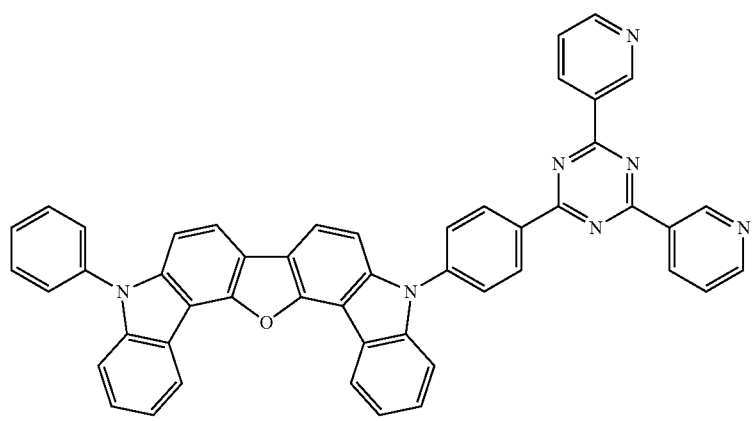

-continued
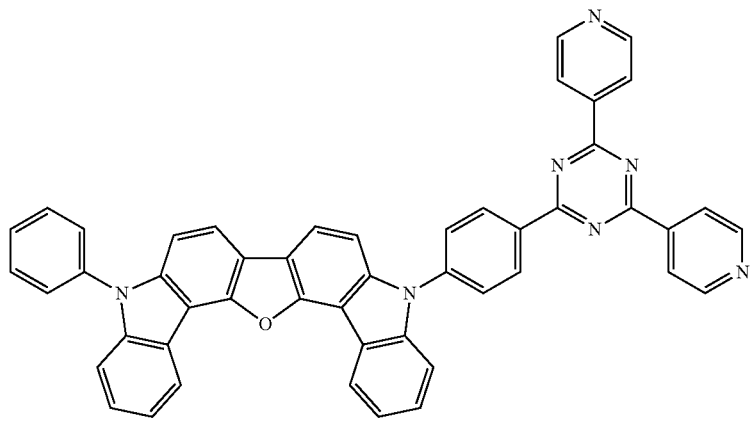
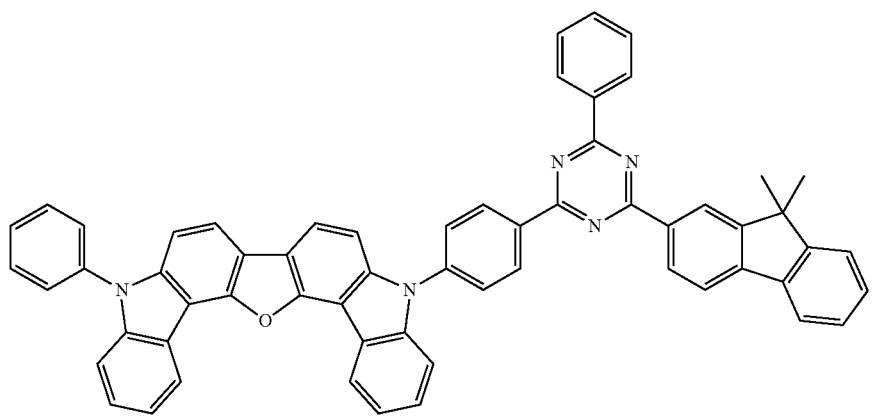
[Formula 23]
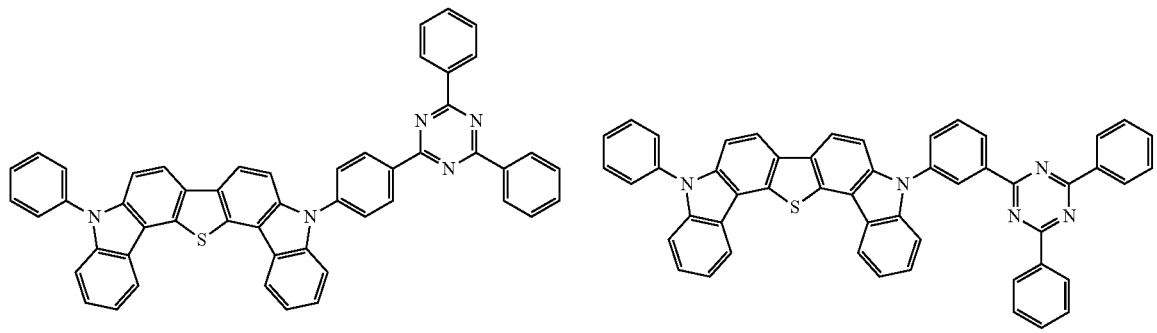
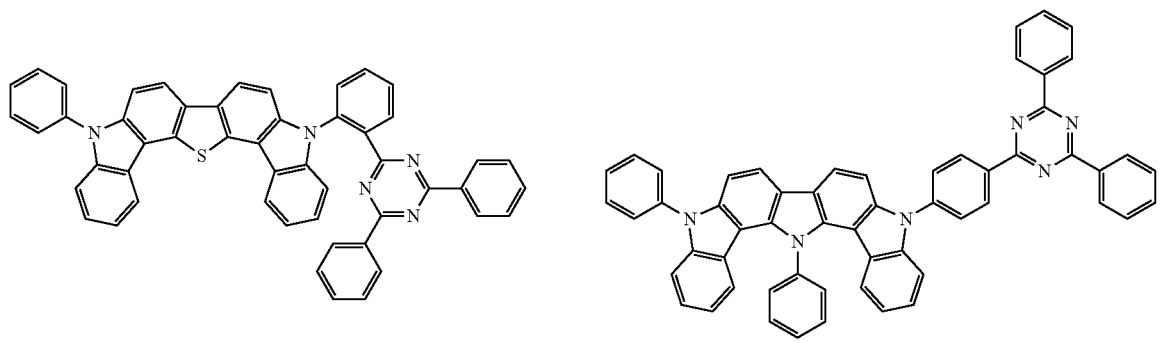

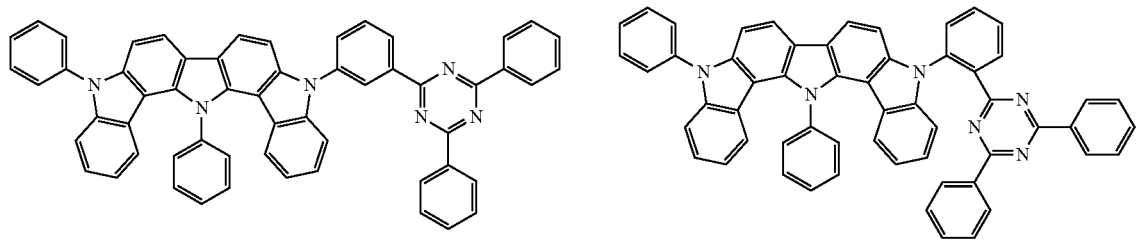
[Formula 24]
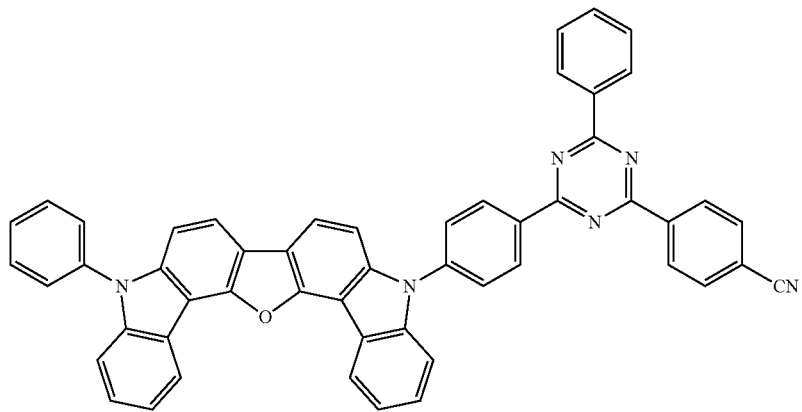
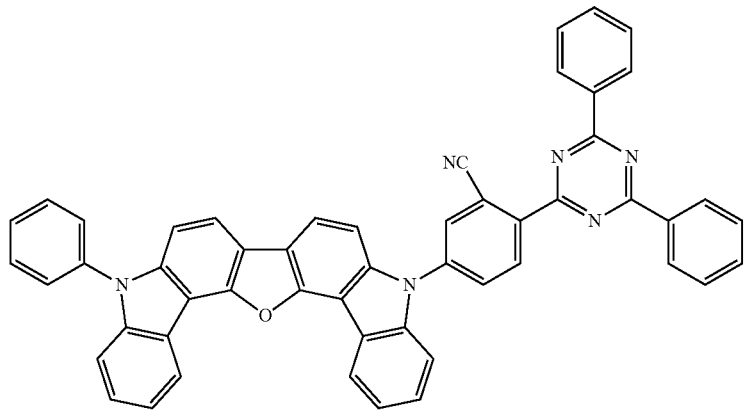
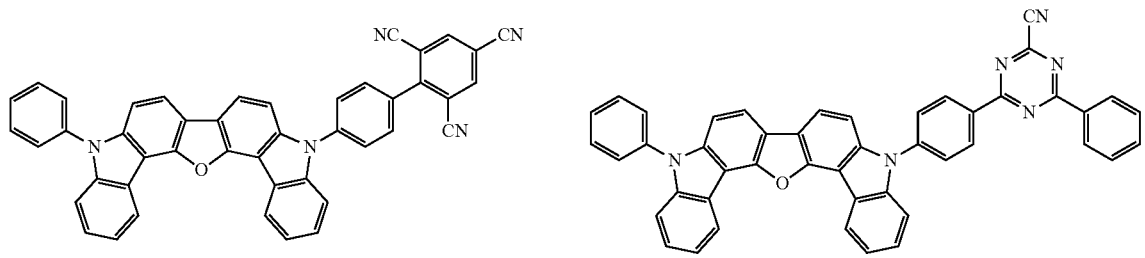

-continued
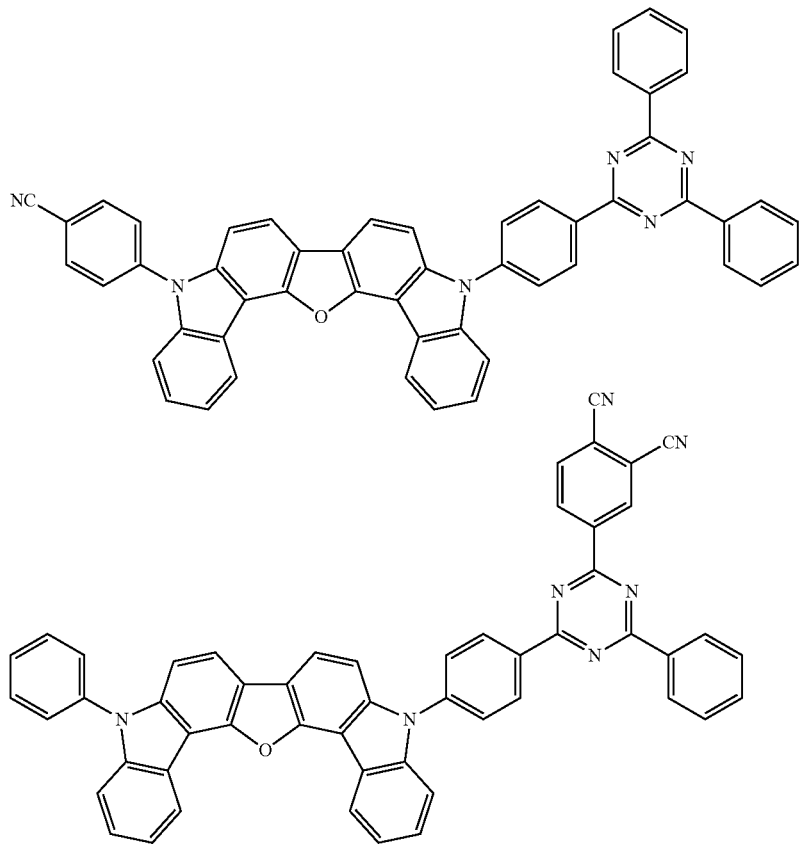
[Formula 25]
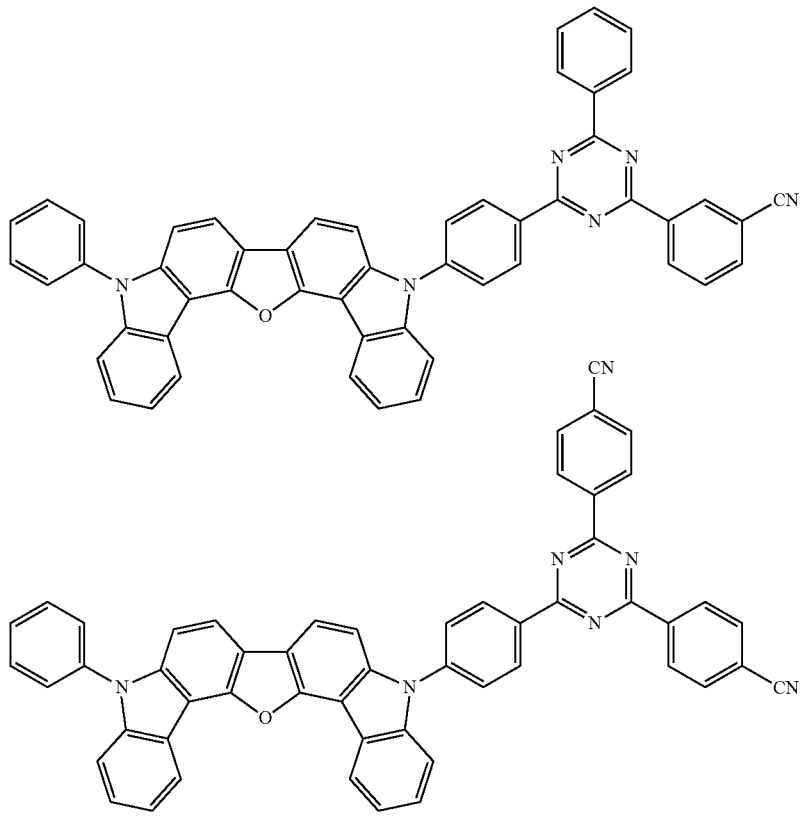

-continued
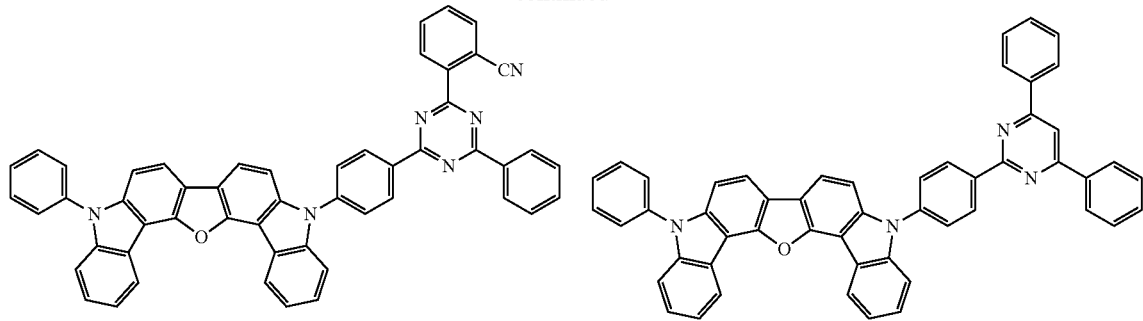
[Formula 26]
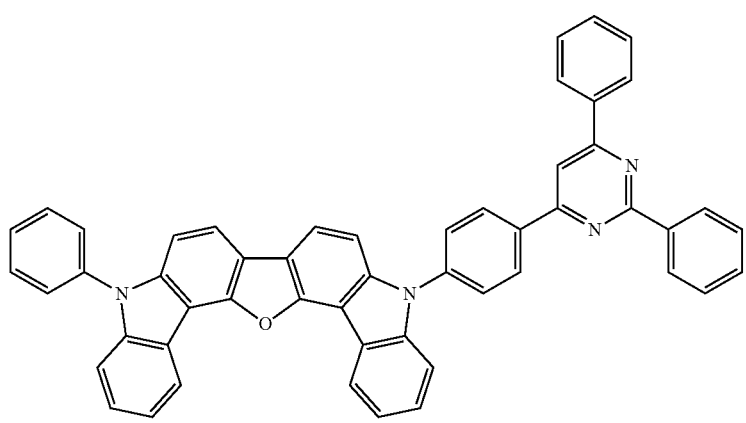
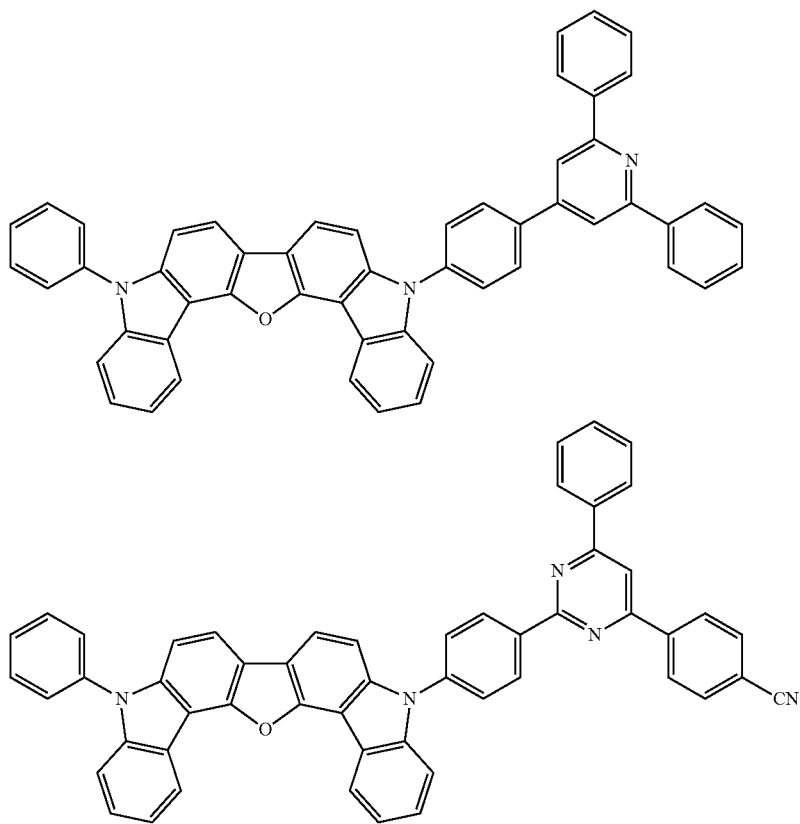

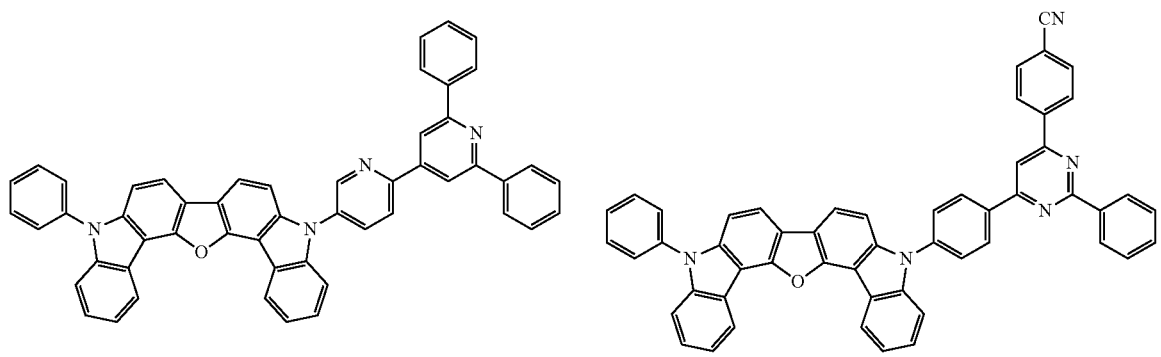
[Formula 27]
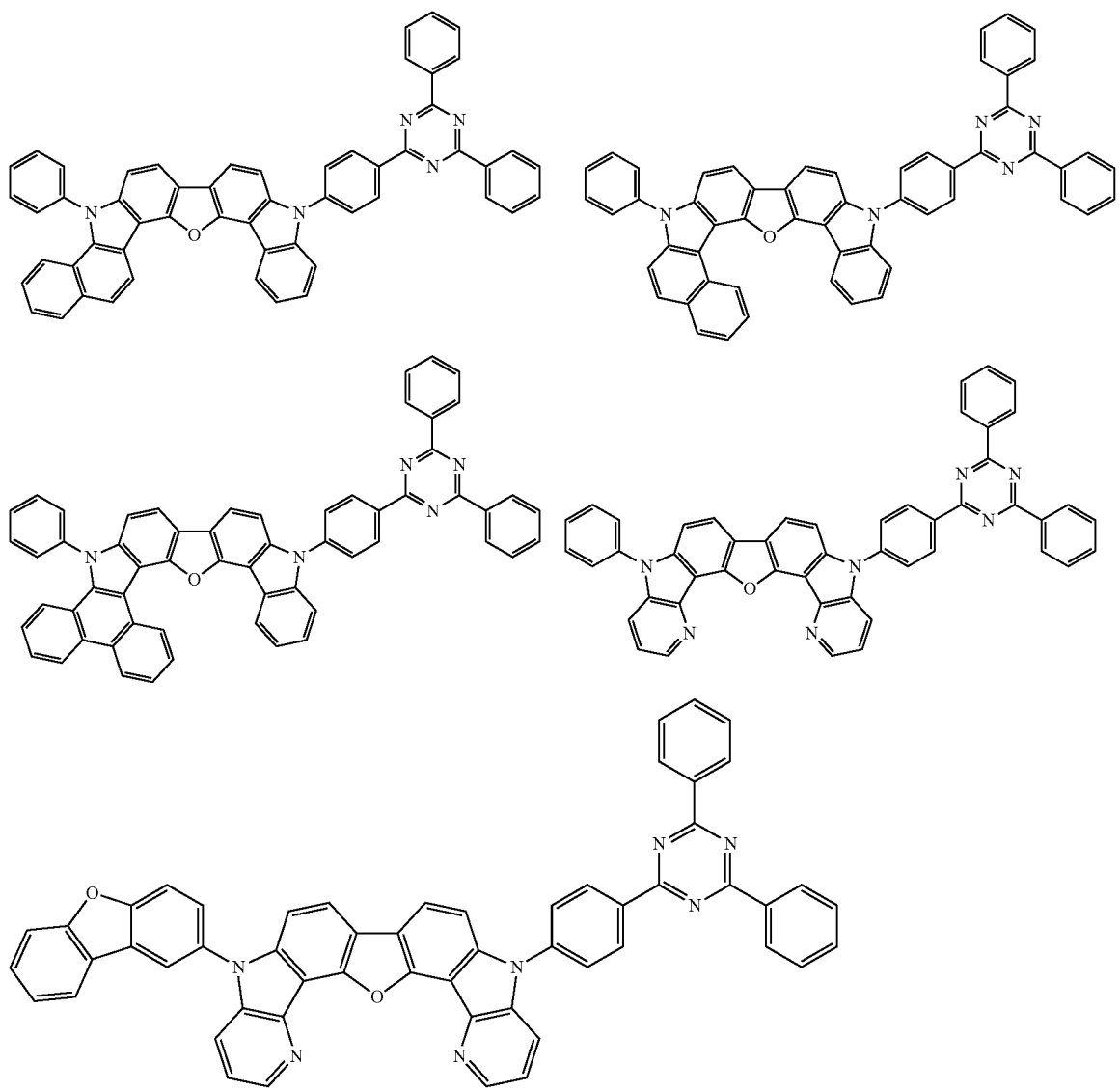

-continued
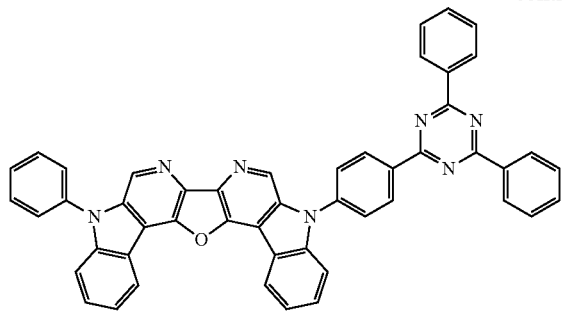
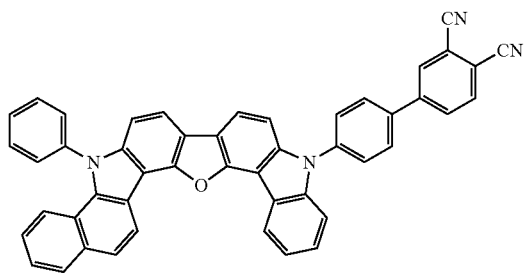
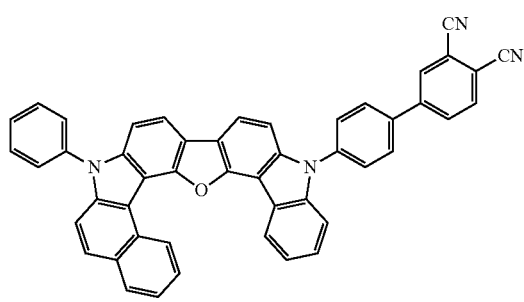
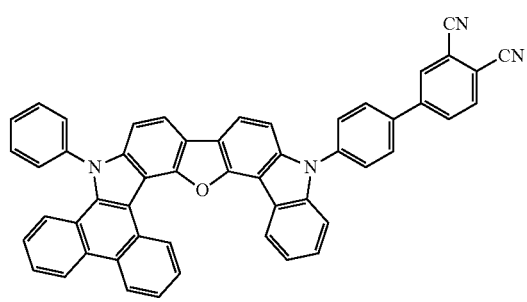
[Formula 28]
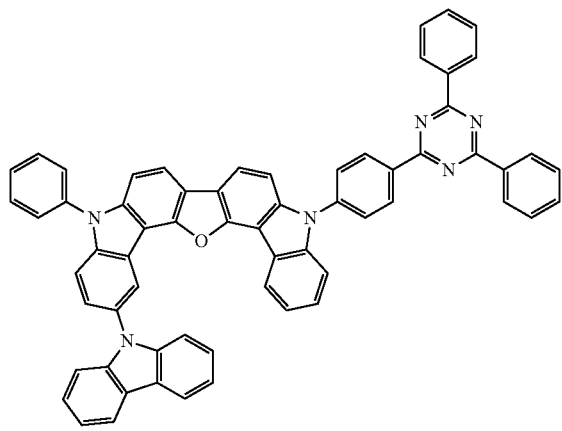
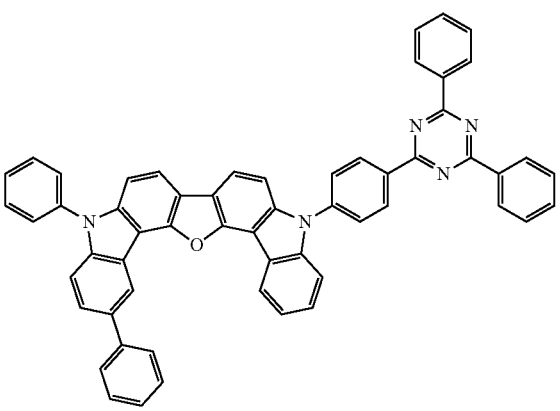
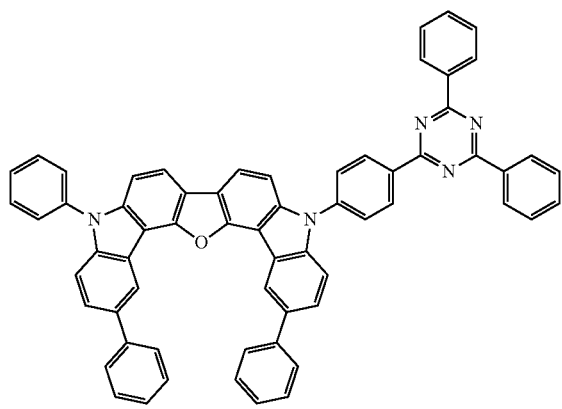
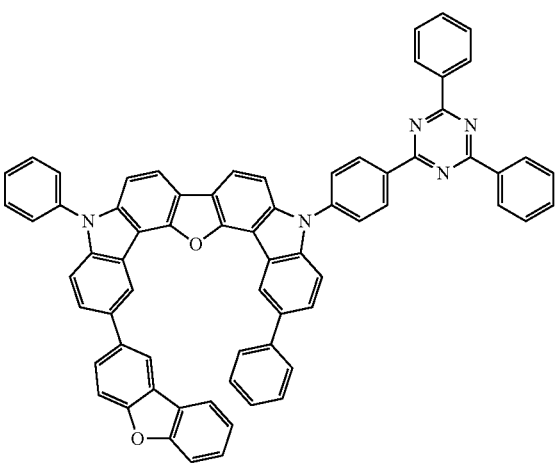

-continued
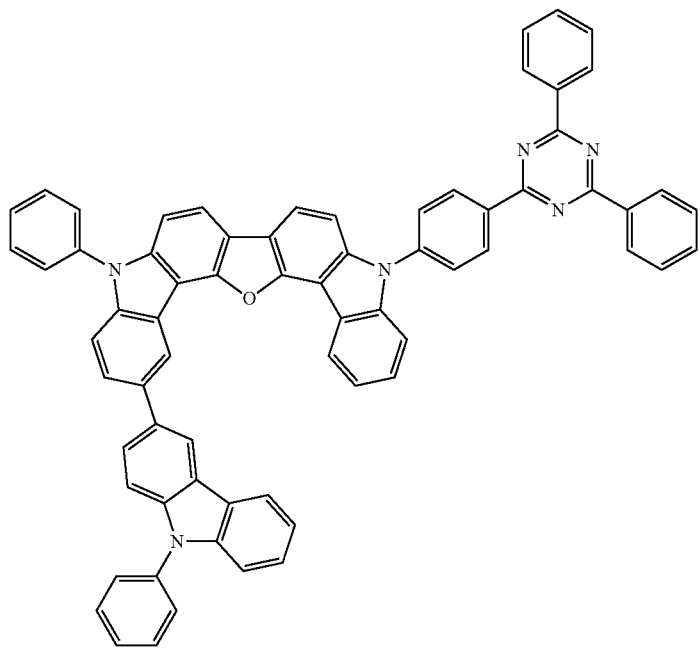
[Formula 29]
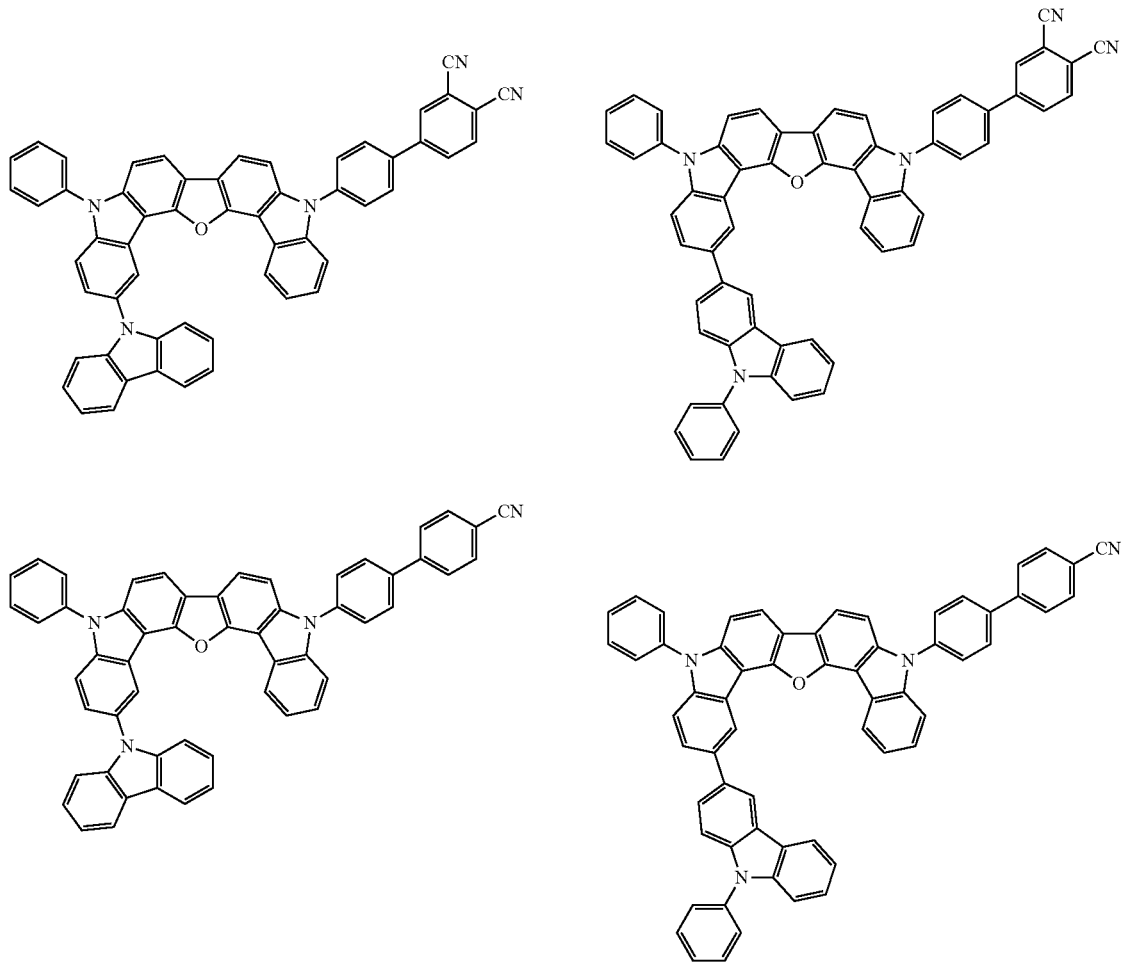

[Formula 30]
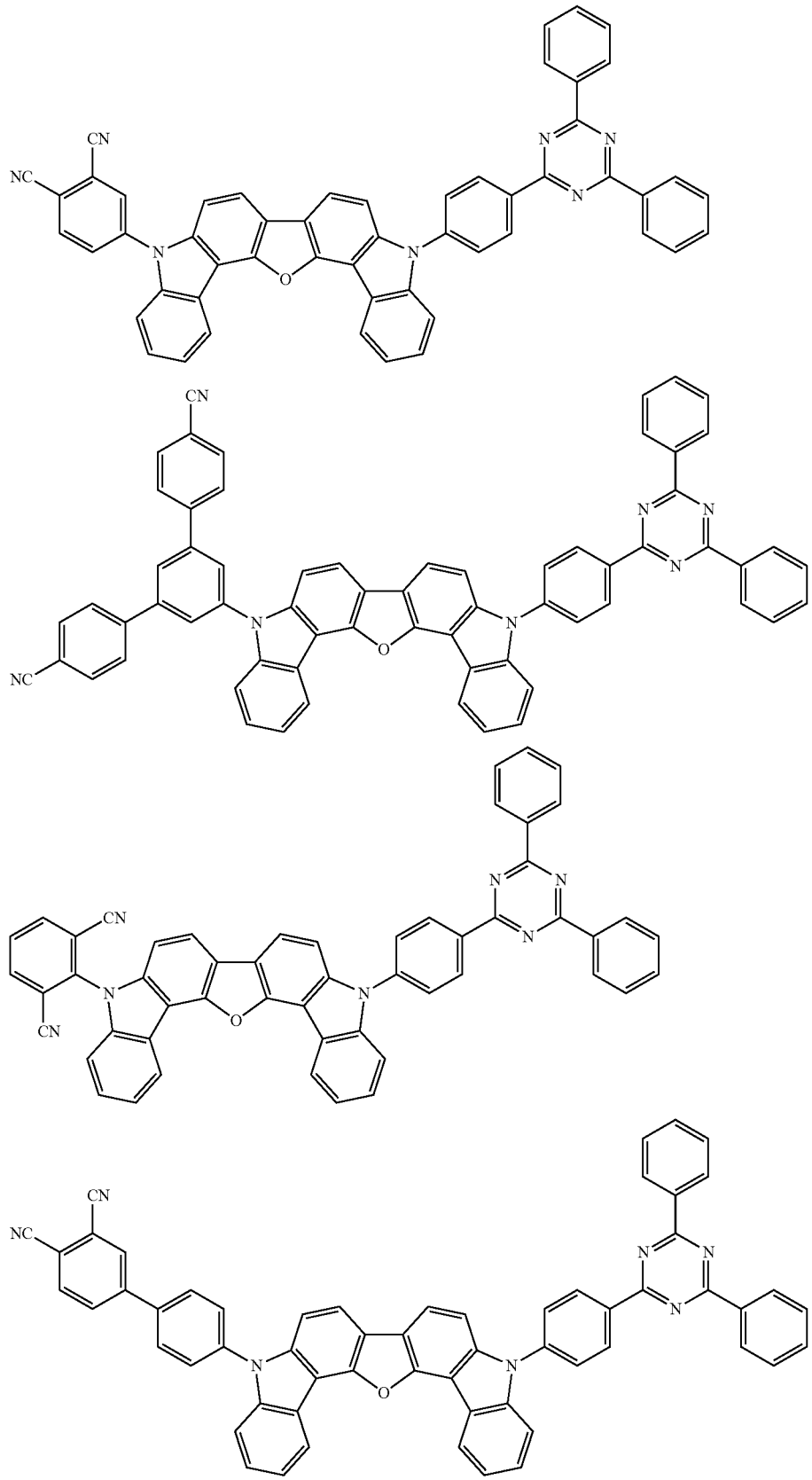

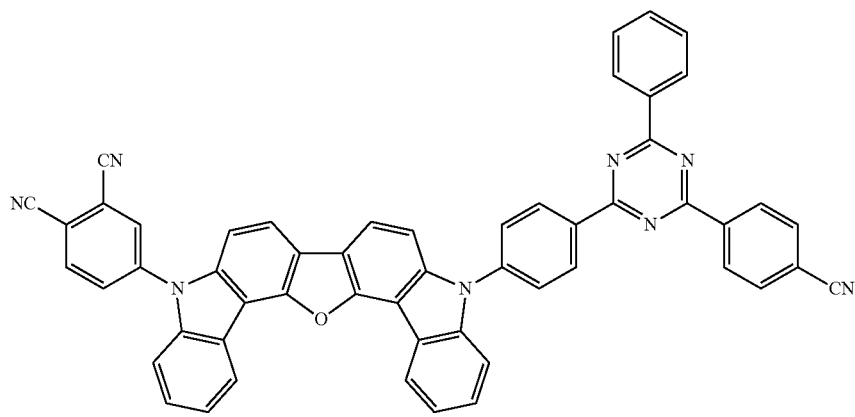
[Formula 31]
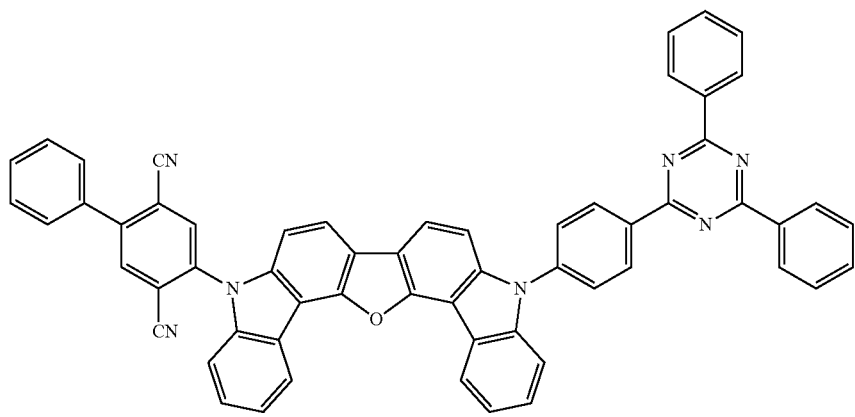
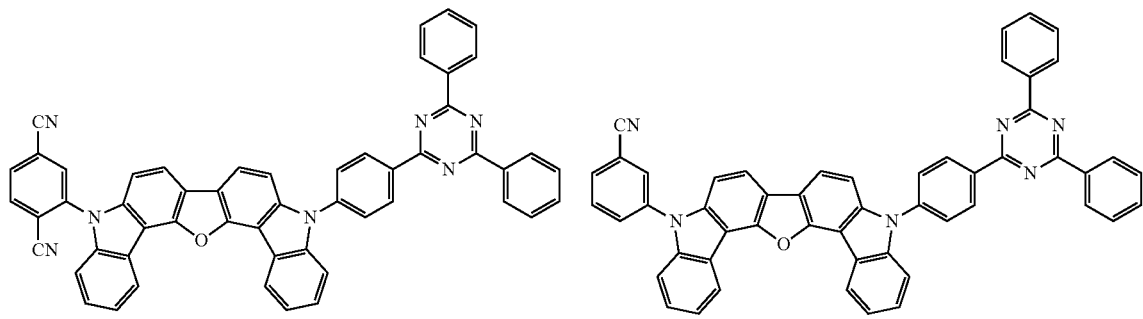
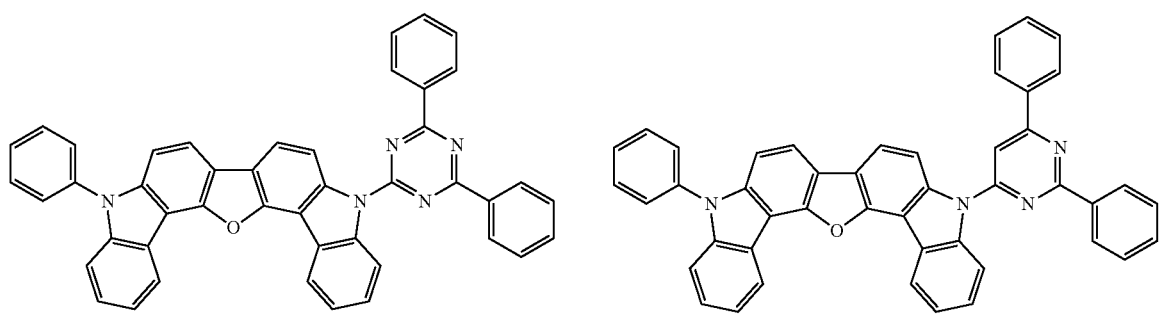

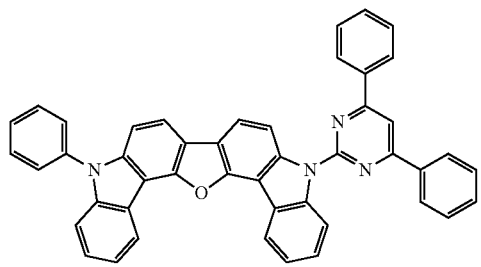
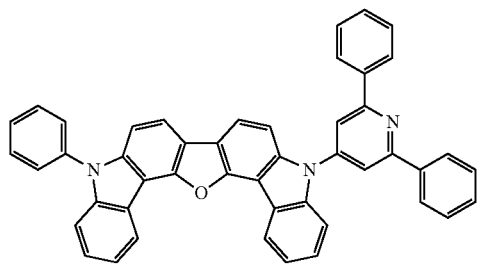
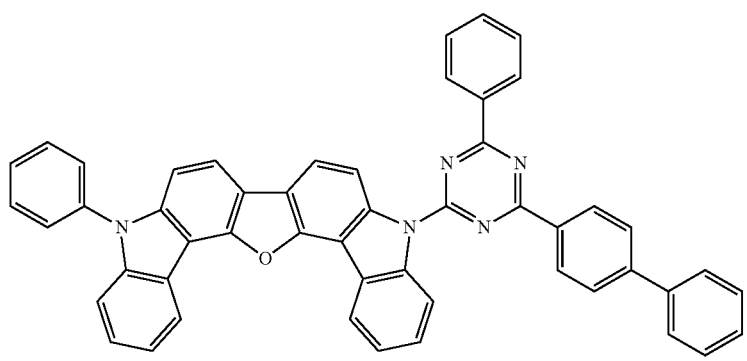
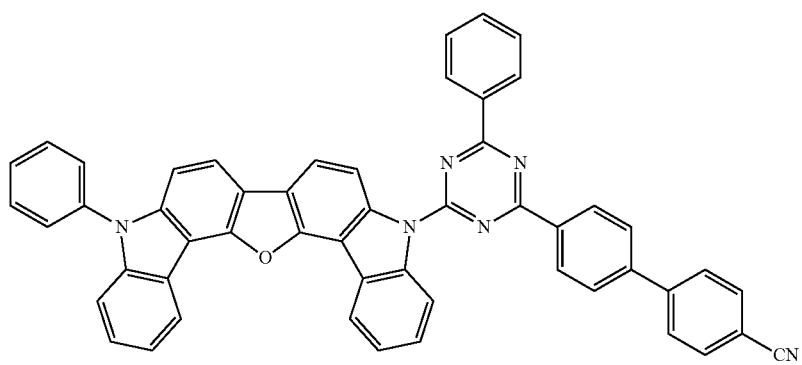
[Formula 32]
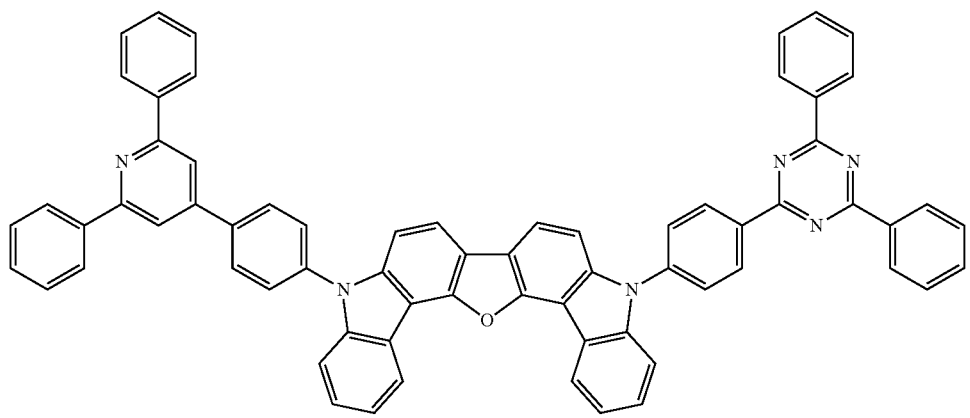

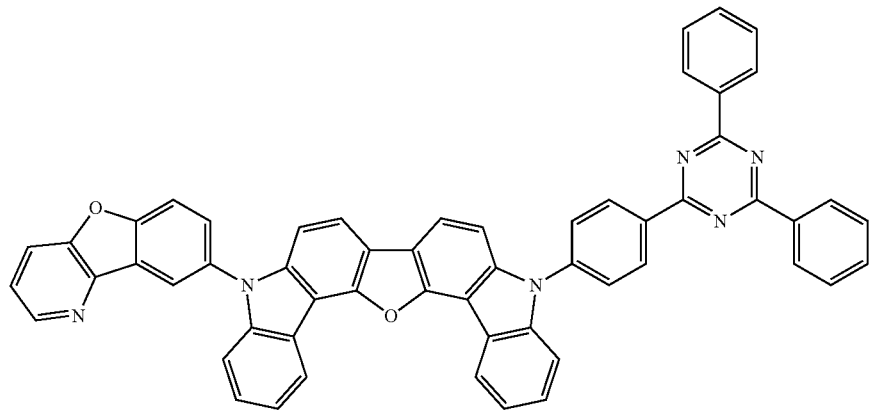
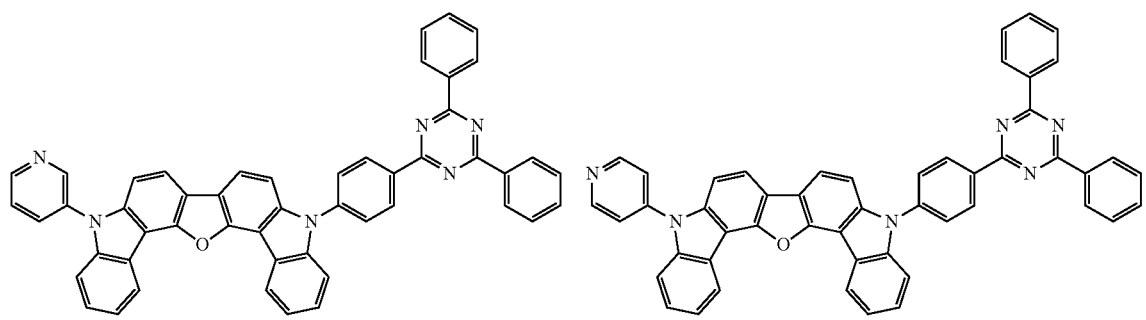
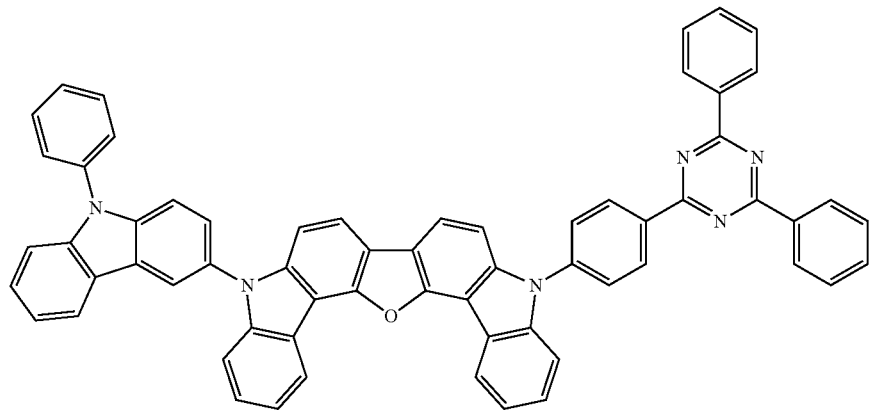
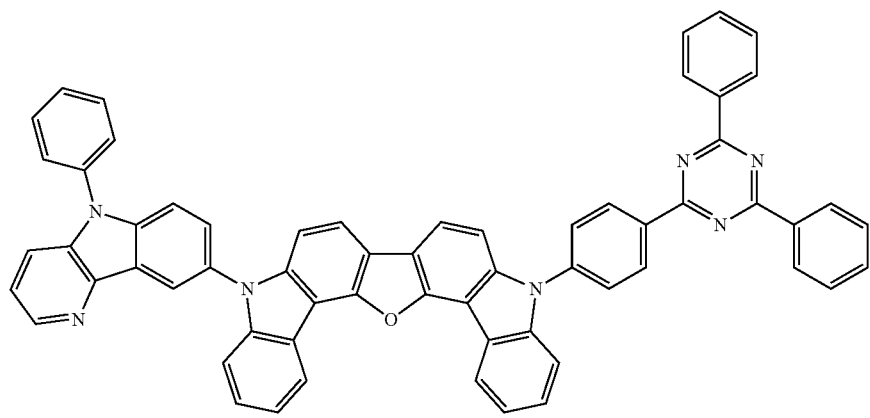

[Formula 33]
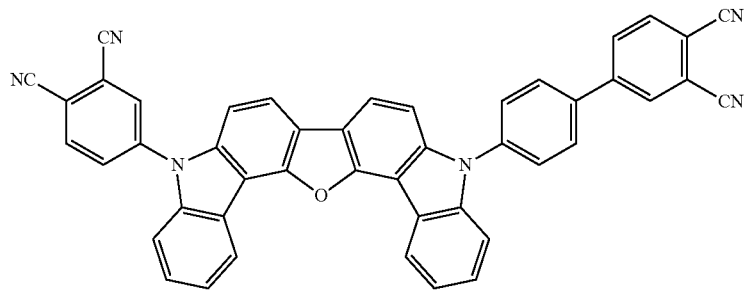
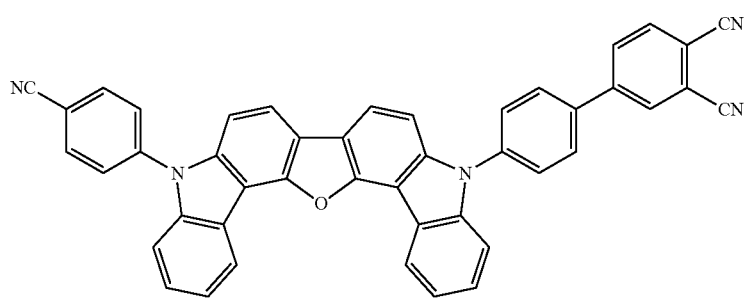
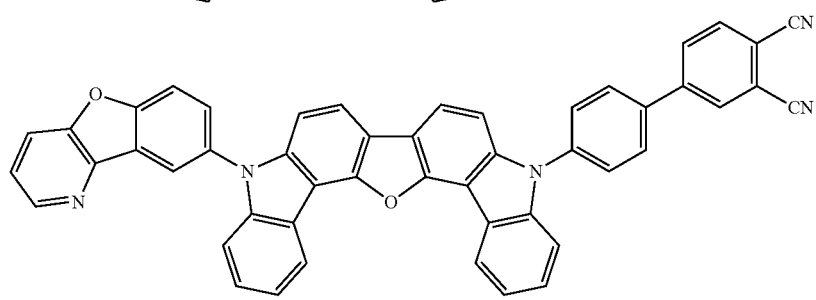
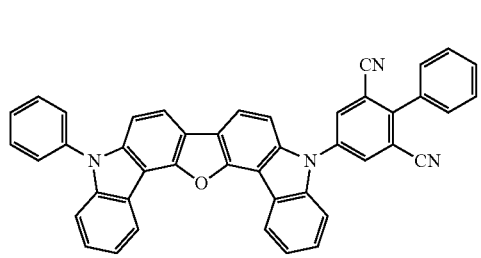
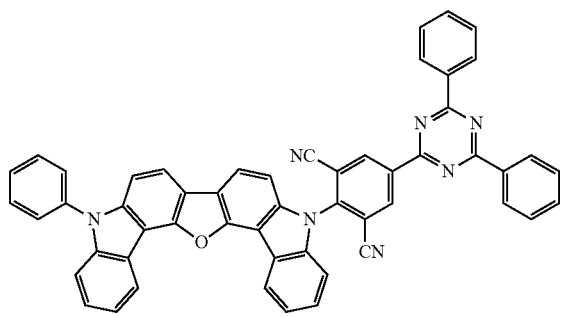
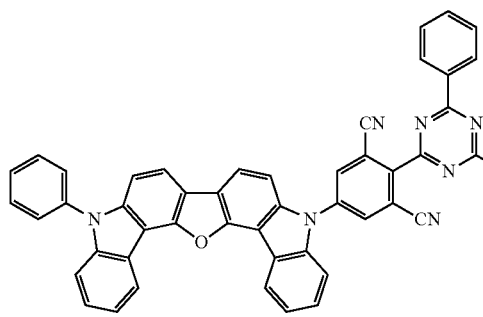
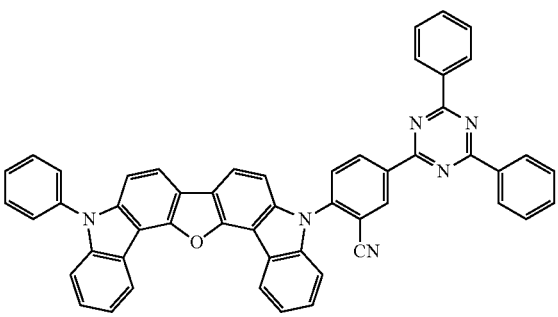

-continued

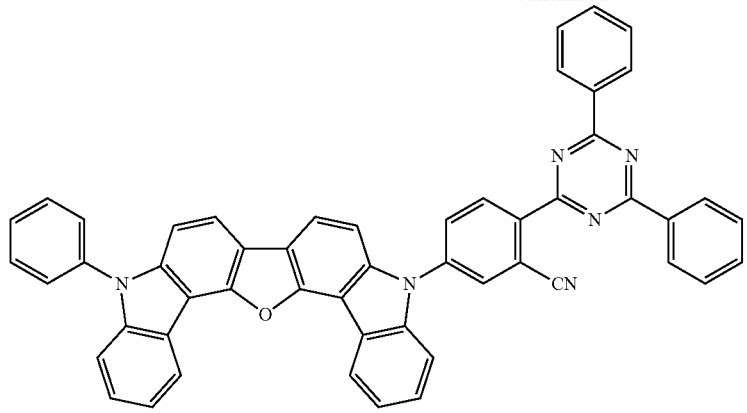

[Formula 34]

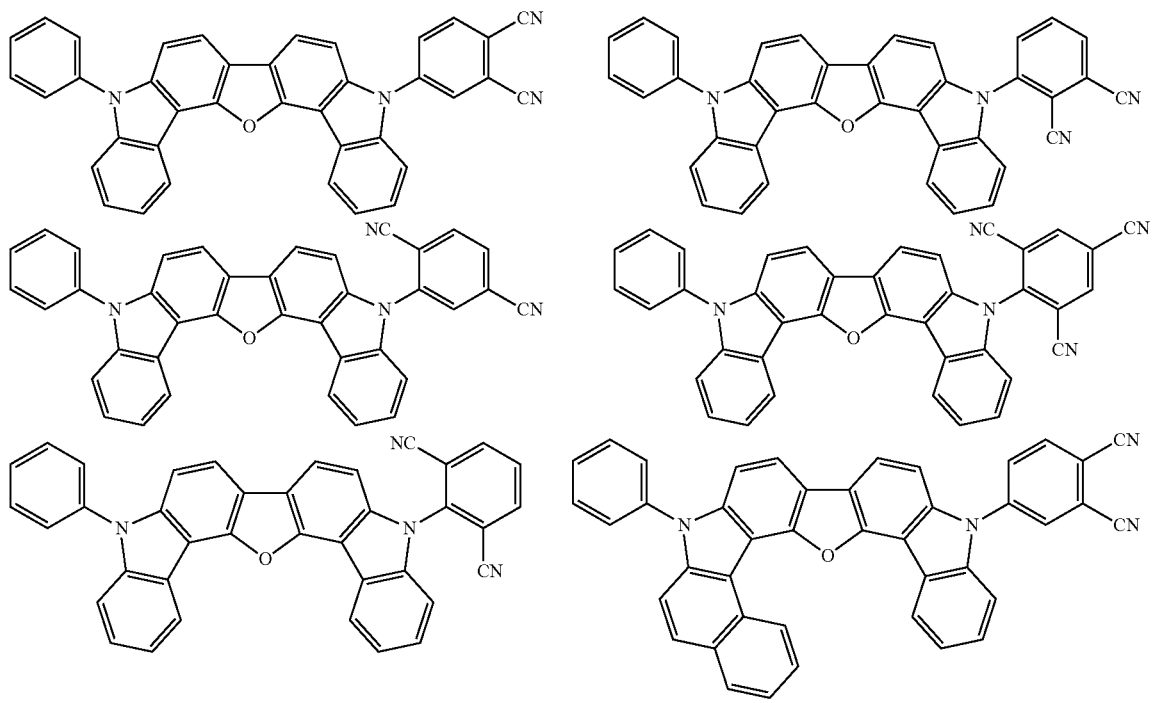

Second Compound

In the exemplary embodiment, the second compound has at least one of a partial structure represented by a formula (21) below and a partial structure represented by a formula (22) below in one molecule.

[Formula 35]

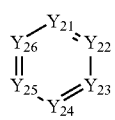
(21)

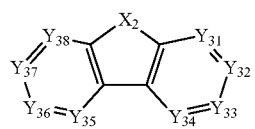
(22)

In the formula (21), $Y_{21}$ to $Y_{26}$ are each independently a nitrogen atom or a carbon atom bonded to another atom in the molecule of the second compound.

However, at least one of $Y_{21}$ to $Y_{26}$ is a carbon atom bonded to another atom in the molecule of the second compound.

In the formula (22), $Y_{31}$ to $Y_{38}$ are each independently a nitrogen atom or a carbon atom bonded to another atom in the molecule of the second compound.

However, at least one of $Y_{31}$ to $Y_{38}$ is a carbon atom bonded to another atom in the molecule of the second compound.

$X_2$ is a nitrogen atom, an oxygen atom or a sulfur atom.

In the exemplary embodiment, the partial structure represented by the formula (21) is preferably in a form of at least one group selected from the group consisting of groups represented by formulae (23) and (24) below and preferably contained in the second compound.

[Formula 36]

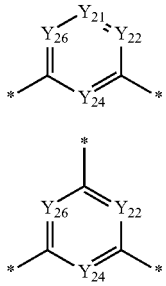

(23)

(24)

In the above formulae (23) to (24), $Y_{21}$, $Y_{22}$, $Y_{24}$ and $Y_{26}$ are each independently a nitrogen atom or $CR_{21}$.

$R_{21}$ is a hydrogen atom or a substituent;

when $R_{21}$ is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{21}$ is a non-fused ring.

Wavy lines in the formulae (23) and (24) each show a bonding position with another atom or another structure in the molecule of the second compound.

In the exemplary embodiment, $Y_{21}$, $Y_{22}$, $Y_{24}$ and $Y_{26}$ in the formula (23) are each independently $CR_{21}$. A plurality of $R_{21}$ may be the same or different.

In the exemplary embodiment, $Y_{22}$, $Y_{24}$ and $Y_{26}$ in the formula (24) are each independently $CR_{21}$. A plurality of $R_{21}$ may be the same or different.

In the exemplary embodiment, the partial structure represented by the formula (22) is preferably in a form of at least one group selected from the group consisting of the group represented by the formula (25) below, the group represented by the formula (26) below, a group represented by a formula (27) below, a group represented by a formula (28) below, a group represented by a formula (29) below and a group represented by a formula (30) below, and preferably contained in the second compound.

[Formula 37]

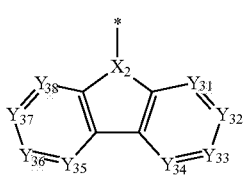

(25)

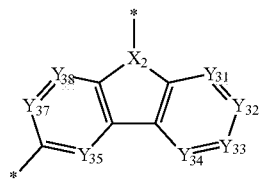

(26)

[Formula 38]

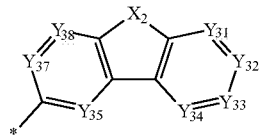

(27)

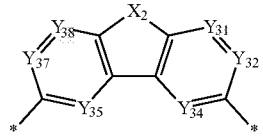

(28)

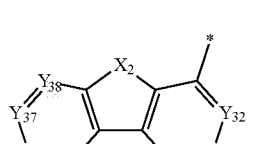

[Formula 39]

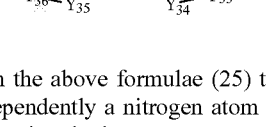

(29)

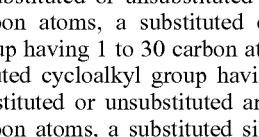

(30)

In the above formulae (25) to (30), $Y_{31}$ to $Y_{38}$ are each independently a nitrogen atom or $CR_{22}$.

$R_{22}$ is a hydrogen atom or a substituent. When $R_{22}$ is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{22}$ is a non-fused ring.

$X_2$ in the formulae (25) and (26) is a nitrogen atom.

$X_2$ in (27) to (30) is $NR_{23}$, an oxygen atom or a sulfur atom.

$R_{23}$ is a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{23}$ is a non-fused ring.

Wavy lines in the formulae (25) to (30) each show a bonding position with another atom or another structure in the molecule of the second compound.

In the exemplary embodiment: $Y_{31}$ to $Y_{38}$ in the formula (25) are preferably each independently $CR_{22}$; $Y_{31}$ to $Y_{35}$ and $Y_{37}$ in the formula (26) and the formula (27) are preferably each independently $CR_{22}$; $Y_{31}$, $Y_{32}$, $Y_{34}$, $Y_{35}$, $Y_{37}$ and $Y_{38}$ in the formula (28) are preferably each independently $CR_{22}$; $Y_{32}$ to $Y_{38}$ in the formula (29) are preferably each independently $CR_{22}$; $Y_{32}$ to $Y_{37}$ in the formula (30) are preferably each independently $CR_{22}$, and a plurality of $R_{22}$ are optionally mutually the same or different.

In the exemplary embodiment, the second compound preferably contains a group represented by a formula (20A) below.

[Formula 40]

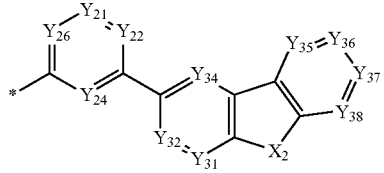

(20A)

In the formula (20A), $Y_{21}$, $Y_{22}$, $Y_{24}$ and $Y_{26}$ are each independently a nitrogen atom or $CR_{21}$.

$Y_{31}$, $Y_{32}$ and $Y_{34}$ to $Y_{38}$ are each independently a nitrogen atom, $CR_{22}$ or a carbon atom bonded to another atom in the molecule of the second compound.

$R_{21}$ and $R_{22}$ are each independently a hydrogen atom or a substituent. When $R_{21}$ and $R_{22}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{21}$ and $R_{22}$ is a non-fused ring.

$X_2$ is $NR_{23}$, an oxygen atom or a sulfur atom.

$R_{23}$ is a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{23}$ is a non-fused ring.

$Y_{22}$ and $Y_{34}$ are optionally cross-linked via an oxygen atom, sulfur atom or $CR_{51}R_{52}$.

$Y_{24}$ and $Y_{32}$ are optionally cross-linked via an oxygen atom, sulfur atom or $CR_{53}R_{54}$.

$R_{51}$ to $R_{54}$ each independently represent the same as $R_{23}$ being the substituent.

In the formula (20A), a wavy line shows a bonding position with another atom or another structure in the molecule of the second compound.

For instance, when $Y_{22}$ and $Y_{34}$ are cross-linked via an oxygen atom, sulfur atom or $CR_{51}R_{52}$ in the formula (20A), the formula (20A) is represented by a formula (20A-1) below.

[Formula 41]

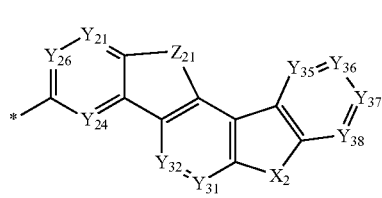

(20A-1)

It should be noted that $Z_{21}$ is an oxygen atom, sulfur atom or $CR_{51}R_{52}$ in the formula (20A-1). In the formula (20A-1), $X_2$, $Y_{21}$, $Y_{24}$, $Y_{26}$, $Y_{31}$, $Y_{32}$ and $Y_{35}$ to $Y_{38}$ respectively represent the same as $X_2$, $Y_{21}$, $Y_{24}$, $Y_{26}$, $Y_{31}$, $Y_{32}$ and $Y_{35}$ to $Y_{38}$ in the formula (20A).

In the exemplary embodiment, the second compound also preferably contains a group represented by a formula (20B) below.

[Formula 42]

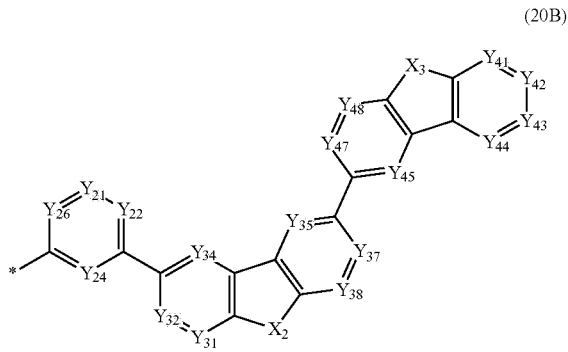

(20B)

In the formula (20B), $Y_{21}$, $Y_{22}$, $Y_{24}$ and $Y_{26}$ are each independently a nitrogen atom or $CR_{21}$.

$Y_{31}$, $Y_{32}$, $Y_{34}$, $Y_{35}$, $Y_{37}$ and $Y_{38}$ are each independently a nitrogen atom or $CR_{22}$. $Y_{41}$ to $Y_{45}$, $Y_{47}$ and $Y_{48}$ are each independently a nitrogen atom, $CR_{24}$ or a carbon atom bonded to another atom in the molecule of the second compound.

$R_{21}$, $R_{22}$ and $R_{24}$ are each independently a hydrogen atom or a substituent. When $R_{21}$, $R_{22}$ and $R_{24}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{21}$, $R_{22}$ and $R_{24}$ is a non-fused ring.

$X_2$ is $NR_{23}$, an oxygen atom or a sulfur atom.

$X_3$ is $NR_{25}$, an oxygen atom or a sulfur atom.

$R_{23}$ and $R_{25}$ are each independently selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{23}$ and $R_{25}$ is a non-fused ring.

$Y_{22}$ and $Y_{34}$ are optionally cross-linked via an oxygen atom, sulfur atom or $CR_{51}R_{52}$.

$Y_{24}$ and $Y_{32}$ are optionally cross-linked via an oxygen atom, sulfur atom or $CR_{53}R_{54}$.

$R_{51}$ to $R_{54}$ each independently represent the same as $R_{23}$ and $R_{25}$ being the substituent.

In the formula (20B), a wavy line shows a bonding position with another atom or another structure in the molecule of the second compound.

For instance, when $Y_{22}$ and $Y_{34}$ are cross-linked via an oxygen atom, sulfur atom or $CR_{51}R_{52}$ in the formula (20B), the formula (20B) is represented by a formula (20A-1) below.

[Formula 43]

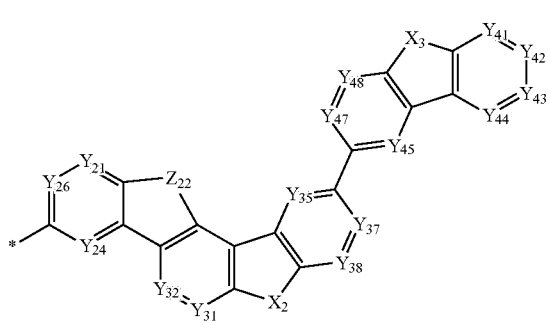

(20B-1)

It should be noted that $Z_{22}$ is an oxygen atom, sulfur atom or $CR_{51}R_{52}$ in the formula (20B-1). In the formula (20B-1), $X_2$, $X_3$, $Y_{21}$, $Y_{24}$, $Y_{26}$, $Y_{31}$, $Y_{32}$, $Y_{35}$, $Y_{37}$, $Y_{38}$, $Y_{41}$ to $Y_{45}$, $Y_{47}$ and $Y_{48}$ represent the same as $X_2$, $X_3$, $Y_{21}$, $Y_{24}$, $Y_{26}$, $Y_{31}$, $Y_{32}$, $Y_{35}$, $Y_{37}$, $Y_{38}$, $Y_{41}$ to $Y_{45}$, $Y_{47}$ and $Y_{48}$ in the formula (20B).

In the exemplary embodiment, the second compound also preferably contains a group represented by a formula (20C) below.

[Formula 44]

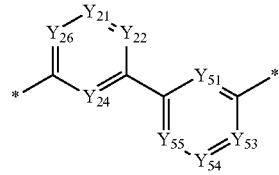

(20C)

In the formula (20C), $Y_{21}$, $Y_{22}$, $Y_{24}$ and $Y_{26}$ are each independently a nitrogen atom or $CR_{21}$.

$Y_{51}$, $Y_{53}$, $Y_{54}$ and $Y_{55}$ are each independently a nitrogen atom or $CR_{26}$.

$R_{21}$ and $R_{26}$ are each independently a hydrogen atom or a substituent. When $R_{21}$ and $R_{26}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{21}$ and $R_{26}$ is a non-fused ring.

$Y_{22}$ and $Y_{51}$ are optionally cross-linked via an oxygen atom, sulfur atom or $CR_{55}R_{56}$.

$Y_{24}$ and $Y_{55}$ are optionally cross-linked via an oxygen atom, sulfur atom or $CR_{57}R_{58}$.

$R_{55}$ to $R_{58}$ are each independently a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{55}$ to $R_{58}$ is a non-fused ring.

In the formula (20C), a wavy line shows a bonding position with another atom or another structure in the molecule of the second compound.

For instance, when $Y_{22}$ and $Y_{51}$ are cross-linked via an oxygen atom, sulfur atom or $CR_{55}R_{56}$ in the formula (20C), the formula (20C) is represented by a formula (20C-1) below.

[Formula 45]

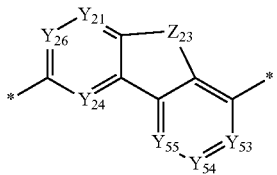

(20C-1)

It should be noted that $Z_{23}$ is an oxygen atom, sulfur atom or $CR_{55}R_{56}$ in the formula (20C-1). In the formula (20C-1), $Y_{21}$, $Y_{24}$, $Y_{26}$ and $Y_{53}$ to $Y_{55}$ respectively represent the same as $Y_{21}$, $Y_{24}$, $Y_{26}$ and $Y_{53}$ to $Y_{55}$ in the formula (20C).

In the exemplary embodiment, the second compound also preferably contains a group represented by a formula (20D) below.

[Formula 46]

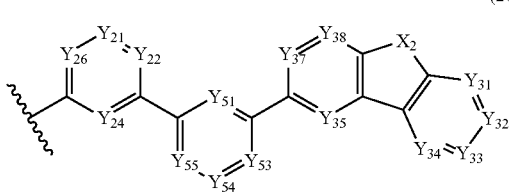

(20D)

In the formula (20D), $Y_{21}$, $Y_{22}$, $Y_{24}$ and $Y_{26}$ are each independently a nitrogen atom or $CR_{21}$.

$Y_{51}$, $Y_{53}$, $Y_{54}$ and $Y_{55}$ are each independently a nitrogen atom or $CR_{26}$.

$Y_{31}$ to $Y_{35}$, $Y_{37}$ and $Y_{38}$ are each independently a nitrogen atom, $CR_{22}$ or a carbon atom bonded to another atom in the molecule of the second compound.

$R_{21}$, $R_{22}$ and $R_{26}$ are each independently a hydrogen atom or a substituent. When $R_{21}$, $R_{22}$ and $R_{26}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{21}$, $R_{22}$ and $R_{26}$ is a non-fused ring.

$X_2$ is $NR_{23}$, an oxygen atom or a sulfur atom.

$R_{23}$ is a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{23}$ is a non-fused ring.

$Y_{22}$ and $Y_{51}$ are optionally cross-linked via an oxygen atom, sulfur atom or $CR_{55}R_{56}$.

$Y_{24}$ and $Y_{55}$ are optionally cross-linked via an oxygen atom, sulfur atom or $CR_{57}R_{58}$.

$Y_{51}$ and $Y_{37}$ are optionally cross-linked via an oxygen atom, sulfur atom or $CR_{59}R_{60}$.

$Y_{53}$ and $Y_{35}$ are optionally cross-linked via an oxygen atom, sulfur atom or $CR_{61}R_{62}$.

$R_{55}$ to $R_{62}$ each independently represent the same as $R_{23}$ being the substituent. In the formula (20D), a wavy line shows a bonding position with another atom or another structure in the molecule of the second compound.

For instance, when $Y_{22}$ and $Y_{51}$ are cross-linked via an oxygen atom, sulfur atom or $CR_{55}R_{56}$ in the formula (20D), the formula (20D) is represented by a formula (20D-1) below.

[Formula 47]

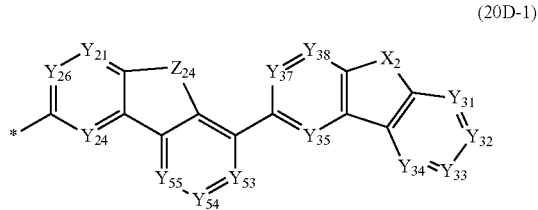

(20D-1)

It should be noted that $Z_{24}$ is an oxygen atom, sulfur atom or $CR_{55}R_{56}$ in the formula (20D-1). In the formula (20D-1), $X_2$, $Y_{21}$, $Y_{24}$, $Y_{26}$, $Y_{31}$ to $Y_{35}$, $Y_{37}$, $Y_{38}$ and $Y_{53}$ to $Y_{55}$ respectively represent the same as $X_2$, $Y_{21}$, $Y_{24}$, $Y_{26}$, $Y_{31}$ to $Y_{35}$, $Y_{37}$, $Y_{38}$ and $Y_{53}$ to $Y_{55}$ in the formula (20D).

For instance, when $Y_{51}$ and $Y_{37}$ are cross-linked via an oxygen atom, sulfur atom or $CR_{59}R_{60}$ in the formula (20D), the formula (20D) is represented by a formula (20D-2) below.

[Formula 48]

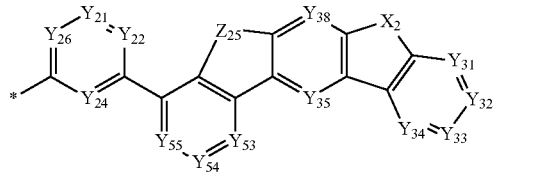

(20D-2)

It should be noted that $Z_{25}$ is an oxygen atom, sulfur atom or $CR_{55}R_{60}$ in the formula (20D-2). In the formula (20D-2), $X_2$, $Y_{21}$, $Y_{22}$, $Y_{24}$, $Y_{26}$, $Y_{31}$ to $Y_{35}$, $Y_{38}$ and $Y_{53}$ to $Y_{55}$ respectively represent the same as $X_2$, $Y_{21}$, $Y_{22}$, $Y_{24}$, $Y_{26}$, $Y_{31}$ to $Y_{35}$, $Y_{38}$ and $Y_{53}$ to $Y_{55}$ in the formula (20D).

In the exemplary embodiment, the second compound also preferably contains a group represented by a formula (20E) below.

[Formula 49]

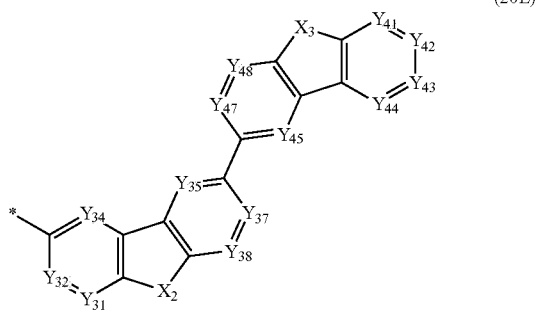

(20E)

In the formula (20E), $Y_{31}$, $Y_{32}$, $Y_{34}$, $Y_{35}$, $Y_{37}$ and $Y_{38}$ are each independently a nitrogen atom or $CR_{22}$.

$Y_{41}$ to $Y_{45}$, $Y_{47}$ and $Y_{48}$ are each independently a nitrogen atom, $CR_{24}$ or a carbon atom bonded to another atom in the molecule of the second compound.

$R_{22}$ and $R_{24}$ are each independently a hydrogen atom or a substituent. When $R_{22}$ and $R_{24}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{22}$ and $R_{24}$ is a non-fused ring.

$X_2$ is $NR_{23}$, an oxygen atom or a sulfur atom.

$X_3$ is $NR_{25}$, an oxygen atom or a sulfur atom $R_{23}$ and $R_{25}$ are each independently selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{23}$ and $R_{25}$ is a non-fused ring.

In the formula (20E), a wavy line shows a bonding position with another atom or another structure in the molecule of the second compound.

In the exemplary embodiment, the second compound may contain at least one of a group represented by a formula (20F) below, a group represented by a formula (20G) below and a group represented by a formula (20H) below.

[Formula 50]

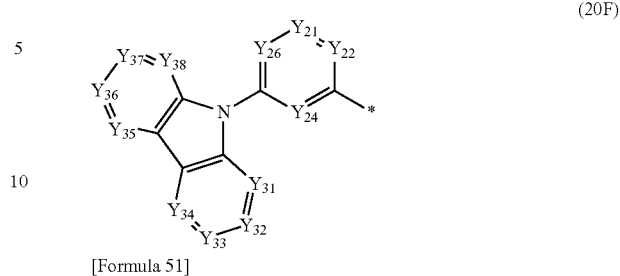

(20F)

[Formula 51]

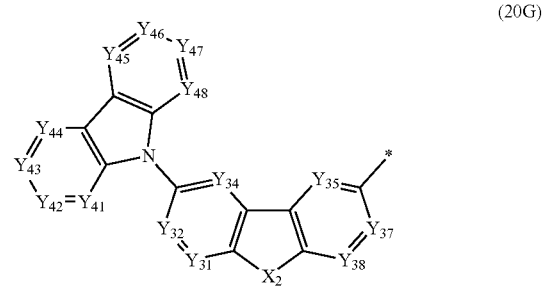

(20G)

[Formula 52]

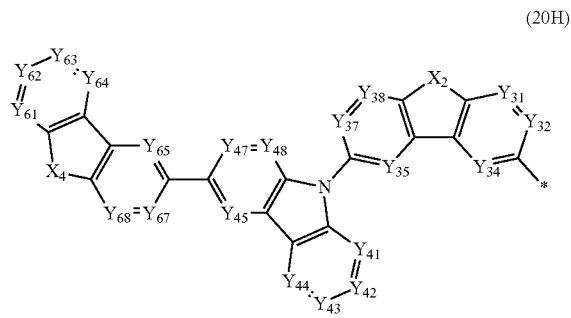

(20H)

In the formulae (20F), (20G) and (20H): $Y_{21}$, $Y_{22}$, $Y_{24}$, $Y_{26}$, $Y_{31}$ to $Y_{38}$, $Y_{41}$ to $Y_{48}$, $Y_{61}$ to $Y_{65}$, $Y_{67}$ and $Y_{68}$ are each independently a nitrogen atom, $CR_{27}$ or a carbon atom bonded to another atom in the molecule of the second compound.

$R_{27}$ is each independently a hydrogen atom or a substituent. When $R_{27}$ is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{27}$ is a non-fused ring.

$X_2$ and $X_4$ are each independently $NR_{28}$, an oxygen atom or a sulfur atom, in which $R_{28}$ is each independently selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group. However, the substituted or unsubstituted aromatic hydrocarbon group having 6 to 30 ring carbon atoms in $R_{28}$ is a non-fused ring.

Wavy lines in the formulae (20F), (20G) and (20H) each show a bonding position with another atom or another structure in the molecule of the second compound.

In the exemplary embodiment, $X_2$ is preferably an oxygen atom or a sulfur atom, preferably an oxygen atom.

$X_3$ is preferably an oxygen atom or a sulfur atom, preferably an oxygen atom.

$X_4$ is preferably an oxygen atom or a sulfur atom, preferably an oxygen atom.

Moreover, $X_2$ and $X_3$ are preferably an oxygen atom.
Moreover, $X_2$ and $X_4$ are preferably an oxygen atom.

In the exemplary embodiment, $R_{21}$, $R_{22}$, $R_{24}$, $R_{26}$ and $R_{27}$ are each independently a hydrogen atom or a substituent. The substituent in $R_{21}$, $R_{22}$, $R_{24}$, $R_{26}$ and $R_{27}$ is preferably selected from the group consisting of a fluorine atom, cyano group, substituted or unsubstituted alkyl group having 1 to 30 carbon atoms, substituted or unsubstituted aromatic hydrocarbon group having 6 to 30 ring carbon atoms, and substituted or unsubstituted heterocyclic group having 5 to 30 ring atoms. $R_{21}$, $R_{22}$, $R_{24}$, $R_{26}$ and $R_{27}$ are more preferably a hydrogen atom, a cyano group, a substituted or unsubstituted aromatic hydrocarbon group having 6 to 30 ring carbon atoms, or a substituted or unsubstituted aromatic heterocyclic group having 5 to 30 ring atoms. However, the substituted or unsubstituted aromatic hydrocarbon group having 6 to 30 ring carbon atoms in $R_{21}$, $R_{22}$, $R_{24}$, $R_{26}$ and $R_{27}$ is a non-fused ring.

In the exemplary embodiment, $R_{23}$, $R_{25}$ and $R_{28}$ are preferably each independently a substituent selected from the group consisting of a substituted or unsubstituted aromatic hydrocarbon group having 6 to 30 ring carbon atoms and a substituted or unsubstituted heterocyclic group having 5 to 30 ring atoms, more preferably a substituent selected from the group consisting of a substituted or unsubstituted aromatic hydrocarbon group having 6 to 20 ring carbon atoms and a substituted or unsubstituted heterocyclic group having 5 to 20 ring atoms. However, the substituted or unsubstituted aromatic hydrocarbon group having 6 to 30 ring carbon atoms in $R_{23}$, $R_{25}$ and $R_{28}$ is a non-fused ring.

In the exemplary embodiment, $R_{51}$ to $R_{62}$ are preferably each independently a substituent selected from the group consisting of a substituted or unsubstituted alkyl group having 1 to 30 carbon atoms, a substituted or unsubstituted aromatic hydrocarbon group having 6 to 30 ring carbon atoms, and a substituted or unsubstituted heterocyclic group having 5 to 30 ring atoms, more preferably a substituent selected from the group consisting of a substituted or unsubstituted aromatic hydrocarbon group having 6 to 20 ring carbon atoms and a substituted or unsubstituted heterocyclic group having 5 to 20 ring atoms. However, the substituted or unsubstituted aromatic hydrocarbon group having 6 to 30 ring carbon atoms in $R_{51}$ to $R_{62}$ is a non-fused ring.

In the exemplary embodiment, the second compound is also preferably an aromatic hydrocarbon compound or an aromatic heterocyclic compound.

In the exemplary embodiment, the second compound preferably contains no fused aromatic hydrocarbon ring in a molecule.

Method of Preparing Second Compound

The second compound represented by the above formula can be prepared by a method described in International Publication Nos. WO2012/153780 A1 and WO 2013/038650 A1.

Specific examples of the substituent for the second compound of the exemplary embodiment are shown below, but the invention is not limited thereto.

Specific examples of the aromatic hydrocarbon group (aryl group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group and fluorenyl group may be preferable.

Specific examples of the substituted aromatic hydrocarbon group include a tolyl group, xylyl group and 9,9-dimethylfluorenyl group.

As is understood from the specific examples, the aryl group includes both fused aryl group and non-fused aryl group.

Preferable examples of the aromatic hydrocarbon group include a phenyl group, biphenyl group, terphenyl group, quarterphenyl group, naphthyl group, triphenylenyl group and fluorenyl group.

Specific examples of the aromatic heterocyclic group (heteroaryl group, heteroaromatic ring group and heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothiophenyl group, dibenzothiophenyl group, azadibenzothiophenyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothiophenyl group, carbazolyl group, pyridyl group, pyrimidinyl group, triazinyl group, azadibenzofuranyl group and azadibenzothiophenyl group may be preferable.

The aromatic heterocyclic group is preferably any one of a dibenzofuranyl group, dibenzothiophenyl group, carbazolyl group, pyridyl group, pyrimidinyl group, triazinyl group, azadibenzofuranyl group and azadibenzothiophenyl group, and further preferably any one of a dibenzofuranyl group, dibenzothiophenyl group, azadibenzofuranyl group and azadibenzothiophenyl group.

In the second compound of the exemplary embodiment, the substituted silyl group is preferably a substituted or unsubstituted trialkylsilyl group, a substituted or unsubstituted arylalkylsilyl group, or a substituted or unsubstituted triarylsilyl group.

Specific examples of substituted or unsubstituted trialkylsilyl group include trimethylsilyl group and triethylsilyl group.

Specific examples of substituted or unsubstituted arylalkylsilyl group include diphenylmethylsilyl group, ditolylmethylsilyl group, and phenyldimethylsilyl group.

Specific examples of substituted or unsubstituted triarylsilyl group include triphenylsilyl group and tritolylsilyl group.

In the second compound of the exemplary embodiment, the substituted phosphine oxide is preferably a substituted or unsubstituted diaryl phosphine oxide group.

Specific examples of the substituted or unsubstituted diaryl phosphine oxide group include a diphenyl phosphine oxide group and ditolyl phosphine oxide group.

Examples of the second compound according to the exemplary embodiment are shown below. It should be noted that the second compound according to the invention is not limited to these specific examples.

[Formula 53]

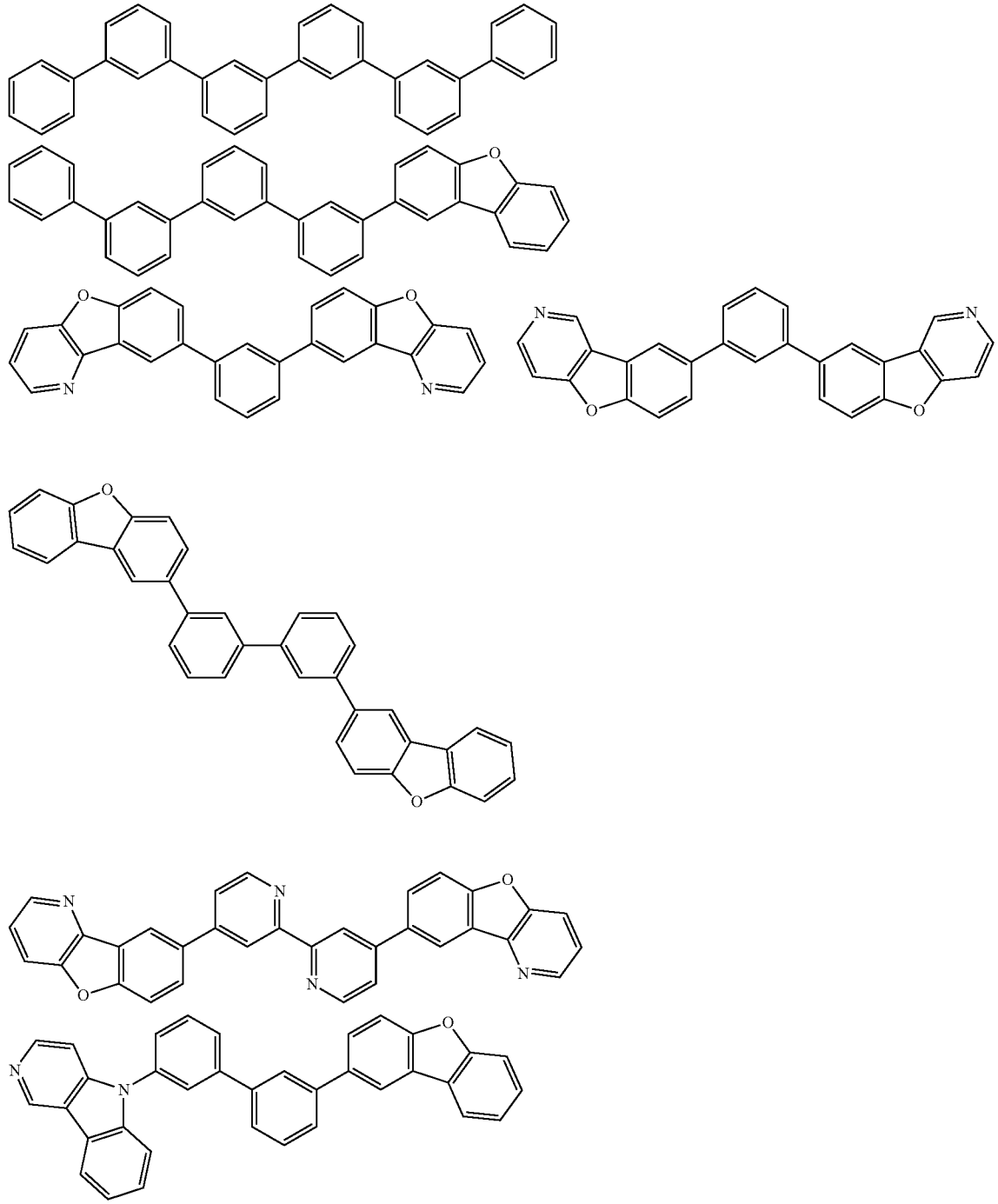

-continued
[Formula 54]
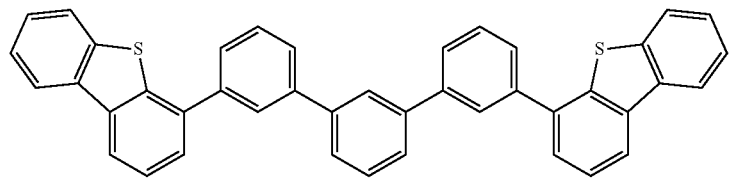
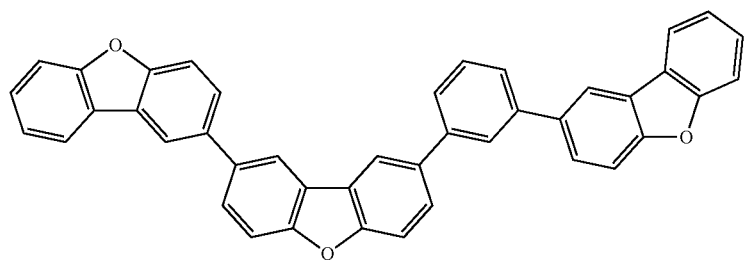
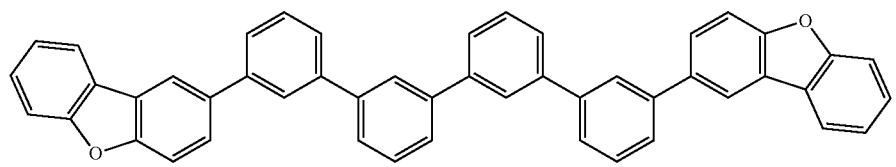
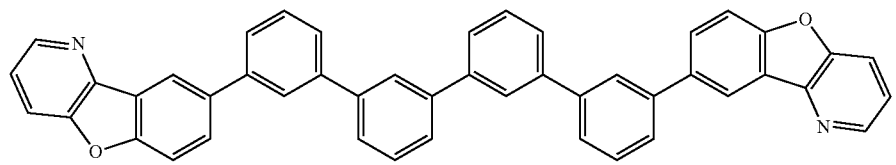
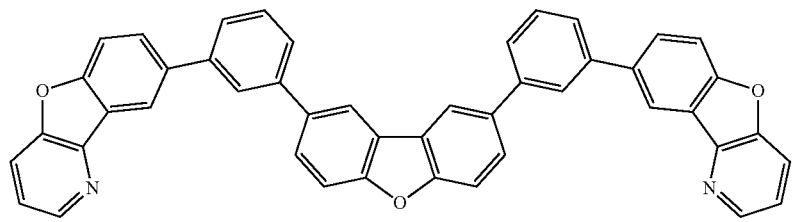
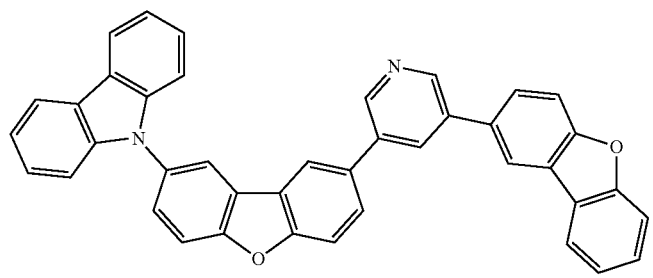

[Formula 55]
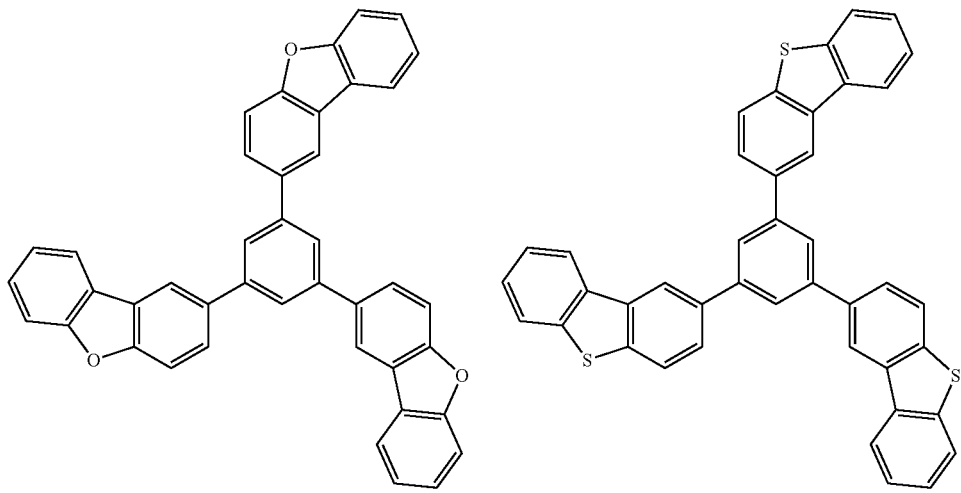
[Formula 56]
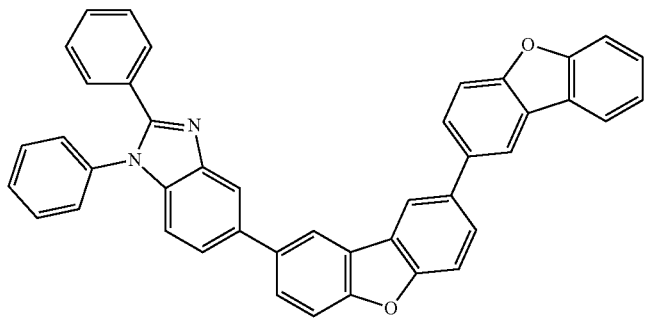
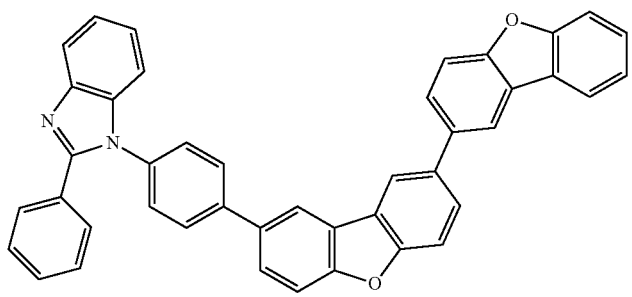
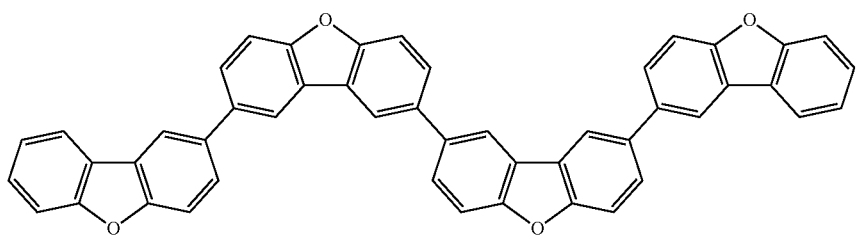

-continued

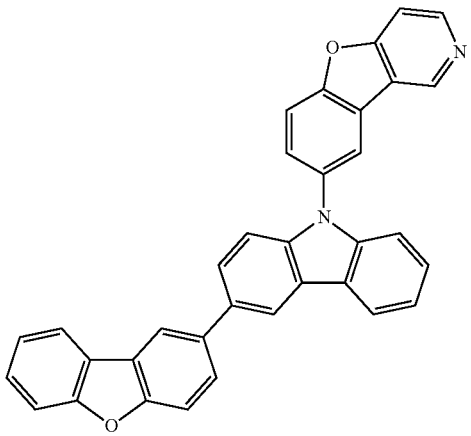

TADF Mechanism

In the organic EL device of the exemplary embodiment, the first compound is preferably a compound having a small ΔST(M1) so that inverse intersystem crossing from the triplet energy level of the first compound to the singlet energy level thereof is easily caused by a heat energy given from the outside. An energy state conversion mechanism to perform spin exchange from the triplet state of electrically excited excitons within the organic EL device to the singlet state by inverse intersystem crossing is referred to as TADF Mechanism.

Figure 3:
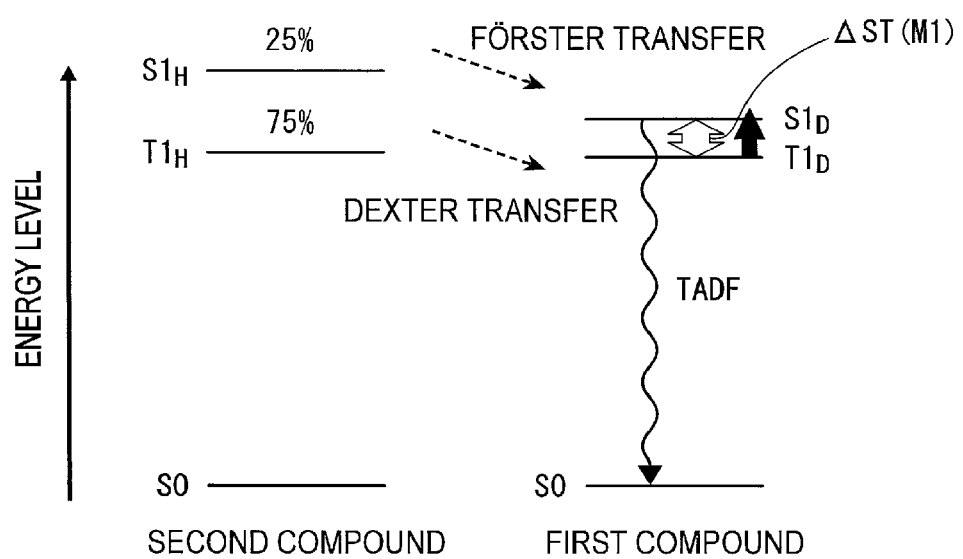
FIG. 3 shows a relationship between energy levels of a first compound and a second compound and an energy transfer between the first compound and the second compound in an emitting layer.

FIG. 3 shows an example of a relationship between energy levels of the first compound and the second compound in the emitting layer. In FIG. 3, S0 represents a ground state, $S1_H$ represents a lowest singlet state of the second compound, $T1_H$ represents a lowest triplet state of the second compound, $S1_D$ represents a lowest singlet state of the first compound, and $T1_D$ represents a lowest triplet state of the first compound. A dashed arrow shows energy transfer between the respective excited states in FIG. 3. Energy is transferred from the lowest triplet state $T1_H$ of the second compound to the lowest singlet state $S1_D$ or the lowest triplet state $T1_D$ of the first compound by Dexter transfer. When a compound having a small ΔST(M1) is used as the first compound, inverse intersystem crossing from the lowest triplet state $T1_D$ to the lowest singlet state $S1_D$ can be caused by a heat energy in the first compound. As a result, fluorescence from the lowest singlet state $S1_D$ of the first compound can be observed. It is inferred that the internal quantum efficiency can be theoretically raised up to 100% also by using delayed fluorescence by the TADF mechanism.

In the exemplary embodiment, a singlet energy S(M2) of the second compound is preferably larger than the singlet energy S(M1) of the first compound. In the exemplary embodiment, an energy gap $T_{77K}(M2)$ at 77 [K] of the second compound is preferably larger than an energy gap $T_{77K}(M1)$ at 77 [K] of the first compound.

Film Thickness of Emitting Layer

A film thickness of the emitting layer 5 of the organic EL device of the exemplary embodiment is preferably in a range from 5 nm to 50 nm, more preferably in a range from 7 nm to 50 nm, and further preferably in a range from 10 nm to 50 nm. The thickness of less than 5 nm may cause difficulty in forming the emitting layer 5 and in controlling chromaticity, while the thickness of more than 50 nm may raise drive voltage.

Content Ratio of Compounds in Emitting Layer

In the organic EL device 1 of the exemplary embodiment, a content ratio of the first compound in the emitting layer 5 is preferably in a range from 10 mass % to 99 mass % and a content ratio of the second compound in the emitting layer 5 is preferably in a range from 1 mass % to 90 mass %. An upper limit of the total of the respective content ratios of the first and second compounds in the emitting layer 5 is 100 mass %. It should be noted that the emitting layer 5 of the exemplary embodiment may further contain another material in addition to the first and second compounds.

Substrate

A substrate 2 is used as a support for the organic EL device 1. For instance, glass, quartz, plastics and the like are usable for the substrate 2. A flexible substrate is also usable. The flexible substrate is a bendable substrate, which is exemplified by a plastic substrate formed of polycarbonate, polyaryl ate, polyethersulfone, polypropylene, polyester, polyvinyl fluoride, polyvinyl chloride, polyimide, and polyethylene naphthalate. Moreover, an inorganic vapor deposition film is also usable.

Anode

Metal, alloy, an electrically conductive compound and a mixture thereof, which have a large work function, specifically, of 4.0 eV or more, is preferably usable as the anode 3 formed on the substrate 2. Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), or nitrides of a metal material (e.g., titanium nitride) are usable.

The above materials are typically deposited as a film by sputtering. For instance, indium zinc oxide can be deposited as a film by sputtering using a target that is obtained by adding zinc oxide in a range from 1 mass % to 10 mass % to indium oxide. Moreover, for instance, indium oxide containing tungsten oxide and zinc oxide can be deposited as a film by sputtering using a target that is obtained by adding tungsten oxide in a range from 0.5 mass % to 5 mass % and zinc oxide in a range from 0.1 mass % to 1 mass % to indium oxide. In addition, vapor deposition, coating, ink jet printing, spin coating and the like may be used for forming a film.

Among the organic layers formed on the anode 3, a hole injecting layer 6 formed adjacent to the anode 3 is formed of a composite material that facilitates injection of holes irrespective of the work function of the anode 3. Accordingly, a material usable as an electrode material (e.g., metal, alloy, an electrically conductive compound, a mixture thereof, and elements belonging to Groups 1 and 2 of the periodic table of the elements) is usable as the material for the anode 3.

The elements belonging to Groups 1 and 2 of the periodic table of the elements, which are materials having a small work function, namely, an alkali metal such as lithium (Li) and cesium (Cs) and an alkaline earth metal such as magnesium (Mg), calcium (Ca) and strontium (Sr), alloy thereof (e.g., MgAg, AlLi), a rare earth metal such as europium (Eu) and ytterbium (Yb), and alloy thereof are also usable as the material for the anode. When the anode 3 is formed of the alkali metal, alkaline earth metal and alloy thereof, vapor deposition and sputtering are usable. Further, when the anode is formed of silver paste and the like, coating, ink jet printing and the like are usable.

Hole Injecting Layer

A hole injecting layer 6 is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-4-[N'-(3-methylphenyl)-N'-phenylamino]phenyl-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

Moreover, a high-molecule compound (e.g., an oligomer, dendrimer and polymer) is also usable as the highly hole-injectable substance. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido] (abbreviation: PTP-DMA), and poly[N,N'-bis(4-butylphenyl)-N,N'-bis(phenyl)benzidine] (abbreviation: Poly-TPD). Furthermore, the examples of the high-molecule compound include a high-molecule compound added with an acid such as poly(3,4-ethylene dioxythiophene)/poly(styrene sulfonic acid) (PEDOT/PSS), and polyaniline/poly(styrene sulfonic acid) (PAni/PSS).

Hole Transporting Layer

A hole transporting layer 7 is a layer containing a highly hole-transportable substance. An aromatic amine compound, carbazole derivative, anthracene derivative and the like are usable for the hole transporting layer 7. Specific examples of a material for the hole transporting layer include 4,4'-bis[N-(1-naphthyl)-N-phenyl amino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/Vs or more.

A carbazole derivative (e.g., CBP, 9-[4-(N-carbazolyl)]phenyl-10-phenylanthracene (CzPA), and 9-phenyl-3-[4-(10-phenyl-9-anthryl)phenyl]-9H-carbazole (PCzPA)) and an anthracene derivative (e.g., t-BuDNA, DNA, and DPAnth) may be used for the hole transporting layer 7. A high polymer compound such as poly(N-vinylcarbazole) (abbreviation: PVK) and poly(-vinyltriphenylamine) (abbreviation: PVTPA) is also usable.

However, any substance having a hole transporting performance higher than an electron transporting performance may be used in addition to the above substances. A highly hole-transportable substance may be provided in the form of a single layer or a laminated layer of two or more layers of the above substance.

When the hole transporting layer includes two or more layers, one of the layers with a larger energy gap is preferably provided closer to the emitting layer 5.

In the exemplary embodiment, the hole transporting layer 7 preferably has a function of preventing triplet excitons generated in the emitting layer 5 from dispersing to the hole transporting layer 7 to trap the triplet excitons in the emitting layer 5.

Electron Transporting Layer

An electron transporting layer 8 is a layer containing a highly electron-transportable substance. As the electron transporting layer, 1) a metal complex such as an aluminum complex, beryllium complex and zinc complex, 2) heteroaromatic compound such as an imidazole derivative, benzimidazole derivative, azine derivative, carbazole derivative, and phenanthroline derivative, and 3) a high-molecule compound are usable. Specifically, as a low-molecule organic compound, a metal complex such as Alq, tris(4-methyl-8-quinolinato)aluminum (abbreviation: Almq3), bis(10-hydroxybenzo[h]quinolinato)beryllium (abbreviation: BeBq2), BAlq, Znq, ZnPBO and ZnBTZ are usable. In addition to the metal complex, a heteroaromatic compound such as 2-(4-biphenyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenyl)-1,2,4-triazole (abbreviation: TAZ), 3-(4-tert-butylphenyl)-4-(4-ethylphenyl)-5-(4-biphenyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) are usable. In the exemplary embodiment, a benzimidazole compound is suitably usable. The above-described substances mostly have an electron mobility of $10^{-6}$ cm$^2$/Vs or more. However, any substance having an electron transporting performance higher than a hole transporting performance may be used for the electron transporting layer 8 in addition to the above substances. The electron transporting layer 8 may be provided in the form of a single layer or a laminated layer of two or more layers of the above substance(s).

Moreover, a high-molecule compound is also usable for the electron transporting layer 8. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] abbreviation: PF-BPy) and the like are usable.

In the exemplary embodiment, the electron transporting layer 8 preferably has a function of preventing triplet excitons generated in the emitting layer 5 from dispersing to the electron transporting layer 8 and the electron injecting layer 9 to trap the triplet excitons in the emitting layer 5.

Electron Injecting Layer

An electron injecting layer 9 is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, a compound containing an alkali metal, alkaline earth metal and a compound thereof in the electron transportable substance, specifically, a compound containing magnesium (Mg) in Alq and the like may be used. With this compound, electrons can be more efficiently injected from the cathode 4.

Alternatively, a composite material provided by mixing an organic compound with an electron donor may be used for the electron injecting layer 9. The composite material exhibits excellent electron injecting performance and electron transporting performance since the electron donor generates electron in the organic compound. In this arrangement, the organic compound is preferably a material exhibiting an excellent transforming performance of the generated electrons. Specifically, for instance, the above-described substance for the electron transporting layer 8 (e.g., the metal complex and heteroaromatic compound) is usable. The electron donor may be any substance exhibiting an electron donating performance to the organic compound. Specifically, an alkali metal, alkaline earth metal and a rare earth metal are preferable, examples of which include lithium, cesium, magnesium, calcium, erbium and ytterbium. Moreover, an alkali metal oxide and alkaline earth metal oxide are preferable, examples of which include lithium oxide, calcium oxide, and barium oxide. Further, Lewis base such as magnesium oxide is also usable. Furthermore, tetrathiafulvalene (abbreviation: TTF) is also usable.

Cathode

Metal, alloy, an electrically conductive compound, a mixture thereof and the like, which have a small work function, specifically, of 3.8 eV or less, is preferably usable as a material for the cathode 4. Specific examples of the material for the cathode include: the elements belonging to Groups 1 and 2 of the periodic table of the elements, namely, an alkali metal such as lithium (Li) and cesium (Cs) and an alkaline earth metal such as magnesium (Mg), calcium (Ca) and strontium (Sr); alloy thereof (e.g., MgAg, AlLi); a rare earth metal such as europium (Eu) and ytterbium (Yb); and alloy thereof.

When the cathode 4 is formed of the alkali metal, alkaline earth metal and alloy thereof, vapor deposition and sputtering are usable. Moreover, when the anode is formed of silver paste and the like, coating, inkjet printing and the like are usable.

By providing the electron injecting layer 9, various conductive materials such as Al, Ag, ITO, graphene and indium tin oxide containing silicon or silicon oxide are usable for forming the cathode 4 irrespective of the magnitude of the work function. The conductive materials can be deposited as a film by sputtering, ink jet printing, spin coating and the like.

Layer Formation Method(s)

A method for forming each layer of the organic EL device 1 in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Film Thickness

The thickness of each organic layer of the organic EL device 1 in the exemplary embodiment is subject to no limitation except for the thickness particularly described above. However, the thickness is typically preferably in a range of several nanometers to 1 μm because an excessively thin film is likely to entail defects such as a pin hole while an excessively thick film requires high applied voltage and deteriorates efficiency.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, carbon atom(s) included in the substituent is not counted as the ring carbon atoms. The same applies to the "ring carbon atoms" described below, unless particularly noted. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring or a naphthalene ring is substituted, for instance, by an alkyl group, the carbon atoms of the alkyl group are not counted as the ring carbon atoms. For instance, when a fluorene ring (inclusive of a spirofluorene ring) is bonded as a substituent to a fluorene ring, the carbon atoms of the fluorene ring as a substituent are not counted as the ring carbon atoms.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., hydrogen atom(s) for saturating the valence of the atom which forms the ring) and atom(s) in a substituent by which the ring is substituted are not counted as the ring atoms. The same applies to the "ring atoms" described below, unless particularly noted. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming a substituent are not counted as the ring atoms. For instance, when a fluorene ring (inclusive of a spirofluorene ring) is bonded as a substituent to a fluorene ring, the atoms of the fluorene ring as a substituent are not included in the ring atoms.

Next, each of substituents described in the above formulae will be described.

Examples of the aromatic hydrocarbon group group having 6 to 30 ring carbon atoms (occasionally referred to as an aryl group) in the exemplary embodiment are a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, more preferably 6 to 14 ring carbon atoms, further preferably 6 to 12 ring carbon atoms. Among the aryl group, a phenyl group, biphenyl group, naphthyl group, phenanthryl group, terphenyl group and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms later described in the exemplary embodiment.

In the exemplary embodiment, the heterocyclic group (occasionally referred to as heteroaryl group, heteroaromatic ring group or aromatic heterocyclic group) having 5 to 30 ring atoms preferably contains at least one atom selected from the group consisting of nitrogen, sulfur, oxygen, silicon, selenium atom and germanium atom, and more preferably contains at least one atom selected from the group consisting of nitrogen, sulfur and oxygen.

Examples of the heterocyclic group (occasionally referred to as heteroaryl group, heteroaromatic ring group or aromatic heterocyclic group) having 5 to 30 ring atoms in the exemplary embodiment include a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4carbazolyl group is preferably substituted by a substituted or unsubstituted aryl group having 6 to 30 ring carbon atoms or a substituted or unsubstituted heterocyclic group having 5 to 30 ring atoms in the exemplary embodiment.

In the exemplary embodiment, the heterocyclic group may be a group derived from any one of partial structures represented by formulae (XY-1) to (XY-18).

[Formula 57]

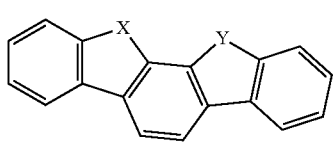

(XY-1)

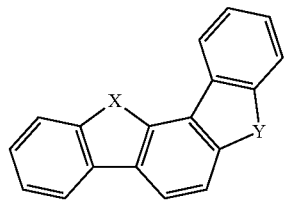

(XY-2)

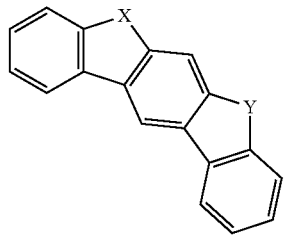

(XY-3)

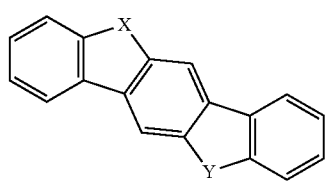

(XY-4)

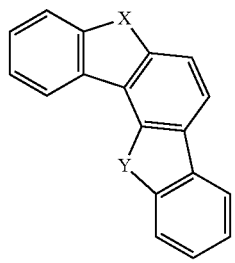

(XY-5)

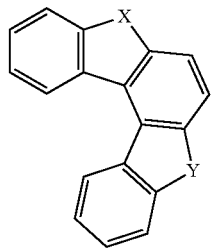

(XY-6)

[Formula 58]

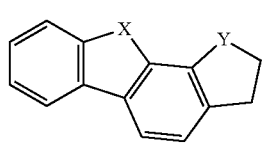

(XY-7)

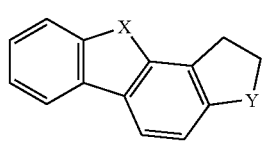

(XY-8)

(XY-9) 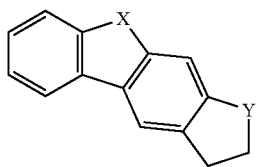

(XY-10) 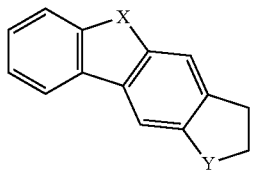

(XY-11) 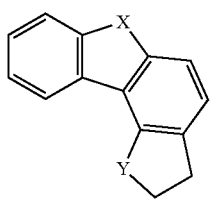

(XY-12) 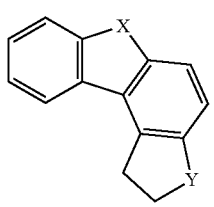

[Formula 59]

(XY-13) 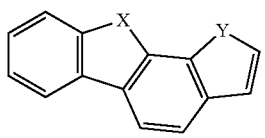

(XY-14) 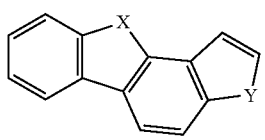

(XY-15) 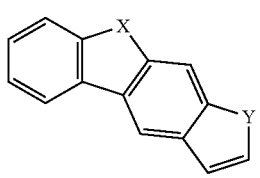

(XY-16) 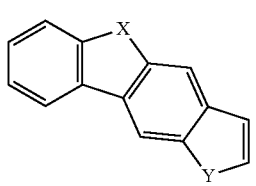

(XY-17) 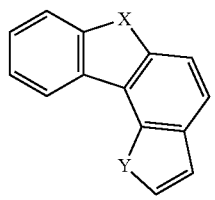

(XY-18) 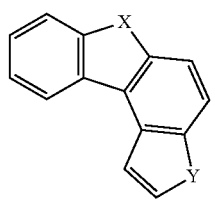

In the formulae (XY-1) to (XY-18), X and Y are each independently a hetero atom, and are preferably an oxygen atom, sulfur atom, selenium atom, silicon atom or germanium atom. The partial structures represented by the formulae (XY-1) to (XY-18) may each be bonded in any position to be a heterocyclic group, which may be substituted.

In the exemplary embodiment, examples of the substituted or unsubstituted carbazolyl group may include a group in which a carbazole ring is further fused with a ring(s) as shown in the following formulae. Such a group may be substituted. The group may be bonded in any position as desired.

[Formula 60]

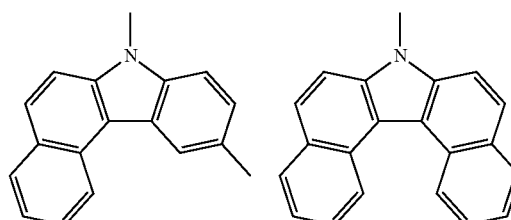

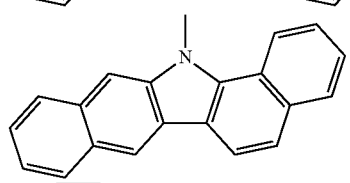

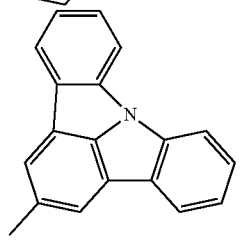

The alkyl group having 1 to 30 carbon atoms in the exemplary embodiment may be linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group in the exemplary embodiment are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group provided by substituting an alkyl group with a halogen atom is exemplified by one provided by substituting an alkyl group having 1 to 30 carbon atoms with one or more halogen atoms. Specific examples of the above halogenated alkyl group are a fluoromethyl group, difluoromethyl group, trifluoromethyl group, fluoroethyl group, trifluoromethylmethyl group, trifluoroethyl group and pentafluoroethyl group.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, tri ethyl silyl group, tri-n-butyl silyl group, tri-n-octyl silyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be the same or different.

Examples of the arylsilyl group having 6 to 30 ring carbon atoms in the exemplary embodiment are a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group including three of the aryl group listed as the examples of the aryl group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group. The alkoxy group preferably has 1 to 20 carbon atoms.

A halogenated alkoxy group provided by substituting an alkoxy group with a halogen atom is exemplified by one provided by substituting an alkoxy group having 1 to 30 carbon atoms with one or more halogen atoms.

The aryloxy group having 6 to 30 ring carbon atoms in the exemplary embodiment is represented by $-OZ_2$. $Z_2$ is exemplified by the above aryl group having 6 to 30 ring carbon atoms. The aryloxy group preferably has 6 to 20 ring carbon atoms. The aryloxy group is exemplified by a phenoxy group.

The alkylamino group having 2 to 30 carbon atoms is represented by $-NHR_V$ or $-N(R_V)_2$. $R_V$ is exemplified by the alkyl group having 1 to 30 carbon atoms.

The arylamino group having 6 to 60 ring carbon atoms is represented by $-NHR_W$ or $-N(R_W)_2$. $R_W$ is exemplified by the above aryl group having 6 to 30 ring carbon atoms.

The alkylthio group having 1 to 30 carbon atoms is represented by $-SR_V$. $R_V$ is exemplified by the alkyl group having 1 to 30 carbon atoms. The alkylthio group preferably has 1 to 20 carbon atoms.

The arylthio group having 6 to 30 ring carbon atoms is represented by $-SR_W$. $R_W$ is exemplified by the above aryl group having 6 to 30 ring carbon atoms. The arylthio group preferably has 6 to 20 ring carbon atoms.

Examples of the halogen atom include a fluorine atom, chlorine atom, bromine tom and iodine atom, among which a fluorine atom is preferable.

In the exemplary embodiment, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

In the exemplary embodiment, a hydrogen atom includes isotope having different numbers of neutrons, specifically, protium, deuterium and tritium.

Examples of the substituent meant by "substituted or unsubstituted" are an alkenyl group, alkynyl group, aralkyl group, halogen atom, cyano group, hydroxyl group, nitro group and carboxy group, in addition to the above-described aryl group, heterocyclic group, alkyl group (linear or branched alkyl group, cycloalkyl group and haloalkyl group), alkylsilyl group, arylsilyl group, alkoxy group, aryloxy group, alkylamino group, aryl amino group, alkylthio group, and arylthio group.

Among the above substituents, an aryl group, heterocyclic group, alkyl group, halogen atom, alkylsilyl group, arylsilyl group and cyano group are preferable. More preferable substituents are one listed as the preferable substituents described for each substituent.

These substituents may be further substituted by the above substituent(s) In addition, plural ones of these substituents may be mutually bonded to form a ring.

The alkenyl group is preferably an alkenyl group having 2 to 30 carbon atoms, which may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group, and cyclohexadienyl group.

The alkynyl group is preferably an alkynyl group having 2 to 30 carbon atoms, which may be linear, branched or cyclic. Examples of the alkynyl group include ethynyl, propynyl, and 2-phenylethynyl.

The aralkyl group is preferably an aralkyl group having 6 to 30 ring carbon atoms and is represented by $-Z_3-Z_4$. $Z_3$ is exemplified by an alkylene group corresponding to the above alkyl group having 1 to 30 carbon atoms. $Z_4$ is exemplified by the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthyl ethyl group, 2-α-naphthyl ethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

"Unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of a substituted ZZ group. "YY" is larger than "XX" and each of "XX" and "YY" represents an integer of 1 or more.

Herein, "XX to YY atoms" in the description of "substituted or unsubstituted ZZ group having XX to YY atoms" represent atoms of an unsubstituted ZZ group and does not include atoms of a substituent(s) of a substituted ZZ group. "YY" is larger than "XX" and each of "XX" and "YY" represents an integer of 1 or more.

The same description as the above applies to "substituted or unsubstituted" in the following compound or a partial structure thereof.

In the exemplary embodiment, when substituents are mutually bonded to form a cyclic structure, the cyclic structure is a saturated ring, unsaturated ring or aromatic ring.

Electronic Device

The organic EL device 1 of the exemplary embodiment is usable in an electronic device such as a display device and a light-emitting device. Examples of the display unit include display components such as en organic EL panel module, TV, mobile phone, tablet, and personal computer. Examples of the light-emitting unit include an illuminator and a vehicle light.

Second Exemplary Embodiment

An arrangement of an organic EL device according to a second exemplary embodiment will be described below. In the description of the second exemplary embodiment, the same components as those in the first exemplary embodiment are denoted by the same reference signs and names to simplify or omit an explanation of the components. In the second exemplary embodiment, the same materials and compounds as described in the first exemplary embodiment are usable, unless otherwise specified.

The organic EL device of the second exemplary embodiment is different from the organic EL device 1 of the first exemplary embodiment in that the first compound contained in the emitting layer is represented by the formula (30), but is the same as the organic EL device 1 of the first exemplary embodiment with respect to the other points. The emitting layer of the organic EL device of the second exemplary embodiment contains the delayed-fluorescent first compound represented by the formula (30) below and the second compound described in the first exemplary embodiment. The first compound of the exemplary embodiment is not a metal complex. In the second exemplary embodiment, the emitting layer preferably contains no phosphorescent metal complex, more preferably contains no other metal complex in addition to the phosphorescent metal complex.

[Formula 61]

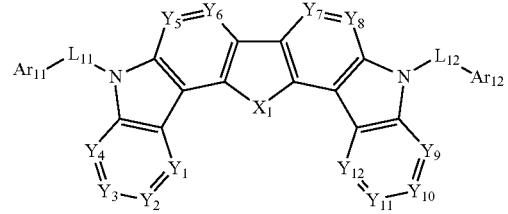

(30)

In the formula (30), $Ar_{11}$ and $Ar_{12}$ are each independently a substituted or unsubstituted aromatic hydrocarbon group having 6 to 30 ring carbon atoms, or a substituted or unsubstituted heterocyclic group having 5 to 30 ring atoms, $Ar_{11}$ and $Ar_{12}$ being the same.

$L_{11}$ and $L_{12}$ are a single bond or a linking group. The linking group in $L_1$ is a substituted or un substituted aromatic hydrocarbon group having 6 to 30 ring carbon atoms or a substituted or unsubstituted heterocyclic group having 5 to 30 ring atoms, $L_{11}$ and $L_{12}$ being the same.

$Y_1$ to $Y_{12}$ are each independently a nitrogen atom or $CR_1$.

$X_1$ is an oxygen atom, a sulfur atom, $N-R_{10}$, $CR_{11}R_{12}$, $SiR_{13}R_{14}$ or $GeR_{15}R_{16}$.

$R_1$ and $R_{10}$ to $R_{16}$ are each independently a hydrogen atom or a substituent. When $R_1$ and $R_{10}$ to $R_{16}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group.

A plurality of $R_1$ are optionally mutually the same or different. When at least two of the plurality of $R_1$ are substituents, the substituents $R_1$ are optionally mutually bonded to form a cyclic structure.

In the exemplary embodiment, $L_{11}$ and $L_{12}$ are preferably a substituted or unsubstituted aromatic hydrocarbon group having 6 to 30 ring carbon atoms, or substituted or unsubstituted aromatic heterocyclic group having 5 to 30 ring atoms.

In the exemplary embodiment, it is preferable that $L_{11}$ and $L_{12}$ are a single bond and $Ar_{11}$ and $Ar_{12}$ are the same. When $L_{11}$ and $L_{12}$ each are the single bond, the formula (1) is represented by a formula (1A) below.

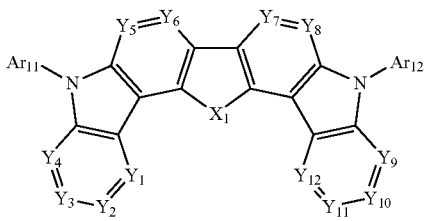
(1A)

In the formula (1A), $L_1$, $Y_1$ to $Y_{12}$ and $X_1$ respectively represent the same as $L_1$, $Y_1$ to $Y_{12}$ and $X_1$ in the formula (1). In the formula (1A), $Ar_{11}$ and $Ar_{12}$ are preferably a substituted or unsubstituted aromatic hydrocarbon group having 6 to 30 ring carbon atoms, or a substituted or unsubstituted aromatic heterocyclic group having 5 to 30 ring atoms, $Ar_{11}$ and $Ar_{12}$ being the same. It is further preferable that, in the formula (1A), $Y_1$ and $Y_{12}$ are the same, $Y_2$ and $Y_{11}$ are the same, $Y_3$ and $Y_{10}$ are the same, $Y_4$ and $Y_9$ are the same, $Y_5$ and $Y_8$ are the same, and $Y_6$ and $Y_7$ are the same.

In the exemplary embodiment, it is preferable that, in the formulae (30) and (1A), $Y_1$ and $Y_{12}$ are the same, $Y_2$ and $Y_{11}$ are the same, $Y_3$ and $Y_{10}$ are the same, $Y_4$ and $Y_9$ are the same, $Y_5$ and $Y_8$ are the same, and $Y_6$ and $Y_7$ are the same.

In the exemplary embodiment, $Y_1$ to $Y_{12}$ are preferably $CR_1$, in which $R_1$ is more preferably a hydrogen atom.

In the exemplary embodiment, $Ar_{11}$ and $Ar_{12}$ are preferably the group represented by the formula (11).

Also in the exemplary embodiment, $Ar_{11}$ and $Ar_{12}$ are preferably the group represented by the formula (11a), the group represented by the formula (11b) below, the group represented by the formula (11c) below, the group represented by the formula (11d) below, or the group represented by the formula (11e).

In the exemplary embodiment, $Ar_{11}$ and $Ar_{12}$ are preferably the group represented by the formula (11f) or the group represented by the formula (11h).

In the exemplary embodiment, $Ar_{11}$ and $Ar_{12}$ are preferably substituted by at least one electron attracting group. The electron attracting group is preferably the same as described above.

In the exemplary embodiment, $Ar_{11}$ and $Ar_{12}$ are also preferably a substituted or unsubstituted pyridinyl group, substituted or unsubstituted pyrimidinyl group, or substituted or unsubstituted triazinyl. Also in the exemplary embodiment, $Ar_{11}$ and $Ar_{12}$ are each preferably the group represented by any one of the formulae (11i), (11j), (11k), (11m), (11n), (11p), (11q), (11r) and (11s).

In the exemplary embodiment, $Ar_{11}$ and $Ar_{12}$ are more preferably a substituted or unsubstituted aromatic hydrocarbon cyclic group having 6 to 30 ring carbon atoms, more preferably an aromatic hydrocarbon group selected from the group consisting of a phenyl group, biphenyl group, terphenyl group, naphthyl group, phenanthryl group and triphenylenyl group. In this arrangement, the aromatic hydrocarbon group is further preferably substituted by at least one electron attracting group.

In the exemplary embodiment, $X_1$ is preferably an oxygen atom or a sulfur atom, preferably an oxygen atom.

Modification of Embodiments

It should be noted that the invention is not limited to the above exemplary embodiments but may include any modification and improvement as long as such modification and improvement are compatible with the invention.

For instance, the emitting layer is not limited to a single layer, but may be provided by laminating a plurality of emitting layers. When the organic EL device has the plurality of emitting layers, it is only required that at least one of the emitting layers contains the first and second compounds. For instance, the rest of the emitting layers may be a fluorescent emitting layer or a phosphorescent emitting layer using emission by electronic transition from the triplet state directly to the ground state.

When the organic EL device includes the plurality of emitting layers, the plurality of emitting layers may be adjacent to each other, or may be laminated on each other via an intermediate layer, a so-called tandem organic EL device.

For instance, a blocking layer may be provided in contact with an anode-side or a cathode-side of the emitting layer. It is preferable that the blocking layer is adjacent to the emitting layer and blocks at least one of holes, electrons and excitons.

For instance, when the blocking layer is provided in contact with the cathode-side of the emitting layer, the blocking layer permits transport of electrons, but prevents holes from reaching a layer provided near the cathode (e.g., the electron transporting layer) beyond the blocking layer. When the organic EL device includes an electron transporting layer, the blocking layer is preferably interposed between the emitting layer and the electron transporting layer.

When the blocking layer is provided in contact with the emitting layer near the anode, the blocking layer permits transport of holes, but prevents electrons from reaching a layer provided near the anode (e.g., the hole transporting layer) beyond the blocking layer. When the organic EL device includes a hole transporting layer, the blocking layer is preferably interposed between the emitting layer and the hole transporting layer.

Further, a blocking layer may be provided in contact with the emitting layer to prevent an excitation energy from leaking from the emitting layer into a layer in the vicinity thereof. Excitons generated in the emitting layer are prevented from moving into a layer provided near the electrode (e.g., an electron transporting layer and a hole transporting layer) beyond the blocking layer.

The emitting layer and the blocking layer are preferably bonded to each other.

Further, the specific arrangement and disposition for practicing the invention may be altered to other arrangements and treatments as long as such other arrangements and dispositions are compatible with the invention.

EXAMPLES

Synthesis Example 1(Synthesis of Compound BD)

(1) Synthesis of Compound (1-1)

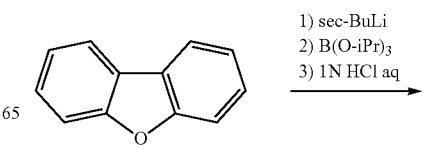

[Formula 62]

1) sec-BuLi
2) B(O-iPr)$_3$
3) 1N HCl aq

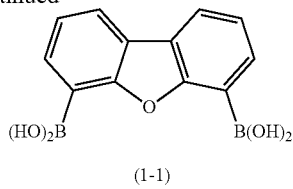

(1-1)

Dibenzofuran (20.0 g, 80.9 mmol) and dehydrated tetrahydrofuran (200 ml) were put into a three-necked flask as a reactor. Under a nitrogen gas atmosphere, the reactor was cooled to minus 70 degrees C. 1.68 M s-butyllithium hexane solution (53 ml, 88.9 mmol) was dropped into the reactor and stirred at minus 70 degrees C. for one hour. Subsequently, triisopropyl borate (37.3 ml, 162 mmol) was further added to the reactor and stirred at the room temperature for six hours. After the reaction was over, an aqueous solution of 1N HCl (100 ml) was added to the reactor and stirred for 30 minutes. Subsequently, the obtained sample solution was transferred to a separating funnel and extracted with dichloromethane for several times. The extracted solution was dried, filtrated and condensed with anhydrous magnesium sulfate. A solid obtained after condensation was dispersed and washed in hexane to obtain a white solid. A yield of the compound was 15.9 g and a yield rate thereof was 93%.

(2) Synthesis of Compound (1-2)

[Formula 63]

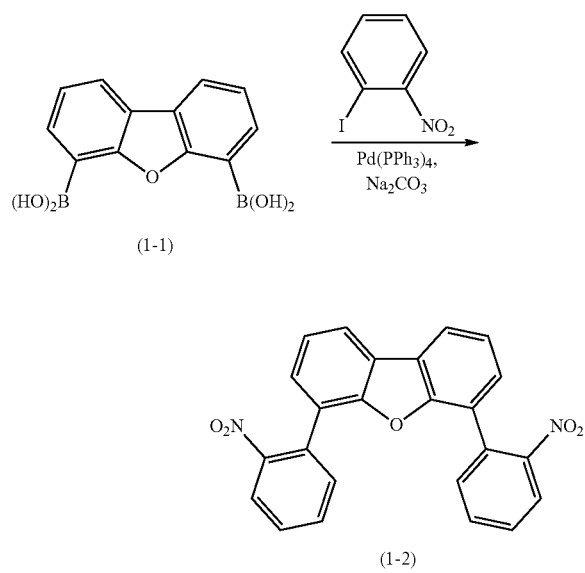

The compound (1-1) (25.0 g, 97.7 mmol), 2-iodonitrobenzene (74.7 g, 300 mmol), 2M sodium carbonate solution (250 mL), 1,2-dimethoxyethane (500 mL), and Pd(PPh₃)₄ (2.30 g, 1.95 mmol) were put into a three-necked flask and refluxed for 12 hours under a nitrogen gas atmosphere. After the reaction was over, the sample solution was filtrated. The obtained solid was washed with methanol and hexane. A yield of the compound was 26.5 g and a yield rate thereof was 66%.

(3) Synthesis of Compound (1-3)

[Formula 64]

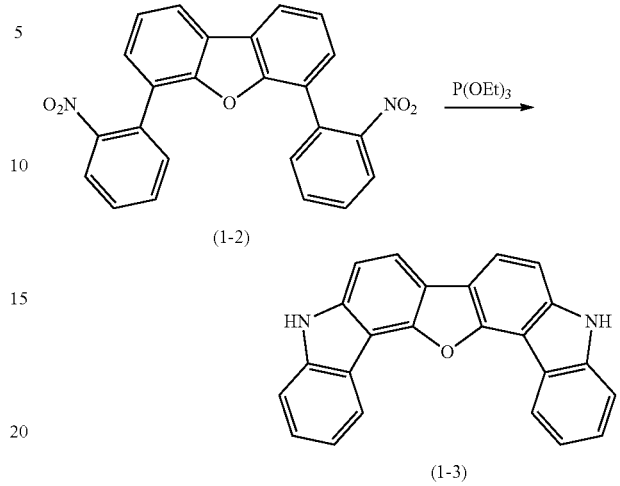

A compound (1-3) (26.5 g, 64.6 mmol) and triethyl phosphite (430 ml) were added to a three-necked flask and heated with stirring at 170 degrees C. for 16 hours.

After the reaction was over, the reactant was distilled. Remaining triethyl phosphite and a residue of triethyl phosphite were eliminated. The obtained organic layer was refined by silica-gel chromatography to provide a light-yellow solid. In the refinement by silica-gel column chromatography, the solvent mixture of hexane and dichloromethane was used as an eluent. A mixing ratio of the solvent mixture, specifically, hexane:dichloromethane was gradually changed in the order of 10:1, 5:1 and 1:1 to elute a target substance.

A yield of the compound was 12.1 g and a yield rate thereof was 54%.

(4) Synthesis of Compound (1-4)

[Formula 65]

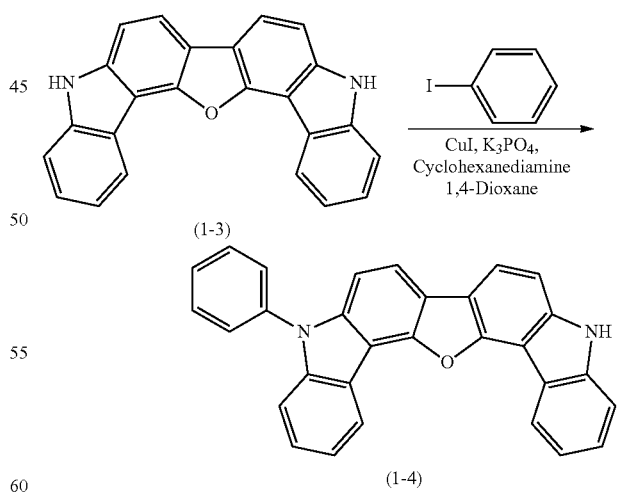

The compound (1-3) (3.46 g, 10 mmol), iodobenzene (2.04 g, 10 mmol), copper iodide (1.90 g, 10 mmol), tripotassium phosphate (4.24 g, 20 mmol), cyclohexane diamine (2.28 g, 20 mmol) and 1,4-dioxane (30 mL) were put into a three-necked flask and refluxed for 12 hours under a nitrogen gas atmosphere.

After the reaction was over, undissolved substance was separated by filtration using Celite (registered trademark). The filtrate was transferred to a separating funnel and extracted with dichloromethane for several times. The obtained organic layer was dried, filtrated and condensed with anhydrous magnesium sulfate. The condensed crude product was refined by silica-gel column chromatography, so that a white solid was obtained. In the refinement by silica-gel column chromatography, the solvent mixture of hexane and dichloromethane was used as an eluent. A mixing ratio of the solvent mixture, specifically, hexane:dichloromethane was gradually changed in the order of 10:1 and 5:1 to elute a target substance. A yield of the compound was 3.38 g and a yield rate thereof was 40%.

(5) Synthesis of Compound BD

A compound (1-4) (2.11 g, 5 mmol), an intermediate A (1.94 g, 5 mmol), $Pd_2(dba)_3$ (90 mg, 0.1 mmol), tri-t-butylphosphonium tetrafluoroborate (0.12 g, 0.4 mmol), sodium t-butoxide (0.67 g, 7 mmol), dehydrated toluene (100 mL) were put into a three-necked flask and refluxed for 48 hours under an argon gas atmosphere.

After the reaction was over, the obtained sample solution was added to toluene (5000 mL) and heated to 110 degrees C. Undissolved substance was separated by filtration through Celite and silica gel. A solid obtained by condensing the filtrate was repeatedly washed with toluene to provide a target substance (compound BD) in the form of solid. A yield of the compound was 2.77 g and a yield rate thereof was 76%. FD-MS (Field Desorption Mass Spectrometry) analysis consequently showed that m/e was equal to 729 while a molecular weight was 729.

[Formula 66]

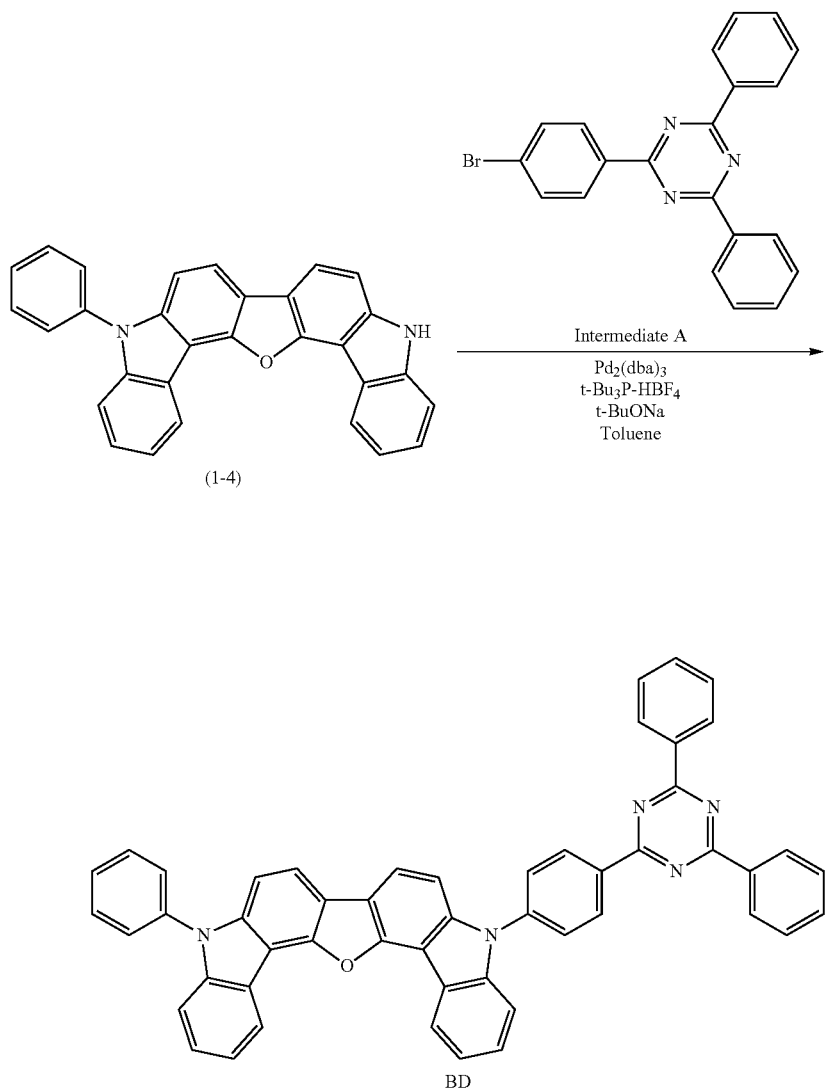

Synthesis Example 2(Synthesis of Compound 2)

[Formula 67]

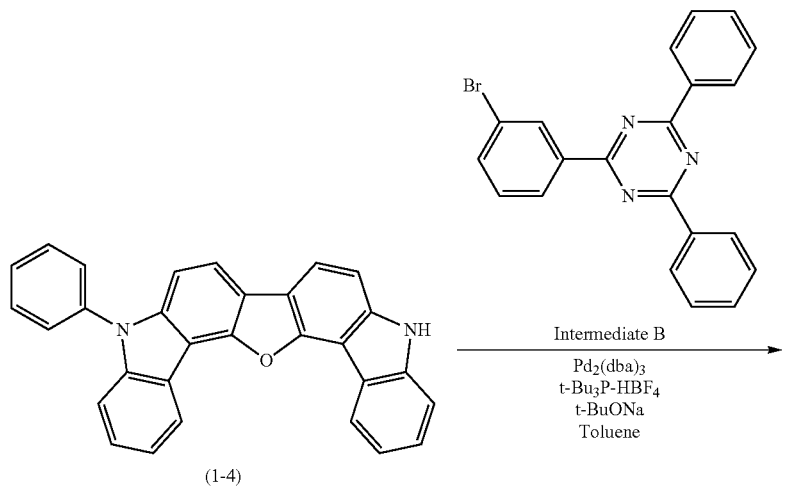

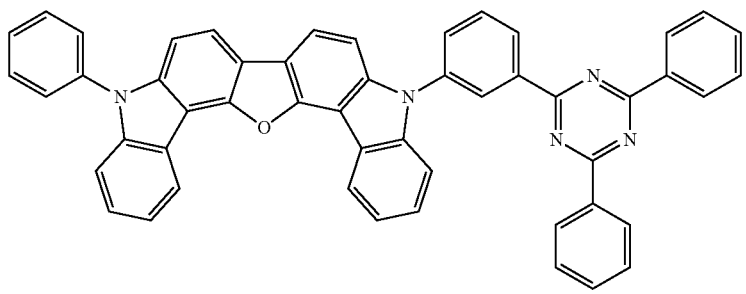

Compound 2

The compound (1-4) (2.11 g, 5 mmol), an intermediate B (1.94 g, 5 mmol) synthesized by the method described in WO2011-132683, Pd$_2$(dba)$_3$ (90 mg, 0.1 mmol), tri-t-butyl-phosphonium tetrafluoroborate (0.12 g, 0.4 mmol), sodium t-butoxide (0.67 g, 7 mmol), dehydrated toluene (100 mL) were put into a three-necked flask and refluxed for 48 hours under an argon gas atmosphere.

After the reaction was over, the reaction solution was added to toluene (3000 mL) and heated to 110 degrees C. Undissolved substance was separated by filtration through Celite and silica gel. A solid obtained by condensing the filtrate was repeatedly washed with toluene to provide a target substance (compound 2) in the form of a light-yellow solid. A yield of the compound was 2.35 g and a yield rate thereof was 64%. FD-MS analysis consequently showed that m/e was equal to 729 while a calculated molecular weight was 729.

Synthesis Example 3(Synthesis of Compound 3)

(1) Synthesis of Intermediate C

[Formula 68]

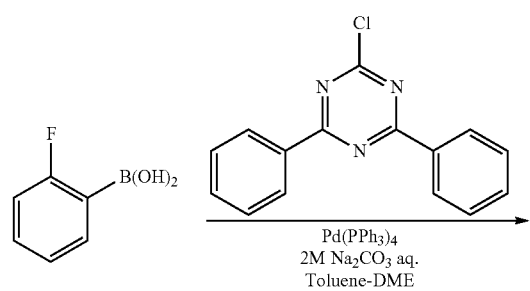

-continued

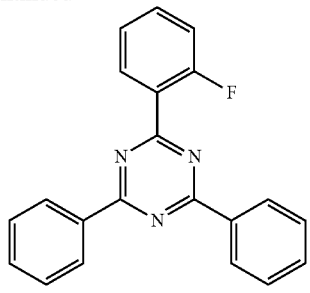

Intermediate C 2-fluorophenylboronic acid (7.0 g, 50 mmmol), 2-chloro-4,6-diphenyltriazine (13.4 g, 50mmol), 2M sodium carbonate solution (62.5 mL), 1,2-dimethoxyethane (DME) (100 mL) and toluene (100 mL) were added to a three-necked flask. Next, tetrakis (triphenylphosphine) palladium 1.73g (1.5 mmol) was further added to flask and headed for reflux with stirring for eight hours under an argon gas atmosphere. After the mixture solution was headed for reflux with stirring, an organic layer was extracted and condensed under reduced pressure. The residue obtained by condensing the organic layer was refined by silica-gel column chromatography (toluene solvent). The obtained solid was suspended in and washed with methanol to provide an intermediate C in the form of a white solid. A yield of the compound was 11.6 g and a yield rate thereof was 71 %.

(2) Synthesis of Compound 3

[Formula 69]

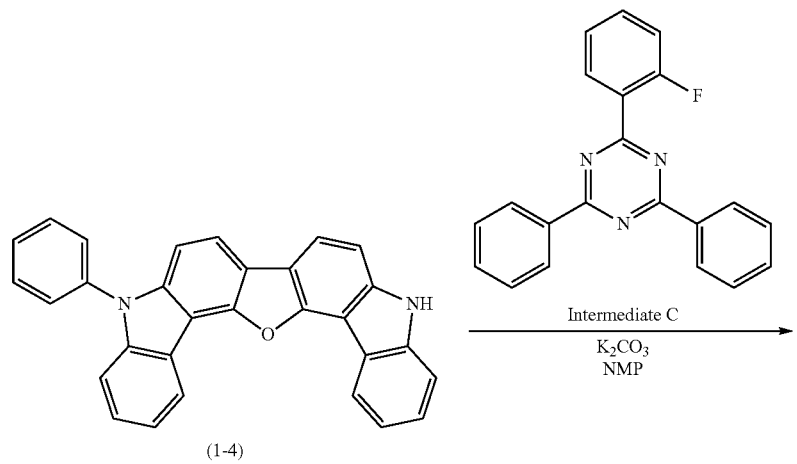

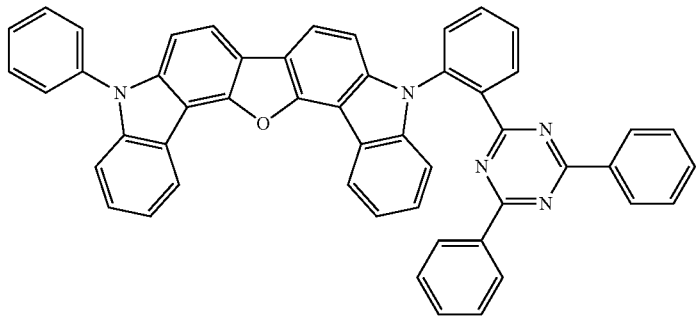

Compound 3

The compound (1-4) (1.5 g, 3.55 mmol), the intermediate C (1.4 g, 4.28 mmol), potassium carbonate (0.6 g, 4.34 mmol), and N-methyl-2-pyrrolidone (NMP) (20 mL) were added to a three-necked flask and heated with stirring at 150 degrees C. for 24 hours under an argon gas atmosphere. The reaction solution was added to water (200 mL) to precipitate solid. Then, the precipitated solid was separated by filtration. Next, the obtained solid by filtration was suspended in acetone and heated at 60 degrees C. with stirring. Undissolved substance (target substance) was separated by filtration to provide the target substance (compound 3) in the form of a light-yellow solid. A yield of the compound was 2.5 g and a yield rate thereof was 96%. FD-MS analysis consequently showed that m/e was equal to 729 while a calculated molecular weight was 729.

Synthesis Example 4(Synthesis of Compound 4)

The compound (1-4) (2.11 g, 5 mmol), an intermediate D (1.74 g, 4.5 mmol) synthesized by the method described in WO2003-080760, $Pd_2(dba)_3$ (90 mg, 0.1 mmol), tri-t-butyl-phosphonium tetrafluoroborate (0.12 g, 0.4 mmol), sodium t-butoxide (0.67 g, 7 mmol), dehydrated toluene (50 mL) were put into a three-necked flask and refluxed for 10 hours under an argon gas atmosphere.

After the reaction was over, the reaction solution was added to toluene (5000 mL) and heated to 110 degrees C. Undissolved substance was separated by filtration through Celite and silica gel. A solid obtained by condensing the filtrate was repeatedly washed with toluene to provide a target substance (compound 4) in the form of a light-yellow solid. A yield of the compound was 1.55 g and a yield rate thereof was 47%. FD-MS analysis consequently showed that m/e was equal to 728 while a calculated molecular weight was 728.

[Formula 70]

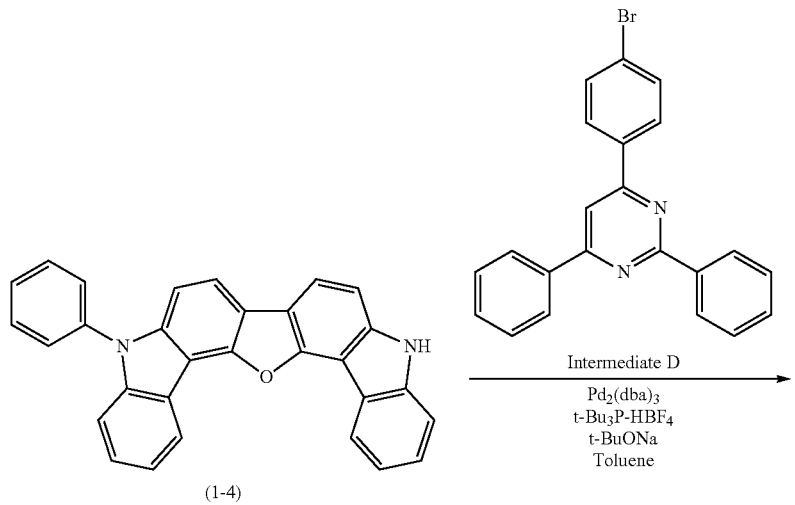

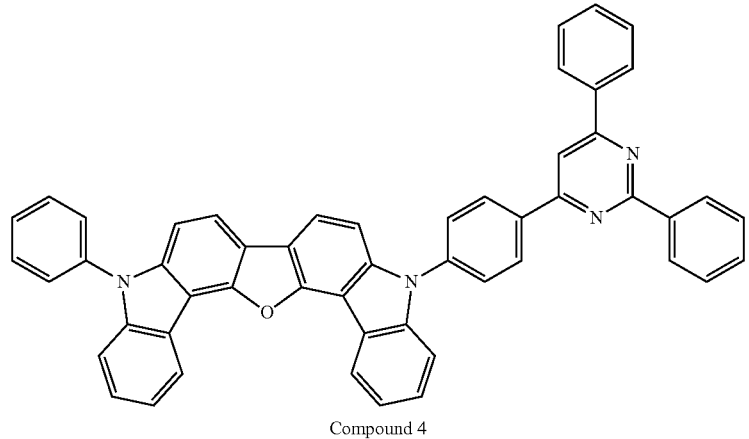

Compound 4

Synthesis Example 5 (Synthesis of Compound 5)

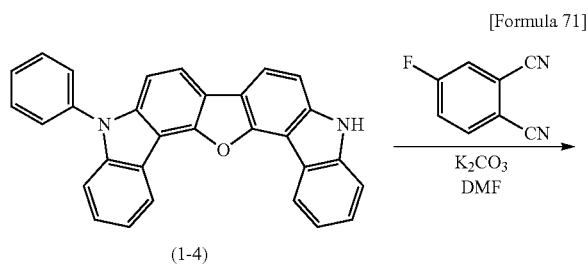

[Formula 71]

(1-4)

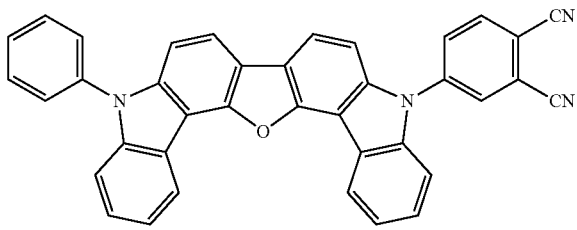

Compound 5

The compound (1-4) (4.2 g, 10 mmol), 4-fluorophthalonitrile (1.75 g, 12 mmol), potassium carbonate (2.1 g, 15 mmol), and N,N-dimethylformamido (DMF) (25 mL) were added to a three-necked flask and heated with stirring at 80 degrees C. for 10 hours under an argon gas atmosphere. After the reaction was over, methanol (100 mL) and acetone (50 mL) were added to the reaction solution to precipitate a solid. Then, the precipitated solid was filtrated. Next, the solid was repeatedly washed with water to eliminate an inorganic salt, so that a target substance (compound 5) in the form of a yellow solid was obtained. A yield of the compound was 4.8 g and a yield rate thereof was 87%. FD-MS analysis consequently showed that m/e was equal to 548 while a calculated molecular weight was 548.

Synthesis Example 6 (Synthesis of Compound 6)

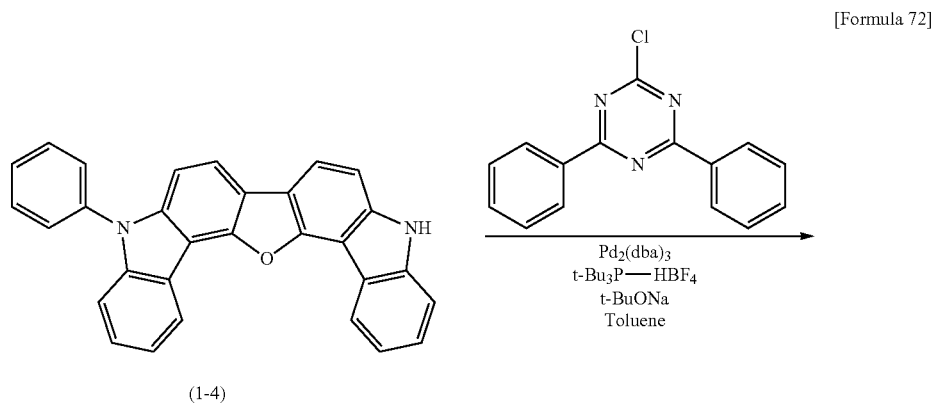

[Formula 72]

(1-4)

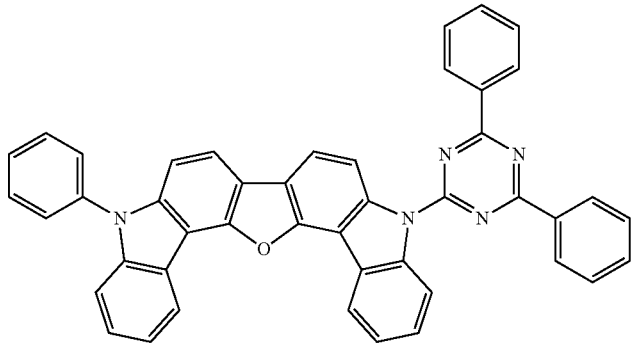

Compound 6

The compound (1-4) (3.0 g, 7.1 mmol), 2-chloro-4,6-diphenyltriazine (1.9 g, 7.1 mmol), Pd$_2$(dba)$_3$ (0.16 g, 0.14 mmol), tri-t-butylphosphonium tetrafluoroborate (0.01 oz, 0.55 mmol), sodium t-butoxide (0.96 g, 10 mmol), dehydrated toluene (300 mL) were put into a three-necked flask and refluxed for 12 hours under an argon gas atmosphere.

After the reaction was over, the reaction solution was added to toluene (7000 mL) and heated to 110 degrees C. Undissolved substance was separated by filtration through Celite and silica gel. A solid obtained by condensing the filtrate was repeatedly washed with toluene to provide a target substance (compound 6) in the form of a light-yellow solid. A yield of the compound was 2.0 g and a yield rate thereof was 43%. FD-MS analysis consequently showed that m/e was equal to 653 while a calculated molecular weight was 653.

Synthesis Example 7 (Synthesis of Compound 7)

(1) Synthesis of Intermediate E

[Formula 73]

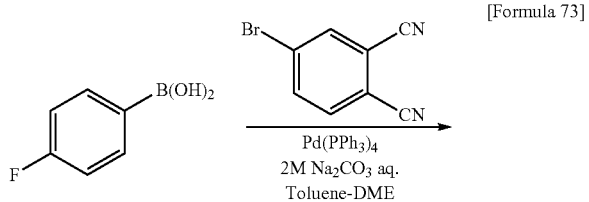

the mixture solution was headed for reflux with stirring, an organic layer was extracted and condensed under reduced pressure. The residue obtained by condensing the organic layer was refined by silica-gel column chromatography (dichloromethane solvent). The obtained solid was suspended in and washed with methanol to provide an intermediate E in the form of a light-yellow solid. A yield of the compound was 9.3 g and a yield rate thereof was 84%.

(2) Synthesis of Compound 7

[Formula 74]

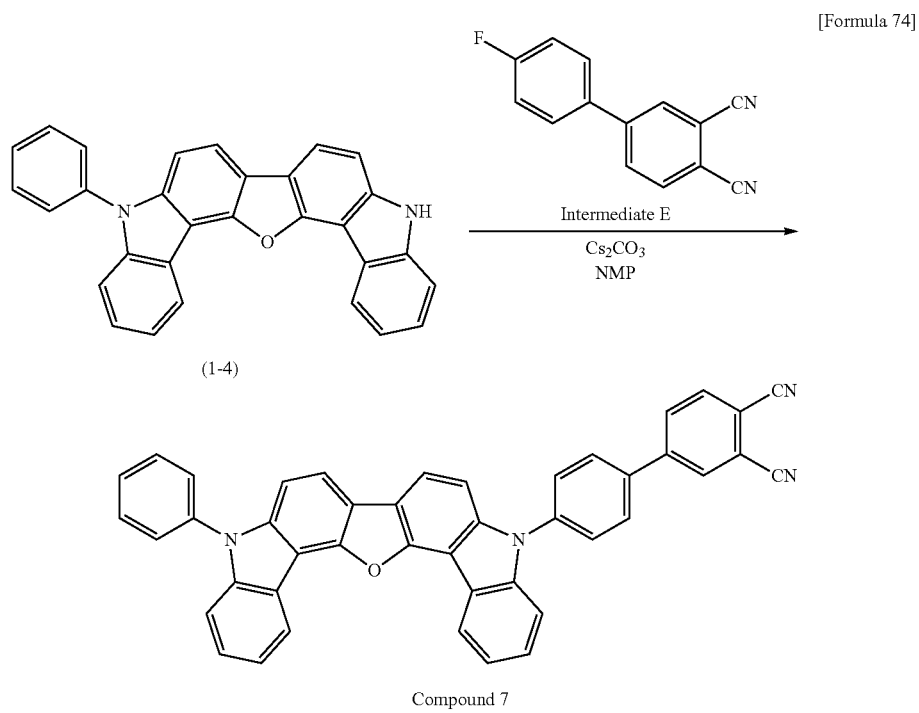

-continued

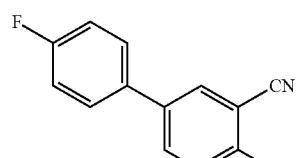

Intermediate E 4-fluorophenylboronic acid (7.0 g, 50 mmol), 4-bromophthalonitrile (10.3 g, 50 mmol), 2M sodium carbonate solution (62.5 mL), 1,2-dimethoxyethane (DME) (100 mL) and toluene (100 mL) were added to a three-necked flask. Next, tetrakis (triphenylphosphine) palladium 1.73 (1.5 mmol) was further added to flask and headed for reflux with stirring for six hours under an argon gas atmosphere. After The compound (1-4) (4.2 g, 10 mmol), an intermediate E (2.2 g, 10 mmol), cesium carbonate (4.9 g, 15 mmol), and N-methyl-2-pyrrolidone (NMP) (30 mL) were added to a three-necked flask and heated with stirring at 130 degrees C. for 10 hours under an argon gas atmosphere. After the reaction was over, the reaction solution was added to water (500 mL) to precipitate solid. Then, the precipitated solid was filtrated. Next, the obtained solid by filtration was suspended in acetone and heated at 60 degrees C. with stirring. Undissolved substance (target substance) was separated by filtration to provide the target substance (compound 7) in the form of a light-yellow solid. A yield of the compound was 3.1 g and a yield rate thereof was 49%. As a result of FD-MS analysis, m/e was equal to 624 while a calculated molecular weight was 624.

Description of Examples will be made below. However, the invention is not limited to these Examples.

Compounds used for preparing the organic EL device are shown below.

[Formula 75]
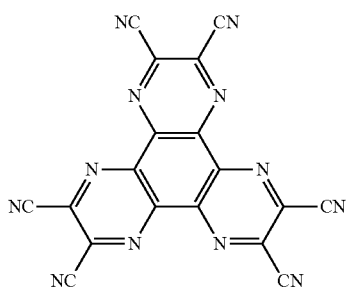
HI
[Formula 76]
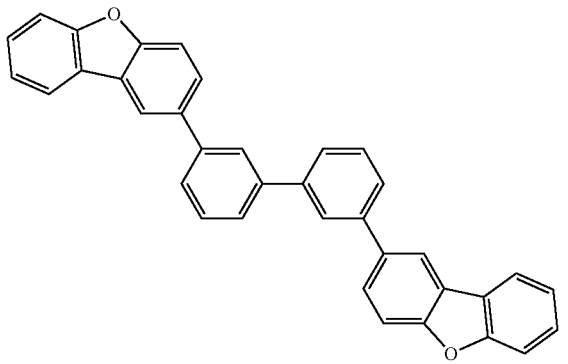
BH
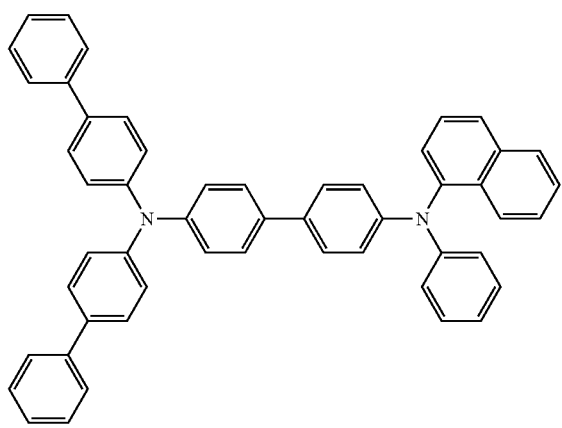
HT-1
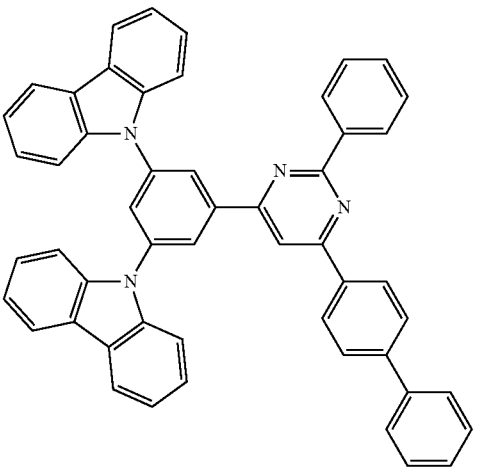
BD
[Formula 77]
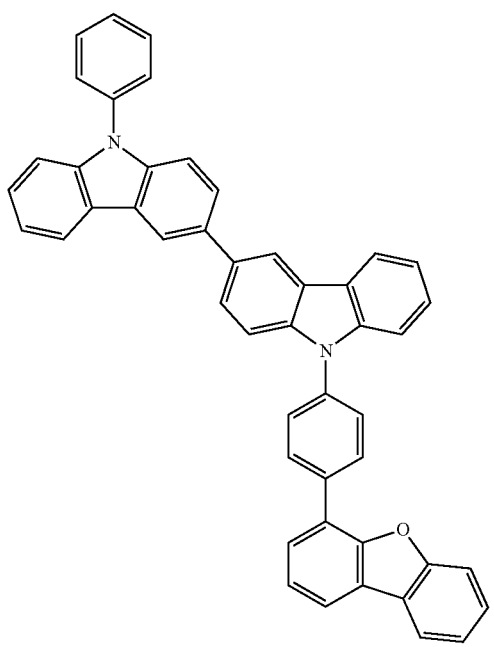
HT-2
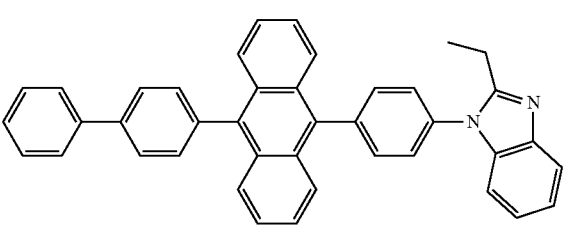
HB-1
ET

[Formula 78]

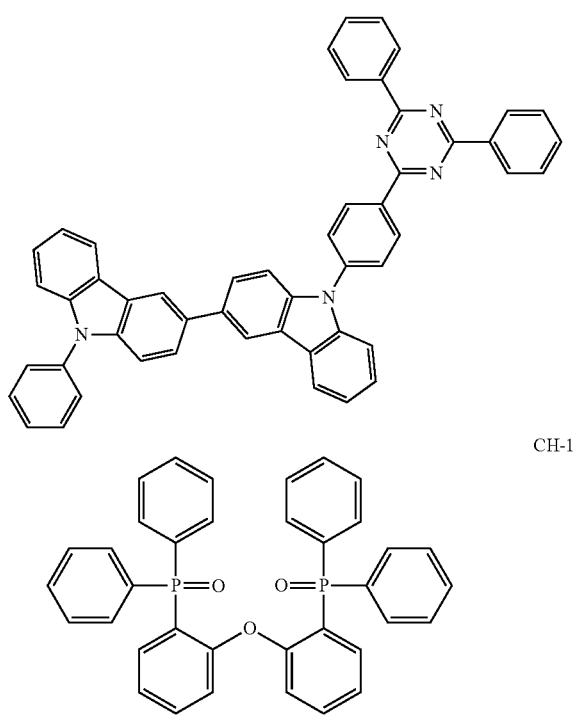

Evaluation of Compounds

Next, properties of the compounds used in Example were measured. A measurement method and a calculation method are shown below.

Delayed Fluorescence

Delayed fluorescence was checked by measuring transitional PL using the device shown in FIG. 2. A sample was prepared by co-depositing the compounds BD and TH-2 on a quartz substrate at a ratio of the compound BD of 12 mass % to form a 100-nm-thick thin film. After the compound BD are excited with pulse light (light irradiated from the pulse laser) having a wavelength to be absorbed in the measurement target compounds, Prompt Emission that is immediately observed in the excited state and Delay Emission that is not observed immediately after the excitation and is later observed are present. The delayed fluorescence in the exemplary embodiment means that an amount of Delay Emission is 5% or more based on an amount of Prompt Emission. It was found that the amount of Delay Emission was 5% or more based on the amount of Prompt Emission in the compound BD. The amount of Prompt Emission and the amount of Delay Emission can be obtained according to the method as a method described in "Nature 492, 234-238, 2012." A device used for calculating the amounts of Prompt Emission and Delay Emission is not limited to the device of FIG. 2 and a device described in the above document.

Preparation and Evaluation of Organic EL Device

The organic EL device was prepared and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound HI was vapor-deposited on a surface of the glass substrate where the transparent electrode line was provided in a manner to cover the transparent electrode, thereby forming a 5-nm-thick hole injecting layer.

Next, the compound HT-1 was vapor-deposited on the hole injecting layer to form a 80-nm-thick first hole transporting layer on the HI film.

Next, the compound HT-2 was deposited on the first hole transporting layer to form a 15-nm-thick second hole transporting layer.

Further, the compound BD (the first compound) and a compound BH (the second compound) were co-deposited on a second hole transporting layer to form a 25-nm-thick emitting layer. The concentration of the compound BD in the emitting layer was set at 24 mass % and the concentration of the compound BH in the emitting layer was set at 76 mass %.

The compound HB-1 was then vapor-deposited on the emitting layer to form a 5-nm-thick blocking layer.

Next, a compound ET-1 was deposited on the blocking layer to form a 20-nm-thick electron transporting layer.

Lithium fluoride (LiF) was then deposited on the electron transporting layer to form a 1-nm-thick electron injecting electrode (cathode).

A metal aluminum (Al) was then deposited on the electron injecting electrode to form an 80-nm-thick metal Al cathode.

A device arrangement of the organic EL device of Example 1 is shown in symbols as follows.

ITO(130)/HI(5)/HT-1(80)/HT-2(15)/BH:BD (25, 76%: 24%)/HB-1(5)/ET(20)/LiF(1)/Al(80)

Numerals in parentheses represent a film thickness (unit: nm). The numerals in the form of percentage in parentheses indicate ratios (mass %) of the materials in the emitting layer.

Example 2

An organic EL device of Example 2 was prepared in the same manner as the organic EL device of Example 1 except that a concentration of the compound BD was determined at 50 mass % and a concentration of the compound BH was determined at 50 mass % in the emitting layer of Example 1.

A device arrangement of the organic EL device of Example 2 is shown in symbols as follows.

ITO(130)/HI(5)/HT-1(80)/HT-2(15)/BH:BD (25, 50%: 50%)/HB-1(5)/ET(20)/LiF(1)/Al(80)

Comparative 1

An organic EL device of Comparative 1 was prepared in the same manner as the organic EL device of Example 1 except that a compound CD-1 was used in place of the compound BD in the emitting layer of Example 1.

A device arrangement of the organic EL device in Comparative 1 is shown in symbols as follows.

ITO(130)/HI(5)/HT-1(80)/HT-2(15)/BH:CD-1 (25, 76%: 24%)/HB-1(5)/ET(20)/LiF(1)/Al(80)

Comparative 2

An organic EL device of Comparative 2 was prepared in the same manner as the organic EL device of Example 2 except that a compound CD-1 was used in place of the compound BD in the emitting layer of Example 2.

A device arrangement of the organic EL device in Comparative 2 is shown in symbols as follows.

ITO(130)/HI(5)/HT-1(80)/HT-2(15)/BH:CD-1 (25, 50%: 50%)/HB-1(5)/ET(20)/LiF(1)/Al(80)

Comparative 3

An organic EL device of Comparative 3 was prepared in the same manner as the organic EL device of Example 1 except that a compound CH-1 was used in place of the compound BH and the compound CH-1 was used in place of the compound HB-1 in the emitting layer of Example 1.

A device arrangement of the organic EL device in Comparative 3 is shown in symbols as follows.

ITO(130)/HI(5)/HT-1(80)/HT-2(15)/CH-1:BD (25, 76%: 24%)/CH-1(5)/ET(20)/LiF(1)/Al(80)

Comparative 4

An organic EL device of Comparative 4 was prepared in the same manner as the organic EL device of Example 2 except that the compound CH-1 was used in place of the compound BH and the compound CH-1 was used in place of the compound HB-1 in the emitting layer of Example 2.

A device arrangement of the organic EL device in Comparative 4 is shown in symbols as follows.

ITO(130)/HI(5)/HT-1(80)/HT-2(15)/CH-1:BD (25, 50%: 50%)/CH-1(5)/ET(20)/LiF(1)/Al(80)

Evaluation of Organic EL Devices

The prepared organic EL devices of Examples 1 and 2 and Comparatives 1 to 4 were evaluated as follows. The evaluation results are shown in Table 1.

Drive Voltage

Voltage was applied between ITO transparent electrode and Al metal cathode such that a current density was 1 mA/cm² or 10 mA/cm² where the voltage (unit: V) was measured.

Luminance and CIE1931 Chromaticity

Voltage was applied on each of the organic EL devices such that the current density was 1 mA/cm² or 10 mA/cm², where luminance and CIE1931 chromaticity coordinates (x, y) were measured using a spectroradiometer CS-1000 (manufactured by Konica Minolta Holdings, Inc.).

Current Efficiency L/J and Power Efficiency η

Voltage was applied on each of the organic EL devices such that the current density was 1 mA/cm² or 10 mA/cm², where spectral-radiance spectra were measured using the above spectroradiometer. A current efficiency (unit: cd/A) and power efficiency η (unit: lm/W) were calculated from the obtained spectral radiance spectra.

Main Peak Wavelength $\lambda_p$

A main peak wavelength $\lambda_p$ was calculated based on the obtained spectral-radiance spectra.

External Quantum Efficiency EQE

Voltage was applied on each of the organic EL devices such that the current density was 1 mA/cm² or 10 mA/cm², where spectral-radiance spectra were measured using the above spectroradiometer. The external quantum efficiency EQE (unit: %) was calculated based on the obtained spectral-radiance spectra, assuming that the spectra were provided under a Lambertian radiation.

TABLE 1

|  | Current Density [mA/cm²] | Voltage [V] | Luminance [cd/m²] | Chromaticity x | Chromaticity y | L/J [cd/A] | η [lm/W] | EQE [%] | λp [nm] |
|---|---|---|---|---|---|---|---|---|---|
| Example 1 | 1 | 3.74 | 397.4 | 0.212 | 0.433 | 39.74 | 33.40 | 16.06 | 491 |
|  | 10 | 4.57 | 3322.5 | 0.209 | 0.423 | 33.23 | 22.85 | 13.62 | 489 |
| Example 2 | 1 | 3.30 | 540.3 | 0.244 | 0.489 | 54.03 | 51.40 | 19.97 | 497 |
|  | 10 | 3.99 | 4172.1 | 0.240 | 0.482 | 41.72 | 32.82 | 15.58 | 496 |
| Comp. 1 | 1 | 3.61 | 154.4 | 0.169 | 0.283 | 15.44 | 13.42 | 8.14 | 477 |
|  | 10 | 4.39 | 1278.1 | 0.166 | 0.266 | 12.78 | 9.15 | 7.02 | 475 |
| Comp. 2 | 1 | 3.10 | 254.9 | 0.183 | 0.339 | 25.49 | 25.87 | 12.01 | 481 |
|  | 10 | 3.76 | 1755.4 | 0.177 | 0.317 | 17.55 | 14.66 | 8.63 | 481 |
| Comp. 3 | 1 | 4.55 | 261.5 | 0.258 | 0.489 | 26.15 | 18.07 | 9.59 | 500 |
|  | 10 | 5.89 | 1809.3 | 0.255 | 0.483 | 18.09 | 9.66 | 6.69 | 499 |
| Comp. 4 | 1 | 3.70 | 262.5 | 0.291 | 0.529 | 26.25 | 22.26 | 9.05 | 508 |
|  | 10 | 4.74 | 1476.5 | 0.285 | 0.521 | 14.76 | 9.79 | 5.15 | 506 |

Lifetime LT80

A voltage was applied on the organic EL devices such that an initial luminance was 1000 cd/m², where a time (unit: hrs) elapsed before a luminance was reduced to 80% of the initial luminance was measured and the measured time was defined as lifetime (LT80).

The lifetime (LT80) of the organic EL device in Example 1 was 193 hours.

The lifetime (LT80) of the organic EL device in Example 2 was 260 hours.

The lifetime (LT80) of the organic EL device in Comparative 3 was less than one hour.

The lifetime (LT80) of the organic EL device in Comparative 4 was less than one hour.

It was recognized that the organic EL device of Examples 1 and 2 emitted light at a high efficiency and with a long lifetime.

Examples 3 to 14

Organic EL devices in Examples 3 to 14 were prepared using the following compounds in addition to the compounds used in the above Examples.

[Formula 79]

BH2
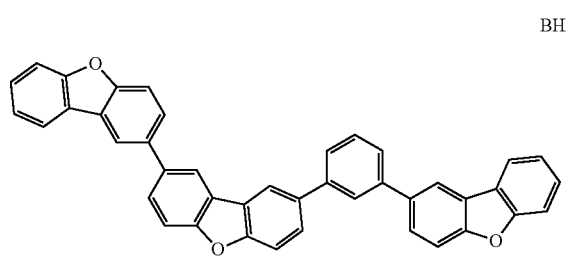

BH3
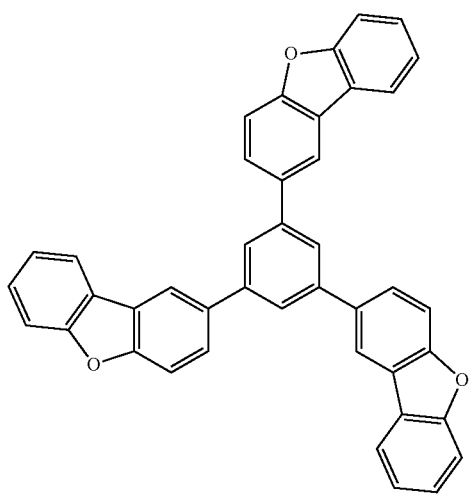

BH4
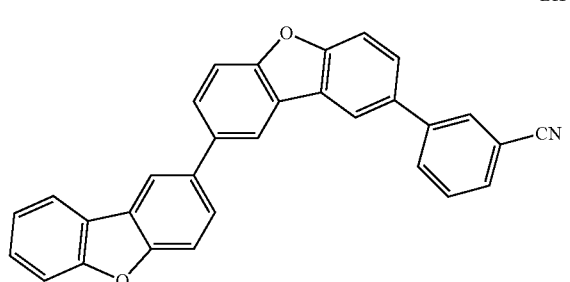

BH5
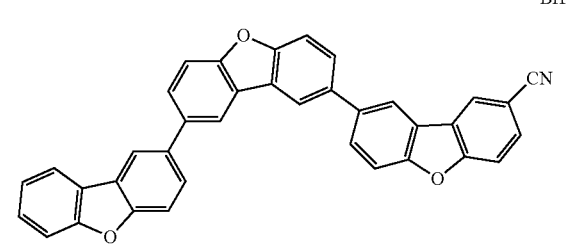

BH6
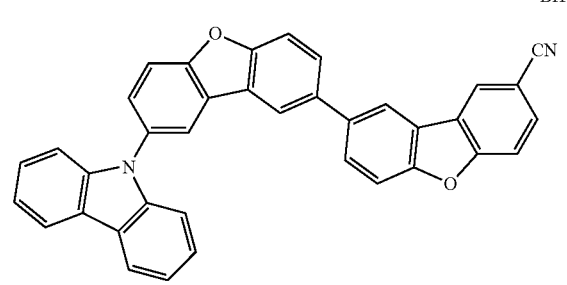

BH7
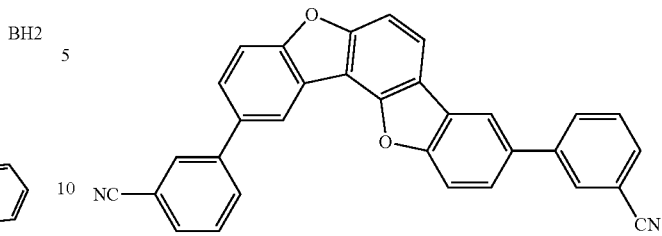

Example 3

An organic EL device of Example 3 was prepared in the same manner as the organic EL device of Example 1 except that a compound BH2 was used in place of the compound BH in the emitting layer of Example 1.

A device arrangement of the organic EL device of Example 3 is shown in symbols as follows.

ITO(130)/HI(5)/HT-1(80)/HT-2(15)/BH2:BD (25, 76%: 24%)/HB-1(5)/ET(20)/LiF(1)/Al(80)

Example 4

An organic EL device of Example 4 was prepared in the same manner as the organic EL device of Example 3 except that the concentration of the compound BD was determined at 50 mass % and a concentration of the compound BH2 was determined at 50 mass % in the emitting layer of Example 3.

A device arrangement of the organic EL device of Example 4 is shown in symbols as follows.

ITO(130)/HI(5)/HT-1(80)/HT-2(15)/BH2:BD (25, 50%: 50%)/HB-1(5)/ET(20)/LiF(1)/Al(80)

Example 5

An organic EL device of Example 5 was prepared in the same manner as the organic EL device of Example 1 except that a compound BH3 was used in place of the compound BH in the emitting layer of Example 1.

A device arrangement of the organic EL device of Example 5 is shown in symbols as follows.

ITO(130)/HI(5)/HT-1(80)/HT-2(15)/BH3:BD (25, 76%: 24%)/HB-1(5)/ET(20)/LiF(1)/Al(80)

Example 6

An organic EL device of Example 6 was prepared in the same manner as the organic EL device of Example 5 except that the concentration of the compound BD was determined at 50 mass % and a concentration of the compound BH3 was determined at 50 mass % in the emitting layer of Example 5.

A device arrangement of the organic EL device of Example 6 is shown in symbols as follows.

ITO(130)/HI(5)/HT-1(80)/HT-2(15)/BH3:BD (25, 50%: 50%)/HB-1(5)/ET(20)/LiF(1)/Al(80)

Example 7

An organic EL device of Example 7 was prepared in the same manner as the organic EL device of Example 1 except that a compound BH4 was used in place of the compound BH in the emitting layer of Example 1.

A device arrangement of the organic EL device of Example 7 is shown in symbols as follows.

ITO(130)/HI(5)/HT-1(80)/HT-2(15)/BH4:BD (25, 76%: 24%)/HB-1(5)/ET(20)/LiF(1)/Al(80)

Example 8

An organic EL device of Example 8 was prepared in the same manner as the organic EL device of Example 7 except that the concentration of the compound BD was determined at 50 mass % and a concentration of the compound BH4 was determined at 50 mass % in the emitting layer of Example 7.

A device arrangement of the organic EL device of Example 8 is shown in symbols as follows.

ITO(130)/HI(5)/HT-1(80)/HT-2(15)/BH4:BD (25, 50%: 50%)/HB-1(5)/ET(20)/LiF(1)/Al(80)

Example 9

An organic EL device of Example 9 was prepared in the same manner as the organic EL device of Example 1 except that a compound BH5 was used in place of the compound BH in the emitting layer of Example 1.

A device arrangement of the organic EL device of Example 9 is shown in symbols as follows.

ITO(130)/H1(5)/HT-1(80)/HT-2(15)/BH5:BD (25, 76%: 24%)/HB-1(5)/ET(20)/LiF(1)/Al(80)

Example 10

An organic EL device of Example 10 was prepared in the same manner as the organic EL device of Example 9 except that the concentration of the compound BD was determined at 50 mass % and a concentration of the compound BH5 was determined at 50 mass % in the emitting layer of Example 9.

A device arrangement of the organic EL device of Example 10 is shown in symbols as follows.

ITO(130)/HI(5)/HT-1(80)/HT-2(15)/BH5:BD (25, 50%: 50%)/HB-1(5)/ET(20)/LiF(1)/Al(80)

Example 11

An organic EL device of Example 11 was prepared in the same manner as the organic EL device of Example 1 except that a compound BH6 was used in place of the compound BH in the emitting layer of Example 1.

A device arrangement of the organic EL device of Example 11 is shown in symbols as follows.

ITO(130)/HI(5)/HT-1(80)/HT-2(15)/BH6: BD (25, 76%: 24%)/HB-1(5)/ET(20)/LiF(1)/Al(80)

Example 12

An organic EL device of Example 12 was prepared in the same manner as the organic EL device of Example 11 except that the concentration of the compound BD was determined at 50 mass % and a concentration of the compound BH6 was determined at 50 mass % in the emitting layer of Example 11.

A device arrangement of the organic EL device of Example 12 is shown in symbols as follows.

ITO(130)/H1(5)/HT-1(80)/HT-2(15)/BH6:BD (25, 50%: 50%)/HB-1(5)/ET(20)/LiF(1)/Al(80)

Example 13

An organic EL device of Example 13 was prepared in the same manner as the organic EL device of Example 1 except that a compound BH7 was used in place of the compound BH in the emitting layer of Example 1.

A device arrangement of the organic EL device of Example 13 is shown in symbols as follows.

ITO(130)/HI(5)/HT-1(80)/HT-2(15)/BH7: BD (25, 76%: 24%)/HB-1(5)/ET(20)/LiF(1)/Al(80)

Example 14

An organic EL device of Example 14 was prepared in the same manner as the organic EL device of Example 13 except that the concentration of the compound BD was determined at 50 mass % and a concentration of the compound BH7 was determined at 50 mass % in the emitting layer of Example 13.

A device arrangement of the organic EL device of Example 14 is shown in symbols as follows.

ITO(130)/HI(5)/HT-1(80)/HT-2(15)/BH7: BD (25, 50%: 50%)/HB-1(5)/ET(20)/LiF(1)/Al(80)

Evaluation of Organic EL Devices

The organic EL devices prepared in Examples 3 to 14 were evaluated in terms of drive voltage, luminance, CIE1931 chromaticity, current efficiency L/J, power efficiency η, main peak wavelength $\lambda_p$ and external quantum efficiency EQE. The evaluation method was the same as the above. In Examples 3 to 14, a current density for driving the organic EL devices was determined at 0.10 mA/cm$^2$, 1.00 mA/cm$^2$ or 10 mA/cm$^2$. The results of the evaluation are shown in Table 2.

TABLE 2

|  | Current Density [mA/cm$^2$] | Voltage [V] | Luminance [cd/m$^2$] | Chromaticity x | Chromaticity y | L/J [cd/A] | η [lm/W] | EQE [%] | $\lambda_p$ [nm] |
| --- | --- | --- | --- | --- | --- | --- | --- | --- | --- |
| Example 3 | 0.10 | 2.73 | 45.0 | 0.225 | 0.429 | 45.03 | 51.86 | 17.88 | 489 |
|  | 1.00 | 3.02 | 431.6 | 0.221 | 0.421 | 43.16 | 44.93 | 17.33 | 489 |
|  | 10 | 3.67 | 3293.7 | 0.216 | 0.409 | 32.94 | 28.21 | 13.50 | 487 |
| Example 4 | 0.10 | 2.56 | 55.4 | 0.260 | 0.487 | 55.41 | 67.95 | 20.10 | 499 |
|  | 1.00 | 2.79 | 526.1 | 0.256 | 0.482 | 52.61 | 59.15 | 19.23 | 497 |
|  | 10 | 3.31 | 4041.2 | 0.250 | 0.473 | 40.41 | 38.33 | 14.97 | 496 |
| Example 5 | 0.10 | 2.68 | 45.6 | 0.214 | 0.416 | 45.57 | 53.47 | 18.63 | 488 |
|  | 1.00 | 2.92 | 415.4 | 0.210 | 0.407 | 41.54 | 44.63 | 17.23 | 488 |
|  | 10 | 3.56 | 3043.9 | 0.205 | 0.393 | 30.44 | 26.85 | 12.92 | 484 |

TABLE 2-continued

|  | Current Density [mA/cm$^2$] | Voltage [V] | Luminance [cd/m$^2$] | Chromaticity x | Chromaticity y | L/J [cd/A] | η [lm/W] | EQE [%] | λ$_p$ [nm] |
|---|---|---|---|---|---|---|---|---|---|
| Example 6 | 0.10 | 2.49 | 52.5 | 0.254 | 0.484 | 52.54 | 66.19 | 19.27 | 498 |
|  | 1.00 | 2.69 | 506.6 | 0.250 | 0.479 | 50.66 | 59.16 | 18.72 | 497 |
|  | 10 | 3.24 | 3960.0 | 0.244 | 0.470 | 39.60 | 38.45 | 14.84 | 496 |
| Example 7 | 0.10 | 2.88 | 51.3 | 0.229 | 0.459 | 51.32 | 55.94 | 19.81 | 493 |
|  | 1.00 | 3.28 | 480.6 | 0.224 | 0.451 | 48.06 | 45.98 | 18.78 | 492 |
|  | 10 | 4.13 | 3456.8 | 0.219 | 0.438 | 34.57 | 26.30 | 13.76 | 491 |
| Example 8 | 0.10 | 2.65 | 55.2 | 0.254 | 0.494 | 55.23 | 65.55 | 20.16 | 499 |
|  | 1.00 | 2.95 | 532.0 | 0.250 | 0.489 | 53.20 | 56.64 | 19.56 | 499 |
|  | 10 | 3.57 | 4157.5 | 0.244 | 0.480 | 41.58 | 36.58 | 15.49 | 496 |
| Example 9 | 0.10 | 2.78 | 51.5 | 0.214 | 0.441 | 51.50 | 58.26 | 20.56 | 491 |
|  | 1.00 | 3.28 | 485.3 | 0.211 | 0.434 | 48.53 | 46.51 | 19.58 | 491 |
|  | 10 | 4.24 | 3380.4 | 0.206 | 0.421 | 33.80 | 25.03 | 13.90 | 491 |
| Example 10 | 0.10 | 2.56 | 64.5 | 0.250 | 0.499 | 64.45 | 79.01 | 23.45 | 499 |
|  | 1.00 | 2.97 | 622.4 | 0.245 | 0.493 | 62.24 | 65.78 | 22.84 | 498 |
|  | 10 | 3.75 | 4485.8 | 0.239 | 0.485 | 44.86 | 37.62 | 16.69 | 497 |
| Example 11 | 0.10 | 2.76 | 45.1 | 0.224 | 0.438 | 45.14 | 51.29 | 17.89 | 491 |
|  | 1.00 | 3.13 | 453.7 | 0.219 | 0.429 | 45.37 | 45.59 | 18.22 | 489 |
|  | 10 | 3.85 | 3521.4 | 0.213 | 0.417 | 35.21 | 28.71 | 14.43 | 489 |
| Example 12 | 0.10 | 2.60 | 53.0 | 0.250 | 0.480 | 52.96 | 64.09 | 19.62 | 496 |
|  | 1.00 | 2.90 | 505.9 | 0.247 | 0.476 | 50.59 | 54.87 | 18.86 | 496 |
|  | 10 | 3.49 | 3953.7 | 0.241 | 0.468 | 39.54 | 35.56 | 14.92 | 494 |
| Example 13 | 0.10 | 2.94 | 56.9 | 0.264 | 0.501 | 56.91 | 60.88 | 20.49 | 501 |
|  | 1.00 | 3.52 | 564.6 | 0.259 | 0.496 | 56.46 | 50.40 | 20.48 | 500 |
|  | 10 | 4.52 | 4138.0 | 0.253 | 0.486 | 41.38 | 28.75 | 15.23 | 498 |
| Example 14 | 0.10 | 2.68 | 59.2 | 0.288 | 0.524 | 59.25 | 69.39 | 20.52 | 506 |
|  | 1.00 | 3.15 | 605.2 | 0.283 | 0.520 | 60.52 | 60.38 | 21.08 | 504 |
|  | 10 | 3.93 | 4612.9 | 0.276 | 0.513 | 46.13 | 36.83 | 16.24 | 504 |

It was recognized that the organic EL device of Examples 3 to 14 emitted light at a high efficiency and with a long lifetime.

The invention claimed is:

1. An organic electroluminescence device, comprising:
an anode;
an emitting layer; and
a cathode,
wherein
wherein the emitting layer contains no metal complex,
the emitting layer comprises a first compound and a second compound,
the first compound is a delayed-fluorescent compound represented by a formula (1) below,
the first compound has a lower singlet energy than a singlet energy of the second compound, and
the second compound has at least one of a partial structure represented by a formula (21) below and a partial structure represented by a formula (22) below in one molecule,

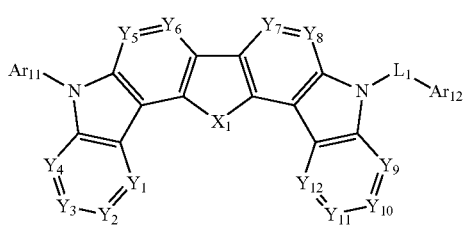

(1)

where:

$Ar_{11}$ and $Ar_{12}$ are each independently a substituted or unsubstituted aromatic hydrocarbon group having 6 to 30 ring carbon atoms, or a substituted or unsubstituted heterocyclic group having 5 to 30 ring atoms;

$L_1$ is a single bond or a linking group, the linking group in $L_1$ being a substituted or unsubstituted aromatic hydrocarbon group having 6 to 30 ring carbon atoms or a substituted or unsubstituted heterocyclic group having 5 to 30 ring atoms;

$Y_1$ to $Y_{12}$ are each independently a nitrogen atom or $CR_1$;

$X_1$ is an oxygen atom, a sulfur atom, N—$R_{10}$, $CR_{11}R_{12}$, $SiR_{13}R_{14}$ or $GeR_{15}R_{16}$;

$R_1$ and $R_{10}$ to $R_{16}$ are each independently a hydrogen atom or a substituent;

when $R_1$ and $R_{10}$ to $R_{16}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group;

a plurality of $R_1$ are optionally mutually the same or different; and when at least two of the plurality of $R_1$ are substituents, the substituents $R_1$ are optionally mutually bonded to form a cyclic structure, (21)

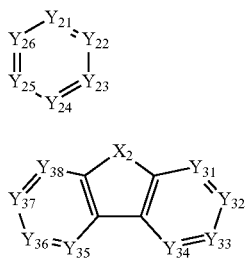

(22)

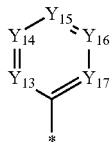

in the formula (21):

$Y_{21}$ to $Y_{26}$ are each independently a nitrogen atom or a carbon atom bonded to another atom in the molecule of the second compound; and at least one of $Y_{21}$ to $Y_{26}$ is a carbon atom bonded to another atom in the molecule of the second compound, and in the formula (22):

$Y_{31}$ to $Y_{38}$ are each independently a nitrogen atom or a carbon atom bonded to another atom in the molecule of the second compound;

at least one of $Y_{31}$ to $Y_{38}$ is a carbon atom bonded to another atom in the molecule of the second compound; and $x_2$ is a nitrogen atom, an oxygen atom or a sulfur atom.

2. The organic electroluminescence device according to claim 1, wherein —$Ar_{11}$ is different from -$L_1$-$Ar_{12}$.

3. The organic electroluminescence device according to claim 1, wherein $Ar_{11}$ is an unsubstituted aromatic hydrocarbon group having 6 to 30 ring carbon atoms or an unsubstituted heterocyclic group having 5 to 30 ring atoms and $L_1$ is a linking group.

4. The organic electroluminescence device according to claim 1, wherein $L_1$ is a single bond and $Ar_{11}$ is the same as $Ar_{12}$.

5. The organic electroluminescence device according to claim 1, wherein the first compound is represented by a formula (10) below, (10)

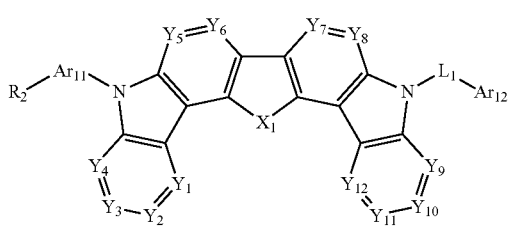

where:

$X_1$, $Y_1$ to $Y_{12}$, $L_1$, $Ar_{11}$ and $Ar_{12}$ respectively represent the same as $X_1$, $Y_1$ to $Y_{12}$, $L_1$, $Ar_{11}$ and $Ar_{12}$ in the formula (1); and $R_2$ is a substituent and is a substituted or unsubstituted aromatic hydrocarbon group having 6 to 30 ring carbon atoms or a substituted or unsubstituted heterocyclic group having 5 to 30 ring atoms.

6. The organic electroluminescence device according to claim 5, wherein $Ar_{11}$ and $L_1$ are the same and $R_2$ and $Ar_{12}$ are the same.

7. The organic electroluminescence device according to claim 1, wherein $Ar_{12}$ is a group represented by a formula (11) below, (11)

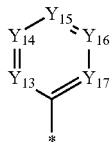

where:

* is a point of attachment, $Y_{13}$ to $Y_{17}$ are each independently a nitrogen atom or $CR_3$;

$R_3$ is a hydrogen atom or a substituent;

when $R_3$ is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group;

a plurality of $R_3$ are optionally mutually the same or different; and when at least two of the plurality of $R_3$ are substituents, the substituents $R_3$ are optionally mutually bonded to form a cyclic structure.

8. The organic electroluminescence device according to claim 7, wherein at least one of $Y_{13}$ to $Y_{17}$ is a nitrogen atom.

9. The organic electroluminescence device according to claim 7, wherein $Y_{13}$ to $Y_{17}$ are each independently $CR_3$.

10. The organic electroluminescence device according to claim 7, wherein at least one of $R_3$ is a cyano group.

11. The organic electroluminescence device according to claim 7, wherein $Ar_{12}$ is a group represented by a formula (11a) below, a group represented by a formula (11b) below, a group represented by a formula (11c) below, a group represented by a formula (11d) below, or a group represented by a formula (11e) below, (11a)

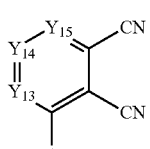

(11b)

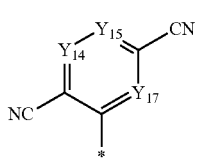

-continued

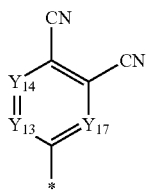
(11c)

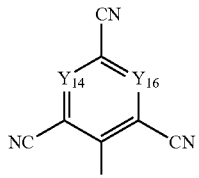
(11d)

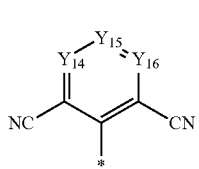
(11e)

where:
* is a point of attachment,
in the formulae (11a) to (11e), $Y_{13}$ to $Y_{17}$ respectively represent the same as $Y_{13}$ to $Y_{17}$ in the formula (11).

12. The organic electroluminescence device according to claim 7, wherein
$Ar_{12}$ is a group represented by a formula (11f) below, a group represented by a formula (11g) below, or a group represented by a formula (11h) below,

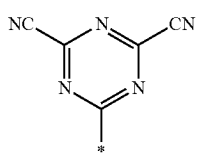
(11f)

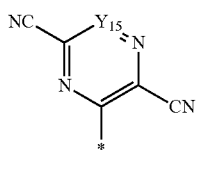
(11g)

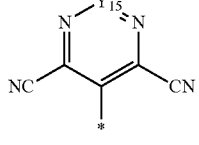
(11h)

in the formulae (11g) to (11h), * is a point of attachment, and $Y_{15}$ represents the same as $Y_{15}$ in the formula (11).

13. The organic electroluminescence device according to claim 11, wherein $Y_{13}$ to $Y_{17}$ are $CR_3$, in which $R_3$ is a hydrogen atom.

14. The organic electroluminescence device according to claim 1, wherein $L_1$ is a substituted or unsubstituted aromatic hydrocarbon group having 6 to 30 ring carbon atoms, or a substituted or unsubstituted heterocyclic group having 5 to 30 ring atoms.

15. The organic electroluminescence device according to claim 1, wherein $X_1$ is an oxygen atom or a sulfur atom.

16. The organic electroluminescence device according to claim 1, wherein $Y_1$ to $Y_{12}$ are $CR_1$, in which $R_1$ is a hydrogen atom.

17. The organic electroluminescence device according to claim 1, wherein
the partial structure represented by the formula (21) is in a form of at least one group selected from the group consisting of groups represented by formulae (23) and (24) below and is contained in the second compound,

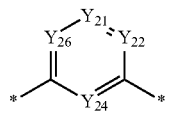
(23)

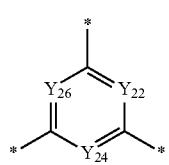
(24)

where: in the formulae (23) and (24):
* is a point of attachment;
$Y_{21}$, $Y_{22}$, $Y_{24}$ and $Y_{26}$ are each independently a nitrogen atom or $CR_{21}$;
$R_{21}$ is a hydrogen atom or a substituent; and
when $R_{21}$ is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{21}$ being a non-fused ring.

18. The organic electroluminescence device according to claim 17, wherein
$R_{21}$ is a hydrogen atom or a substituent; and
when $R_{21}$ is a substituent, the substituent is selected from the group consisting of a fluorine atom, a cyano group, a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms, the substituted or unsubstituted aromatic hydrocarbon group having 6 to 30 ring carbon atoms in $R_{21}$ being a non-fused ring.

19. The organic electroluminescence device according to claim 17, wherein $R_{21}$ is a hydrogen atom, a substituted or unsubstituted aromatic hydrocarbon group having 6 to 30 ring carbon atoms, or a substituted or unsubstituted heterocyclic group having 5 to 30 ring atoms.

20. The organic electroluminescence device according to claim 17, wherein $Y_{21}$, $Y_{22}$, $Y_{24}$ and $Y_{26}$ are each independently $CR_{21}$.

21. The organic electroluminescence device according to claim 17, wherein the partial structure represented by the formula (22) is in a form of at least one group selected from the group consisting of a group represented by a formula (25) below, a group represented by a formula (26) below, a group represented by a formula (27) below, a group represented by a formula (28) below, a group represented by a formula (29) below and a group represented by a formula (30) below, and is contained in the second compound,

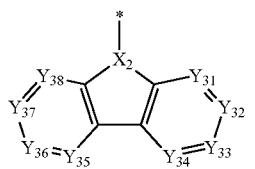

(25)

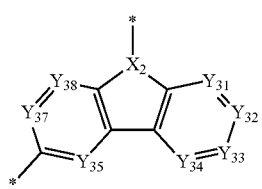

(26)

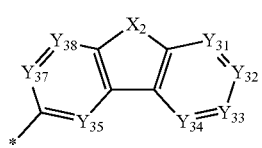

(27)

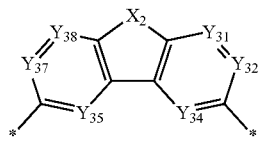

(28)

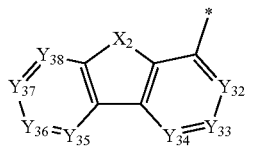

(29)

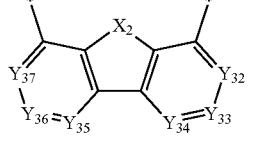

(30)

where: in the above formulae (25) to (30):

* is a point of attachment;

$Y_{31}$ to $Y_{38}$ are each independently a nitrogen atom or $CR_{22}$;

$R_{22}$ is a hydrogen atom or a substituent;

when $R_{22}$ is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{22}$ being a non-fused ring;

$X_2$ in the formulae (25) and (26) is a nitrogen atom;

$X_2$ in (27) to (30) is $NR_{23}$, an oxygen atom or a sulfur atom; and $R_{23}$ is a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{23}$ being a non-fused ring.

22. The organic electroluminescence device according to claim 21, wherein $Y_{31}$ to $Y_{38}$ in the formula (25) are each independently $CR_{22}$, $Y_{31}$ to $Y_{35}$, $Y_{37}$ and $Y_{38}$ in the formulae (26) and (27) are each independently $CR_{22}$, $Y_{31}$, $Y_{32}$, $Y_{34}$, $Y_{35}$, $Y_{37}$ and $Y_{38}$ in the formula (28) are each independently $CR_{22}$, $Y_{32}$ to $Y_{38}$ in the formula (29) are each independently $CR_{22}$, $Y_{32}$ to $Y_{37}$ in the formula (30) are each independently $CR_{22}$, and a plurality of $R_{22}$ are mutually the same or different.

23. The organic electroluminescence device according to claim 21, wherein $R_{22}$ is a hydrogen atom or a substituent; and when $R_{22}$ is a substituent, the substituent is selected from the group consisting of a fluorine atom, a cyano group, a substituted or unsubstituted alkyl group having 1 to 30 carbon atoms, a substituted or unsubstituted aromatic hydrocarbon group having 6 to 30 ring carbon atoms and a substituted or unsubstituted heterocyclic group having 5 to 30 ring atoms, the substituted or unsubstituted aromatic hydrocarbon group having 6 to 30 ring carbon atoms in $R_{22}$ being a non-fused ring.

24. The organic electroluminescence device according to claim 21, wherein $R_{22}$ is a hydrogen atom, a substituted or unsubstituted aromatic hydrocarbon group having 6 to 30 ring carbon atoms, or a substituted or unsubstituted heterocyclic group having 5 to 30 ring atoms, the substituted or unsubstituted aromatic hydrocarbon group having 6 to 30 ring carbon atoms in $R_{22}$ being a non-fused ring.

25. The organic electroluminescence device according to claim 1, wherein the second compound has the partial structures represented by the formula (21) and the formula (22), and the partial structures represented by the formulae (21) and (22) are in a form of a group represented by formula (20A) below, (20A)

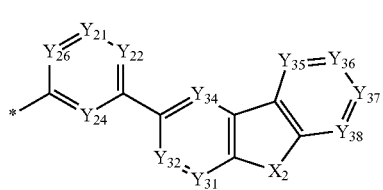

where:
* is a point of attachment;
$Y_{21}$, $Y_{22}$, $Y_{24}$ and $Y_{26}$ are each independently a nitrogen atom or $CR_{21}$;
$Y_{31}$, $Y_{32}$ and $Y_{34}$ to $Y_{38}$ are each independently a nitrogen atom, $CR_{22}$ or a carbon atom bonded to another atom in the molecule of the second compound;
$R_{21}$ and $R_{22}$ are each independently a hydrogen atom or a substituent;
when $R_{21}$ and $R_{22}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{21}$ and $R_{22}$ being a non-fused ring;
$X_2$ is $NR_{23}$, an oxygen atom or a sulfur atom;
$R_{23}$ is a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or un substituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{23}$ being a non-fused ring;
$Y_{22}$ and $Y_{34}$ are optionally cross-linked via an oxygen atom, sulfur atom or $CR_{51}R_{52}$;
$Y_{24}$ and $Y_{32}$ are optionally cross-linked via an oxygen atom, sulfur atom or $CR_{53}R_{54}$; and
$R_{51}$ to $R_{54}$ each independently represent the same as $R_{23}$ being the substituent.

26. The organic electroluminescence device according to claim 1, wherein the second compound has the partial structures represented by the formula (21) and the formula (22), and the partial structures represented by the formulae (21) and (22) are in a form of a group represented by formula (20B) below, (20B)

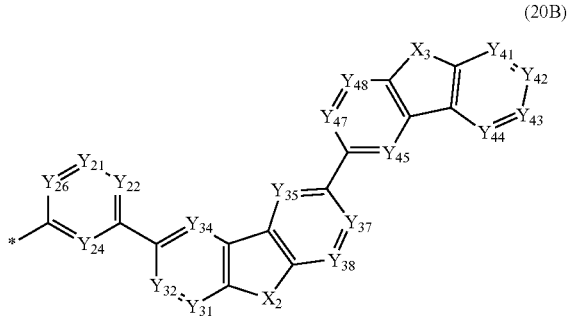

where:
* is a point of attachment;
$Y_{21}$, $Y_{22}$, $Y_{24}$ and $Y_{26}$ are each independently a nitrogen atom or $CR_{21}$;
$Y_{31}$, $Y_{32}$, $Y_{34}$, $Y_{35}$, $Y_{37}$ and $Y_{38}$ are each independently a nitrogen atom or $CR_{22}$;
$Y_{41}$ to $Y_{45}$, $Y_{47}$ and $Y_{48}$ are each independently a nitrogen atom, $CR_{24}$ or a carbon atom bonded to another atom in the molecule of the second compound;
$R_{21}$, $R_{22}$ and $R_{24}$ are each independently a hydrogen atom or a sub stituent;
when $R_{21}$, $R_{22}$ and $R_{24}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{21}$, $R_{22}$ and $R_{24}$ being a non-fused ring;
$X_2$ is $NR_{23}$, an oxygen atom or a sulfur atom;
$X_3$ is $NR_{25}$, an oxygen atom or a sulfur atom;
$R_{23}$ and $R_{25}$ are each independently a substituent;
the substituent is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{23}$ and $R_{25}$ being a non-fused ring;
$Y_{22}$ and $Y_{34}$ are optionally cross-linked via an oxygen atom, sulfur atom or $CR_{51}R_{52}$;
$Y_{24}$ and $Y_{32}$ are optionally cross-linked via an oxygen atom, sulfur atom or $CR_{53}R_{54}$; and $R_{51}$ to $R_{54}$ each independently represent the same as $R_{23}$ and $R_{25}$ being the substituent.

27. The organic electroluminescence device according to claim 1, wherein the second compound has the partial structures represented by the formula (21) and the partial structure represented by the formula (21) is in a form of a group represented by formula (20C):

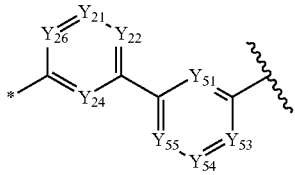

(20C)

where:
* is a point of attachment;
$Y_{21}$, $Y_{22}$, $Y_{24}$ and $Y_{26}$ are each independently a nitrogen atom or $CR_{21}$;
$Y_{51}$, $Y_{53}$, $Y_{54}$ and $Y_{55}$ are each independently a nitrogen atom or $CR_{26}$;
$R_{21}$ and $R_{26}$ are each independently a hydrogen atom or a substituent;
when $R_{21}$ and $R_{26}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{21}$ and $R_{26}$ being a non-fused ring;
$Y_{22}$ and $Y_{51}$ are optionally cross-linked via an oxygen atom, sulfur atom or $CR_{55}R_{56}$;
$Y_{24}$ and $Y_{55}$ are optionally cross-linked via an oxygen atom, sulfur atom or $CR_{57}R_{58}$; and
$R_{55}$ to $R_{58}$ are each independently a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{55}$ to $R_{58}$ being a non-fused ring.

28. The organic electroluminescence device according to claim 1, wherein the second compound has the partial structure represented by the formula (21) and the formula (22) and the partial structures represented by the formulae (21) and (22) are in a form of a group represented by formula (20D):

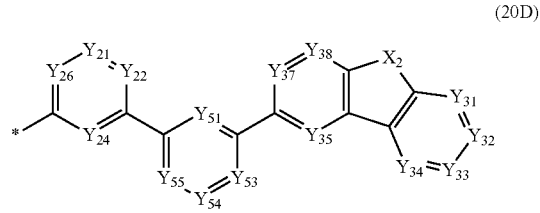

(20D)

where:
* is a point of attachment;
$Y_{21}$, $Y_{22}$, $Y_{24}$ and $Y_{26}$ are each independently a nitrogen atom or $CR_{21}$;
$Y_{51}$, $Y_{53}$, $Y_{54}$ and $Y_{55}$ are each independently a nitrogen atom or $CR_{26}$;
$Y_{31}$ to $Y_{35}$, $Y_{37}$ and $Y_{38}$ are each independently a nitrogen atom, $CR_{22}$ or a carbon atom bonded to another atom in the molecule of the second compound;
$R_{21}$, $R_{22}$ and $R_{26}$ are each independently a hydrogen atom or a sub stituent;
when $R_{21}$, $R_{22}$ and $R_{26}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{21}$, $R_{22}$ and $R_{26}$ being a non-fused ring;
$X_2$ is $NR_{23}$, an oxygen atom or a sulfur atom;
$R_{23}$ is a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{23}$ being a non-fused ring;
$Y_{22}$ and $Y_{51}$ are optionally cross-linked via an oxygen atom, sulfur atom or $CR_{55}R_{56}$;
$Y_{24}$ and $Y_{55}$ are optionally cross-linked via an oxygen atom, sulfur atom or $CR_{57}R_{58}$;
$Y_{51}$ and $Y_{37}$ are optionally cross-linked via an oxygen atom, sulfur atom or $CR_{59}R_{60}$;

$Y_{53}$ and $Y_{35}$ are optionally cross-linked via an oxygen atom, sulfur atom or $CR_{61}R_{62}$; and $R_{55}$ to $R_{62}$ each independently represent the same as $R_{23}$ being the substituent.

29. The organic electroluminescence device according to claim 1, wherein the second compound has the partial structure represented by the formula (22) and the partial structure represented by formula (22) is in a form of a group represented by formula (20E):

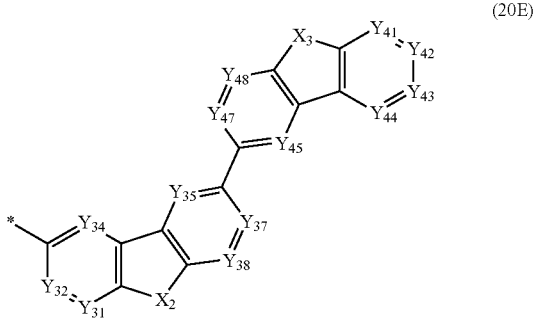

(20E)

where:
* is a point of attachment;
$Y_{31}$, $Y_{32}$, $Y_{34}$, $Y_{35}$, $Y_{37}$ and $Y_{38}$ are each independently a nitrogen atom or $CR_{22}$, $Y_{41}$ to $Y_{45}$, $Y_{47}$ and $Y_{48}$ are each independently a nitrogen atom, $CR_{24}$ or a carbon atom bonded to another atom in the molecule of the second compound;
$R_{22}$ and $R_{24}$ are each independently a hydrogen atom or a substituent;
when $R_{22}$ and $R_{24}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{22}$ and $R_{24}$ being a non-fused ring;
$X_2$ is $NR_{23}$, an oxygen atom or a sulfur atom;
$X_3$ is $NR_{25}$, an oxygen atom or a sulfur atom;
$R_{23}$ and $R_{25}$ are each independently a hydrogen atom or a substituent; and
when $R_{23}$ and $R_{25}$ are substituents, the substituents are each selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, the substituted or unsubstituted aromatic hydrocarbon group having 6 to 30 ring carbon atoms in $R_{23}$ and $R_{25}$ being a non-fused ring.

30. The organic electroluminescence device according to claim 1, further comprising: a hole transporting layer between the anode and the emitting layer.

31. The organic electroluminescence device according to claim 1, further comprising: an electron transporting layer between the cathode and the emitting layer.

32. An electronic device, comprising the organic electroluminescence device according to claim 1.

33. The organic electroluminescence device according to claim 12, wherein $Y_{15}$ is $CR_3$, in which $R_3$ is a hydrogen atom.

34. The organic electroluminescence device according to claim 1, wherein the first compound emits light when the organic electroluminescence device is driven.

35. The organic electroluminescence device according to claim 1, wherein the emitting layer is a fluorescent emitting layer.

36. The organic electroluminescence device according to claim 1, wherein the first compound emits delayed fluorescence when the organic electroluminescence device is driven.

37. The organic electroluminescence device according to claim 2, wherein one of —$Ar_{11}$ and —$L_1$—$Ar_{12}$ is an electron donor and the other thereof is an electron acceptor.

* * * * *